US010945974B2

(12) United States Patent
Celiker

(10) Patent No.: US 10,945,974 B2
(45) Date of Patent: Mar. 16, 2021

(54) METHODS AND COMPOSITIONS TO MODULATE THE GUT MICROBIOTA AND TO MANAGE WEIGHT

(71) Applicant: XENO BIOSCIENCES INC., Cambridge, MA (US)

(72) Inventor: Hasan Celiker, Cambridge, MA (US)

(73) Assignee: Xeno Biosciences Inc., Cambridge, MA (US)

( * ) Notice: Subject to any disclaimer, the term of this patent is extended or adjusted under 35 U.S.C. 154(b) by 0 days.

(21) Appl. No.: 15/575,942

(22) PCT Filed: May 31, 2016

(86) PCT No.: PCT/US2016/034973
§ 371 (c)(1),
(2) Date: Nov. 21, 2017

(87) PCT Pub. No.: WO2016/196440
PCT Pub. Date: Dec. 8, 2016

(65) Prior Publication Data
US 2018/0147167 A1 May 31, 2018

Related U.S. Application Data

(60) Provisional application No. 62/327,283, filed on Apr. 25, 2016, provisional application No. 62/169,480, filed on Jun. 1, 2015.

(51) Int. Cl.
| | |
|---|---|
| *A61K 31/17* | (2006.01) |
| *A61K 38/44* | (2006.01) |
| *A61K 33/40* | (2006.01) |
| *A61K 9/48* | (2006.01) |
| *A61K 33/00* | (2006.01) |
| *A61K 9/28* | (2006.01) |
| *A61P 3/00* | (2006.01) |
| *A61P 3/04* | (2006.01) |
| *A61K 9/00* | (2006.01) |
| *A61K 31/185* | (2006.01) |
| *A61K 31/327* | (2006.01) |

(52) U.S. Cl.
CPC ............ *A61K 31/17* (2013.01); *A61K 9/0053* (2013.01); *A61K 9/2846* (2013.01); *A61K 9/2866* (2013.01); *A61K 9/4866* (2013.01); *A61K 9/4891* (2013.01); *A61K 31/185* (2013.01); *A61K 31/327* (2013.01); *A61K 33/00* (2013.01); *A61K 33/40* (2013.01); *A61K 38/44* (2013.01); *A61P 3/00* (2018.01); *A61P 3/04* (2018.01); *C12Y 111/01006* (2013.01)

(58) Field of Classification Search
None
See application file for complete search history.

(56) References Cited

U.S. PATENT DOCUMENTS

| | | |
|---|---|---|
| 5,759,539 A | 6/1998 | Whitmire |
| 9,855,294 B2 | 1/2018 | Heshmati et al. |
| 2004/0146467 A1 | 7/2004 | Pellico |
| 2005/0008584 A1 | 1/2005 | Montgomery |
| 2006/0110451 A1 | 5/2006 | Lin et al. |
| 2006/0193794 A1 | 8/2006 | Kim et al. |
| 2006/0270655 A1 | 11/2006 | Swick et al. |
| 2009/0169630 A1* | 7/2009 | Ward ............... A01N 59/00 424/489 |
| 2010/0092550 A1 | 4/2010 | Cabral |
| 2010/0172874 A1 | 7/2010 | Turnbaugh |
| 2011/0002986 A1 | 1/2011 | Durig |
| 2012/0052151 A1 | 3/2012 | Sannino et al. |
| 2012/0058094 A1 | 3/2012 | Blaser et al. |
| 2013/0012590 A1 | 1/2013 | Zadini et al. |
| 2013/0195830 A1 | 8/2013 | Sipka et al. |
| 2013/0295525 A1 | 11/2013 | Sagel |
| 2014/0212492 A1 | 7/2014 | Mateescu |
| 2020/0078397 A1 | 3/2020 | Celiker |

FOREIGN PATENT DOCUMENTS

| | | |
|---|---|---|
| WO | 96/39174 | 12/1996 |
| WO | WO2007134304 A1 | 11/2007 |
| WO | 2008/076696 A2 | 6/2008 |
| WO | 2010/101844 A1 | 9/2010 |

(Continued)

OTHER PUBLICATIONS

Quintero et al, "Impact of oxygen availability on body weight management," Medical Hypotheses, vol. 74, No. 5, pp. 901-907 (Year: 2010).*
Xue et al, "Preparation and characterization of calcium-shellac spheres as a carrier of carbamide peroxide," Journal of Microencapsulation, vol. 25, No. 8, pp. 523-530 (Year: 2008).*
"Berberine and Its Many Benefits," Feb. 24, 2018, accessed on Dec. 7, 2018, at https://enzymedica.com/blogs/naturaldigestivehealth/berberine-and-its-many-benefits.
Carmen Calinescu, et al., "Carboxymethyl starch: Chitosan monolithic matrices containing diamine oxidase and catalase for intestinal delivery," International Journal of Pharmaceutics, 428 (2012 48-56.
Catalase Supplement, accessed on Dec. 7, 2018, at https://shop.suzycohen.com/products/catalase.

(Continued)

*Primary Examiner* — Dennis J Parad
(74) *Attorney, Agent, or Firm* — Choate, Hall & Stewart LLP; Brenda Herschbach Jarrell; David E. Shore

(57) ABSTRACT

Methods of weight management for a subject are provided. Generally the methods comprising: administering an effective amount to the small intestine and/or large intestine of the subject of at least one agent that increases oxygen tension and/or redox potential and/or pH in the colon of the subject to thereby manage the weight of the subject. Also provided are compositions comprising at least one agent that increases oxygen tension and/or redox potential and/or pH, wherein the composition is formulated for delivery of an effective amount of the at least one agent to the small intestine and/or large intestine of a subject following oral administration of the composition to the subject.

27 Claims, 9 Drawing Sheets

(56) References Cited

FOREIGN PATENT DOCUMENTS

| | | |
|---|---|---|
| WO | WO-2010/101844 A1 | 9/2010 |
| WO | WO-2010/134827 A1 | 11/2010 |
| WO | 2013/093877 A2 | 6/2013 |
| WO | 2013/103919 A2 | 7/2013 |
| WO | 2013/130773 A2 | 9/2013 |
| WO | 2014/046804 A1 | 3/2014 |
| WO | WO-2014/046804 A1 | 3/2014 |
| WO | 2015/000053 A1 | 1/2015 |
| WO | 2016/094218 A1 | 6/2016 |
| WO | WO-2016/094218 A1 | 6/2016 |
| WO | 2016/172658 A2 | 10/2016 |
| WO | WO-2016/172658 A2 | 10/2016 |
| WO | WO-2016/196440 A1 | 12/2016 |
| WO | 2018/102469 A1 | 6/2018 |
| WO | WO-2018/102469 A1 | 6/2018 |
| WO | WO-2018/203083 A2 | 11/2018 |
| WO | WO-2019/037682 A1 | 2/2019 |

OTHER PUBLICATIONS

Edward S. Chambers, et al., "Effects of targeted delivery of propionate to the human colon on appetite regulation, body weight maintenance and adiposity in overweight adults," Gut 2015;64:1744-1754.

Homozon web page, "http://hello-earth.com/homozon/listen/georgefreibotthomozon17march2011.html," accessed Sep. 7, 2018.

George Kunnackal John, et al., "Dietary Alteration of the Gut Microbiome and Its Impact on Weight and Fat Mass: A Systematic Review and Meta-Analysis," Genes 2018, 9, 167.

MagO7 Product Information Guide, accessed on Dec. 7, 2018, at https://www.dropbox.com/s/1t58btqm5wqu0qb/LEONARD_magO7_90ct_2018.pdf?dl=0.

"Thread: My experience of taking Hydrogen Peroxide 35% food grade, diluted in water," Jun. 1, 2014, accessed Dec. 7, 2018, at http://projectavalon.net/forum4/showthread.php?71893-My-experience-of-taking-Hydrogen-Peroxide-35-food-grade-diluted-in-water.

Nutritional Brands—MagO7, available at http://www.nbpure.us/mago7/, accessed Aug. 8, 2018.

Jogender K. Lalla, et al., "Efficacy, Safety, and Tolerability Evaluation of Global Healing Center's Oxy Powder® in Treating Irritable Bowel Syndrome (Constipation-Predominant) (IBS-C)," International Journal of Pharma and Bio Sciences, V1 (2) 2010.

Honglin Sun, et al., "Modulation of Microbiota-Gut-Brain Axis by Berberine Resulting in Improved Metabolic Status in High-Fat Diet-Fed Rats," Obesity Facts, 2016;9:356-378.

Your Top Oxy Powder Frequently Asked Questions Answered, available at https://thewellbeingclinic.ie/oxypowder/oxypowder-frequently-asked-questions/, accessed on Dec. 7, 2018.

Xu Zhang, et al., "Modulation of gut microbiota by berberine and metformin during the treatment of high-fat diet-induced obesity in rats," Sci. Rep. 5, 14405; doi: 10.1038/srep14405 (2015).

International Search Report and Written Opinion for Application No. PCT/US16/34973, dated Sep. 9, 2016.

K.R. Ward, et al., "Chemical Oxygen Generation," Resperatory Care, vol. 58, No. 1, pp. 184-195 (2013).

European Search Report, Application No. 16804207.5, dated Jan. 24, 2019.

"The steps I took to lose weight", Internet, 122 May 2015 (May 12, 2015), XP002787110, Retrieved from the Internet: URL:https://web.archive.org/web/20150512104604/http://myplace.frontier.com/-felipe2/id26.html [retrieved on Dec. 5, 2018].

"Catalase, How Catalase Works", May 2, 2015 (May 2, 2015), XP002787111, Retrieved from the Internet: URL:https://www.ebi.ac.uk/interpro/potm/2004 9/Page2.htm [retrieved on Dec. 5, 2018].

G Abdeen, et al., "Mechanism Underlying the Weight Loss and Complications of Roux-en-Y Gastric Bypass. Review," Obes Surg (2016) 26:410-421.

Deanna M. Arble, et al., "Mechanisms underlying weight loss and metabolic improvements in rodent models of bariatric surgery," Diabetologia. Feb. 2015; 58(2):211-220.

Husen Zhang, et al., "Human gut microbiota in obesity and after gastric bypass," PNAS, vol. 106, No. 7, pp. 2365-2370.

Antje Damms-Machado, et al., "Effects of Surgical and Dietary Weight Loss Therapy for Obesity on Gut Microbiota Composition and Nutrient Absorption," Hindawi Publishing Corporation, BioMed Research International, vol. 2015, Article ID 806248, 12 pages.

Amber L. Hartmana, et al., "Human gut microbiome adopts an alternative state following small bowel transplantation," PNAS, Oct. 6, 2009, vol. 106, No. 40, pp. 17187-17192.

Zehra Esra Ilhan, "Microbiome After Bariatric Surgery and Microbial Insights into Surgical Weight Loss," Dissertation, Arizona State University, 2016.

Jia V Li, et al., "Metabolic surgery profoundly influences gut microbialehost metabolic cross-talk," Gut 2011;60:1214-1223.

Alice P. Liou, et al., "Conserved Shifts in the Gut Microbiota Due to Gastric Bypass Reduce Host Weight and Adiposity," Sci Transl Med 5, 178ra41 (2013) DOI: 10.1126/scitranslmed.3005687.

Christine M. Peat, et al., "The Intestinal Microbiome in Bariatric Surgery Patients," Eur Eat Disord Rev. Nov. 2015; 23(6): 496-503.

J Graessler, et al., "Metagenomic sequencing of the human gut microbiome before and after bariatric surgery in obese patients with type 2 diabetes: correlatin with inflammatory and metabolic parameters," The Pharmacogenomics Journal (2013) 13, 514-522.

Karen K. Ryan, et al., "FXR is a molecular target for the effects of vertical sleeve gastrectomy," Nature, vol. 509, pp. 183-190 (2014).

Nima Saeidi, et al., "Reprogramming of Intestinal Glucose Metabolism and Glycemic Control in Rats After Gastric Bypass," Science, vol. 341, pp. 406-410 (2013).

Randy J. Seeley, et al., "The Role of Gut Adaptation in the Potent Effects of Multiple Bariatric Surgeries on Obesity and Diabetes," Cell Metabolism 21, Mar. 3, 2015, 369-378.

Ruth E. Ley, et al., "Human gut microbes associated with obesity," Nature, vol. 444, Dec. 21/Dec. 28, 2006, pp. 1022-23.

Ruth E. Ley, et al., "Obesity alters gut microbial ecology," PNAS, vol. 102, No. 31, pp. 11070-75 (2005).

Peter J. Turnbaugh, et al., "A core gut microbiome in obese and lean twins," Nature. Jan. 22, 2009; 457(7228): 480-484.

International Search Report and Written Opinion for Application No. PCT/US17/63809, dated Feb. 6, 2018 (8 pages).

Chambers, AP et al., Weight-independent changes in blood glucose homeostasis after gastric bypass or vertical sleeve gastrectomy in rats, Gastroenterology, 141:950-8 (2011).

Ciangura, C. et al., Dynamics of change in total and regional body composition after gastric bypass in obese patients, Obesity (Silver Spring), 18:760-5 (2010).

Crowe, T.C., Safety of low-carbohydrate diets, Obes Rev, 6:235-45 (2005).

Flint, A. et al., Reproducibility, power and validity of visual analogue scales in assessment of appetite sensations in single test meal studies, Int. J Obes. Relat. Metab. Disord, 24:38-48 (2000).

Foster, D.W. and McGarry, J.D., The regulation of ketogenesis, Ciba Found Symp., 87:120-31 (1982).

Friedrich, N. et al., Short-term changes of the urine metabolome after bariatric surgery, OMICS, 16:612-20 (2012).

Gralka E. et al., Metabolomic fingerprint of severe obesity is dynamically affected by bariatric surgery in a procedure-dependent manner, Am. J Clin. Nutr., 102:1313-22 (2015).

Jensen, M. et al., Insulin regulation of lipolysis in nondiabetic and IDDM subjects, Diabetes, 38:1595-601 (1989).

Mor, A. et al., Weight loss at first postoperative visit predicts long-term outcome of Roux-en-Y gastric bypass using Duke weight loss surgery chart, Surg Obes Relat Dis, 8:556-60 (2012).

Sodium Percarbonate SIDS Initial Assessment Profile, In Organisation for Economic Co-operation and Development Existing Chemicals Database, retrieved from https://hpvchemicals.oecd.org/ui/handler.axd?id=ab75c996-6905-4195-9e2c-5abd5e465d5b, 3 pages (2005).

Palaniappan, L.P., Heterogeneity in the Relationship Between Ethnicity, BMI, and Fasting Insulin, Diabetes Care, 25 (2002).

Savendahl, L. and Underwood, L. E., Fasting increases serum total cholesterol, LDL cholesterol and apolipoprotein B in healthy, nonobese humans, J Nutr., 129:2005-8 (1999).

(56) References Cited

OTHER PUBLICATIONS

Swaner, J.C., and Connor, W. E., Hypercholesterolemia of total starvation: its mechanism via tissue mobilization of cholesterol, Am. J Physiol., 229:365-9 (1975).
Wickremesekera, K. et al., Loss of insulin resistance after Roux-en-Y gastric bypass surgery: a time course study, Obes Surg, 15:474-81 (2005).

* cited by examiner

METHODS AND COMPOSITIONS TO MODULATE THE GUT MICROBIOTA AND TO MANAGE WEIGHT

INTRODUCTION

With only diet, exercise, and bariatric surgery as options, the lack of effective and safe medications for treating metabolic disorders and diseases (such as obesity), metabolic syndrome, and cardiovascular disease are significant unmet medical needs. For example, obesity is a life-threatening disorder in which there is an increased risk of morbidity and mortality arising from concomitant diseases such as type II diabetes, hypertension, obstructive sleep apnea, inflammation, stroke, cancer and gallbladder disease. Obesity is now a major healthcare issue in the Western World and increasingly in some third world countries. Currently about 35% of the population of the USA is now considered obese and an additional ~40% overweight. Management of body weight and body mass index (BMI) is also correlated with many indicators of health and even a numerically small reduction of body weight can lead to a profound improvement in obesity related conditions and increase quality of life and life expectancy.

Microbiome targeted therapeutics have a potential to address this problem, as it is becoming increasingly clear that the gut microbiota has a causal role in alleviating or mediating metabolic disorders, including obesity. However, microbiome modulation approaches to date have predominantly focused on utilizing probiotics, prebiotics, antibiotics or fecal transplants, which lack targeted or broad-spectrum efficacy and may have unfavorable safety and efficacy profiles. Accordingly, there is a need for new methods and compositions for treating metabolic disorders including obesity, metabolic syndrome, and cardiovascular disease. The inventions disclosed herein meet these and other needs.

SUMMARY

The inventor has discovered that administering an effective amount to the small intestine and/or large intestine of a subject of at least one agent that increases oxygen tension and/or redox potential and/or pH in the colon of the subject has a beneficial effect on the gut microbiome of the subject. By increasing the oxygen tension and/or redox potential and/or pH the colon environment is modified such that (1) the relative abundance of bacterial types known to promote at least one condition selected from a metabolic disease or disorder (such as obesity), metabolic syndrome, and cardiovascular disease is reduced; and/or (2) the relative abundance of bacterial types known to ameliorate at least one condition selected from a metabolic disease or disorder (such as obesity), metabolic syndrome, and cardiovascular disease is increased.

Accordingly, in a first aspect this invention provides methods of modifying the gut microbiome of a subject. In some embodiments the methods comprise administering at least one agent that increases oxygen tension and/or redox potential and/or pH in the colon of a subject. In some embodiments the at least one agent is administered by administering an effective amount of the at least one agent to the small intestine and/or large intestine of the subject. In some embodiments the at least one agent increases oxygen tension and is a peroxide. In some embodiments the at least one agent increases pH and is selected from bicarbonate salts, carbonate salts, bases, and buffers. In some embodiments the at least one agent is a peroxide catalyst. In some embodiments the at least one agent is selected from carbamide peroxide, sodium percarbonate, sodium bicarbonate, and catalase. In some embodiments the method comprises administering a peroxide and catalase to the subject. In some embodiments the peroxide is selected from carbamide peroxide, sodium percarbonate. In some embodiments the method further comprises administering sodium bicarbonate to the subject.

In some embodiments the effective amount of at least one of an agent that increases oxygen tension and/or redox potential and/or pH is administered to the small intestine and/or large intestine of the subject by oral administration of the at least one agent to the subject. In some embodiments the at least one agent is administered as an oral dosage form comprising the at least one agent and an enteric coating encasing the at least one agent. In some embodiments the oral dosage form is formulated for sustained release.

In some embodiments the relative abundance of at least one of aerobic bacteria and facultatively anaerobic bacteria is increased in the microbiota of the colon of the subject. In some embodiments the relative abundance of bacteria in at least one phylum selected from Proteobacteria, Bacteriodetes, and Verrucomicrobia is increased in the microbiota of the colon of the subject. In some embodiments the relative abundance of bacteria in the Proteobacteria phylum is increased in the microbiota of the colon of the subject. In some embodiments the relative abundance of bacteria in the Firmicutes phylum is decreased in the microbiota of the colon of the subject. In some embodiments the relative abundance of bacteria in at least one phylum selected from Proteobacteria, Bacteriodetes, and Verrucomicrobia is increased in the microbiota of the colon of the subject; and the relative abundance of bacteria in the Firmicutes phylum is decreased in the microbiota of the colon of the subject.

In some embodiments of the methods the at least one agent that increases oxygen tension and/or redox potential and/or pH in the colon of a subject is administered to the subject for a dosing period. In some embodiments the body mass of the subject is reduced at the end of the dosing period compared to the beginning of the dosing period. In some embodiments the body mass of the subject is reduced at the end of the dosing period compared to the beginning of the dosing period.

In some embodiments of the methods the at least one agent that increases oxygen tension and/or redox potential and/or pH in the colon of a subject is administered to the subject without administering an enzyme to the subject. In some embodiments of the methods the at least one agent that increases oxygen tension and/or redox potential and/or pH in the colon of a subject is administered to the subject without administering an enzyme that oxidizes ethanol to acetate to the subject.

In some embodiments the methods comprise administering an effective amount to the small intestine and/or large intestine of the subject of at least one agent that increases oxygen tension and/or redox potential and/or pH in the colon of the subject; wherein administering the effective amount to the small intestine and/or large intestine of the subject of at least one agent that increases oxygen tension and/or redox potential and/or pH in the colon of the subject increases the relative abundance of at least one of aerobic bacteria and facultatively anaerobic bacteria in the microbiota of the colon of the subject by at least 100%.

In some embodiments the methods comprise administering an effective amount to the small intestine and/or large intestine of the subject of at least one agent that increases oxygen tension and/or redox potential and/or pH in the colon of the subject; wherein administering the effective amount to the small intestine and/or large intestine of the subject of at least one agent that increases oxygen tension and/or redox potential and/or pH in the colon of the subject increases the relative abundance of bacteria in at least one phylum selected from Proteobacteria, Bacteriodetes, and Verrucomicrobia is increased in the microbiota of the colon of the subject by at least 100%.

In some embodiments of the methods comprise administering an effective amount to the small intestine and/or large intestine of the subject of at least one agent that increases oxygen tension and/or redox potential and/or pH in the colon of the subject; wherein administering the effective amount to the small intestine and/or large intestine of the subject of at least one agent that increases oxygen tension and/or redox potential and/or pH in the colon of the subject increases the relative abundance of bacteria in the phylum Proteobacteria in the microbiota of the colon of the subject by at least 100%.

In some embodiments of the methods the effective amount of the at least one agent is administered to the small intestine and/or large intestine of the subject for a dosing period of at least five days and the weight of the subject is reduced by at least 2%.

In some embodiments of the methods the effective amount of the at least one agent is administered to the small intestine and/or large intestine of the subject for a dosing period of at least five days; the relative abundance of proteobacteria in the microbiota of the colon of the subject is increased by at least 100%; and the weight of the subject is reduced by at least 2%.

In some embodiments of the methods the at least one agent is selected from carbamide peroxide and sodium percarbonate. In some embodiments the methods further comprise administering catalase to the subject.

In some embodiments of the methods carbamide peroxide and catalase are administered orally. In some embodiments the subject is a human. In some embodiments the carbamide peroxide and catalase are each administered three times per day at a dose of at least 100 mg.

In some embodiments of the methods sodium percarbonate and catalase are administered orally. In some embodiments the subject is a human. In some embodiments the sodium percarbonate and catalase are each administered three times per day at a dose of at least 100 mg.

In another aspect this invention provides methods of weight management for a subject. In some embodiments the methods comprise administering an effective amount to the small intestine and/or large intestine of the subject of at least one agent that increases oxygen tension and/or redox potential and/or pH in the colon of the subject to thereby manage the weight of the subject. In some embodiments the weight management comprises at least one of weight loss, maintenance of weight, controlling weight gain, body mass index (BMI) reduction, maintenance of BMI, and controlling BMI gain. In some embodiments the subject is overweight or obese. In some embodiments the subject has at least one weight-related condition. In some embodiments the at least one weight-related condition is selected from a metabolic disease or disorder, metabolic syndrome, and cardiovascular disease. In some embodiments the at least one weight-related condition is selected from hypertension, dyslipidemia, and type 2 diabetes. In some embodiments at least one symptom of the at least one weight-related condition is ameliorated.

In some embodiments administering the effective amount to the small intestine and/or large intestine of the subject of at least one agent that increases oxygen tension and/or redox potential and/or pH in the colon of the subject increases the relative abundance of at least one of aerobic bacteria and facultatively anaerobic bacteria in the microbiota of the colon of the subject. In some embodiments administering the effective amount to the small intestine and/or large intestine of the subject of at least one agent that increases oxygen tension and/or redox potential and/or pH in the colon of the subject increases the relative abundance of bacteria in at least one phylum selected from Proteobacteria, Bacteriodetes, and Verrucomicrobia is increased in the microbiota of the colon of the subject. In some embodiments the relative abundance of bacteria in the phylum Proteobacteria is increased in the microbiota of the colon of the subject. In some embodiments administering the effective amount to the small intestine and/or large intestine of the subject of at least one agent that increases oxygen tension and/or redox potential and/or pH in the colon of the subject decreases the relative abundance of bacteria in the Firmicutes phylum in the microbiota of the colon of the subject. In some embodiments administering the effective amount to the small intestine and/or large intestine of the subject of at least one agent that increases oxygen tension and/or redox potential and/or pH in the colon of the subject decreases the relative abundance of bacteria in the Firmicutes phylum in the microbiota of the colon of the subject.

In some embodiments the at least one agent increases oxygen tension and is a peroxide. In some embodiments the at least one agent increases pH and is selected from bicarbonate salts, carbonate salts, bases, and buffers. In some embodiments the at least one agent is a peroxide catalyst. In some embodiments the at least one agent is selected from carbamide peroxide, sodium percarbonate, sodium bicarbonate, and catalase. In some embodiments the method comprises administering a peroxide and catalase to the subject. In some embodiments the peroxide is selected from carbamide peroxide, sodium percarbonate. In some embodiments the method further comprises administering sodium bicarbonate to the subject.

In some embodiments the effective amount of at least one of an agent that increases oxygen tension and/or redox potential and/or pH is administered to the small intestine and/or large intestine of the subject by oral administration of the at least one agent to the subject. In some embodiments the at least one agent is administered as an oral dosage form comprising the at least one agent and an enteric coating encasing the at least one agent. In some embodiments the oral dosage form is formulated for sustained release.

In some embodiments of the methods the at least one agent that increases oxygen tension and/or redox potential and/or pH in the colon of a subject is administered to the subject without administering an enzyme to the subject. In some embodiments of the methods the at least one agent that increases oxygen tension and/or redox potential and/or pH in the colon of a subject is administered to the subject without administering an enzyme that oxidizes ethanol to acetate to the subject.

In some embodiments the methods comprise administering an effective amount to the small intestine and/or large intestine of the subject of at least one agent that increases oxygen tension and/or redox potential and/or pH in the colon of the subject to thereby manage the weight of the subject; wherein administering the effective amount to the small intestine and/or large intestine of the subject of at least one agent that increases oxygen tension and/or redox potential and/or pH in the colon of the subject increases the relative abundance of at least one of aerobic bacteria and facultatively anaerobic bacteria in the microbiota of the colon of the subject by at least 100%.

In some embodiments the methods comprise administering an effective amount to the small intestine and/or large intestine of the subject of at least one agent that increases oxygen tension and/or redox potential and/or pH in the colon of the subject to thereby manage the weight of the subject; wherein administering the effective amount to the small intestine and/or large intestine of the subject of at least one agent that increases oxygen tension and/or redox potential and/or pH in the colon of the subject increases the relative abundance of bacteria in at least one phylum selected from Proteobacteria, Bacteriodetes, and Verrucomicrobia is increased in the microbiota of the colon of the subject by at least 100%.

In some embodiments the methods comprise administering an effective amount to the small intestine and/or large intestine of the subject of at least one agent that increases oxygen tension and/or redox potential and/or pH in the colon of the subject to thereby manage the weight of the subject; wherein administering the effective amount to the small intestine and/or large intestine of the subject of at least one agent that increases oxygen tension and/or redox potential and/or pH in the colon of the subject increases the relative abundance of bacteria in the phylum Proteobacteria is increased in the microbiota of the colon of the subject by at least 100%.

In some embodiments of the methods the effective amount of the at least one agent is administered to the small intestine and/or large intestine of the subject for a dosing period of at least five days.

In some embodiments of the methods the effective amount of the at least one agent is administered to the small intestine and/or large intestine of the subject for a dosing period of at least five days, and the weight of the subject in reduced by at least 2%.

In some embodiments of the methods the effective amount of the at least one agent is administered to the small intestine and/or large intestine of the subject for a dosing period of at least five days, and the relative abundance of proteobacteria in the microbiota of the colon of the subject is increased by at least 100%.

In some embodiments of the methods the effective amount of the at least one agent is administered to the small intestine and/or large intestine of the subject for a dosing period of at least five days, the weight of the subject in reduced by at least 2%, and the relative abundance of proteobacteria in the microbiota of the colon of the subject is increased by at least 100%.

In some embodiments of the methods the at least one agent is selected from carbamide peroxide and sodium percarbonate. In some embodiments the methods further comprise administering catalase to the subject.

In some embodiments of the methods carbamide peroxide and catalase are administered orally. In some embodiments the subject is a human. In some embodiments the carbamide peroxide and catalase are each administered three times per day at a dose of at least 100 mg.

In some embodiments of the methods sodium percarbonate and catalase are administered orally. In some embodiments the subject is a human. In some embodiments the sodium percarbonate and catalase are each administered three times per day at a dose of at least 100 mg.

In another aspect this invention provides compositions. In some embodiments the compositions comprise at least one agent that increases oxygen tension and/or redox potential and/or pH. In some embodiments the compositions are formulated for delivery of an effective amount of the at least one agent to the small intestine and/or large intestine of a subject following oral administration of the composition to the subject. In some embodiments the at least one agent increases oxygen tension and is a peroxide. In some embodiments the at least one agent increases pH and is selected from bicarbonate salts, carbonate salts, bases, and buffers. In some embodiments the at least one agent is a peroxide catalyst. In some embodiments the at least one agent is selected from carbamide peroxide, sodium percarbonate, sodium bicarbonate, and catalase. In some embodiments the composition comprises at least one of carbamide peroxide and sodium percarbonate, and further comprises catalase. In some embodiments the composition comprises at least one of carbamide peroxide and sodium percarbonate, further comprises catalase, and further comprises sodium bicarbonate.

In some embodiments the composition is formulated as an oral dosage form comprising the at least one agent and an enteric coating encasing the at least one agent. In some embodiments the oral dosage form is formulated for sustained release.

In some embodiments administering the effective amount of the composition to the small intestine and/or large intestine of a subject increases the relative abundance of at least one of aerobic bacteria and facultatively anaerobic bacteria in the microbiota of the colon of the subject. In some embodiments administering the effective amount of the composition to the small intestine and/or large intestine of the subject increases the relative abundance of bacteria in at least one phylum selected from Proteobacteria, Bacteriodetes, and Verrucomicrobia in the microbiota of the colon of the subject. In some embodiments administering the effective amount of the composition to the small intestine and/or large intestine of the subject increases the relative abundance of bacteria in the Proteobacteria phylum in the microbiota of the colon of the subject. In some embodiments administering the effective amount of the composition to the small intestine and/or large intestine of the subject decreases the relative abundance of bacteria in the Firmicutes phylum in the microbiota of the colon of the subject. In some embodiments administering the effective amount of the composition to the small intestine and/or large intestine of the subject decreases the relative abundance of bacteria in the Firmicutes phylum in the microbiota of the colon of the subject.

In some embodiments the composition that comprises at least one agent that increases oxygen tension and/or redox potential and/or pH in the colon of a subject does not comprise an enzyme. In some embodiments the composition that comprises at least one agent that increases oxygen tension and/or redox potential and/or pH in the colon of a subject does not comprise an enzyme that oxidizes ethanol to acetate.

In some embodiments the composition comprises at least 10 mg, at least 25 mg, at least 50 mg, at least 75 mg, or at least 100 mg of at least one peroxide selected from carbamide peroxide and sodium percarbonate; wherein the composition is formulated for oral administration; and wherein the composition is formulated for sustained release. In some embodiments the composition comprises at least 100 mg of carbamide peroxide. In some embodiments the composition comprises at least 100 mg of sodium percarbonate.

In some embodiments the composition comprises at least 10 mg, at least 25 mg, at least 50 mg, at least 75 mg, or at least 100 mg of catalase; wherein the composition is formulated for oral administration; and wherein the composition is formulated for sustained release. In some embodiments the composition comprises at least 100 mg of catalase.

In another aspect this invention provides the use of a composition comprising at least one agent that increases oxygen tension and/or redox potential and/or pH to modify the gut microbiome of a subject. In some embodiments the composition is formulated for delivery of an effective amount of the at least one agent to the small intestine and/or large intestine of a subject following oral administration of the composition to the subject.

In another aspect this invention provides the use of a composition comprising at least one agent that increases oxygen tension and/or redox potential and/or pH to manage the weight of a subject. In some embodiments the composition is formulated for delivery of an effective amount of the at least one agent to the small intestine and/or large intestine of a subject following oral administration of the composition to the subject.

In another aspect this invention provides use of a composition comprising at least one agent that increases oxygen tension and/or redox potential and/or pH to for manufacturing a medicament intended to manage the weight of the subject. In some embodiments the medicament is formulated for delivery of an effective amount of the at least one agent to the small intestine and/or large intestine of a subject following oral administration of the composition to the subject.

DETAILED DESCRIPTION

A. Introduction

Figure 1:
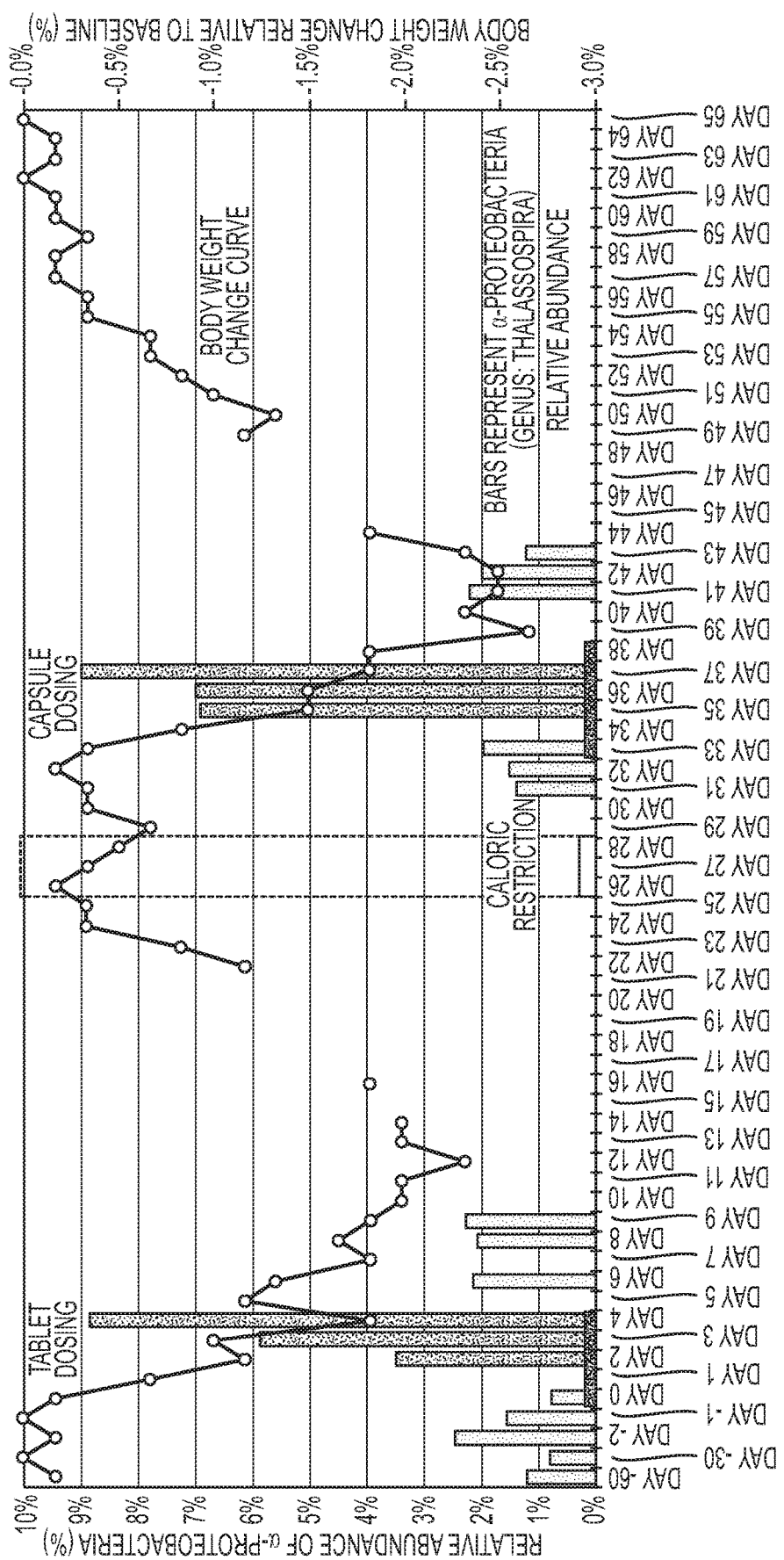
FIG. 1 shows dosing with actives/formulations lead to profound changes in the colon microbiome and body weight. During dosing with tablets and capsules comprising Carbamide peroxide and catalase, α-Proteobacteria increase significantly and body weight loss reaches up to 2.5% over five and six days. In contrast, during caloric restriction body weight dropped only 0.7% over 4 days. These results show that dosing leads to dramatic body weight loss well above and beyond that achieved by simple caloric restriction. Bars indicate relative abundance of *Thalassospira* (genus belonging to α-Proteobacteria). Darker bars correspond to data from samples taken during dosing, whereas lighter bars are data from samples gathered before or after dosing. The black horizontal bars along the x-axis highlight the dosing periods. The days where no body weight measurement was taken were left blank on the plotted body weight curve.

Bariatric surgical procedures such as vertical sleeve gastrectomy (VSG) and Roux-en-Y gastric bypass (RYGB) are the most potent treatments available to produce sustained reductions in body weight and improvements in glucose regulation. While traditionally these effects are attributed to mechanical aspects of these procedures, such as restriction and malabsorption, a growing body of evidence from mouse models of these procedures points to physiological changes that mediate the potent effects of these surgeries. In particular, there are similar changes in gut hormone secretion, bile acid levels, and composition after both of these procedures. Moreover, loss of function of the nuclear bile acid receptor (FXR) greatly diminishes the effects of VSG. Bariatric surgeries are linked to profound changes in the gut microbiome that also mediate at least some of these surgical effects.

Intestinal microorganisms could be contributing to obesity by increasing recovery of energy from the diet and via the impact of microbial metabolites or microbial cell-derived signals on host pathways that regulate energy homoeostasis and lipid metabolism. Several gut microbial diversity surveys in mouse models [Ley R E, Backhed F, Turnbaugh P, Lozupone C A, Knight R D, Gordon J I. "Obesity alters gut microbial ecology." Proc Natl Acad Sci USA 2005; 102: 11070-11075] and humans [Ley R E, Turnbaugh P J, Klein S, Gordon J I. "Microbial ecology: human gut microbes associated with obesity." Nature 2006; 444: 1022-1023; and Turnbaugh P J, Hamady M, Yatsunenko T, Cantarel B L, Duncan A, Ley R E et al. "A core gut microbiome in obese and lean twins." Nature 2009; 457: 480-484] provided evidence that obesity was associated with a decreased proportion of Bacteroidetes and a higher proportion of Firmicutes. These and other data suggest that the gut microbiome plays a regulatory role in obesity and related metabolic conditions.

To date, efforts to modulate the gut microbiome have focussed on strategies to directly add helpful types of bacteria to the gut and/or strategies to reduce harmful types of bacteria in the gut by the use of antibiotics. These approaches are necessarily challenging because added bacteria must compete against endogenous bacteria and antibiotics are often a crude tool that target several types of bacteria at once and there are concerns over antibiotic resistance development. Accordingly, there is a need in the art to provide methods and compositions to modify the gut microbiome in a manner that counters obesity and other metabolic conditions and favors a healthy glucose balance.

U.S. Pat. No. 5,759,539 in the name of David R. Whitmire, issued Jun. 2, 1998 ("Whitmore") suggests that oxygen generating formulations such as catalase and hydrogen peroxide may be useful in combination with enzymes that oxidize ethanol to acetate to treat ethanol overdose and to reduce the amount of ethanol in a subject. Whitmore suggests that oxygen is administered directly with a carrier or that an oxygen generator is administered. In Whitmore the oxygen or oxygen generator is administered together with enzymes that oxidize ethanol to acetate, and these components are delivered to a site where enzymatic conversion of ethanol to acetate is desired. Possible sites include the mucosal membrane of the mouth, nasopharyngeal region, or rectum. This approach would not be useful for modifying the microbiome in the colon for several reasons. For example: first, Whitmore teaches to deliver oxygen and enzymes to sites that would not result in an increase in oxygen in the colon; second, administration to reduce excess ethanol would be for a short term, whereas administration to modify the microbiome in the colon typically occurs over several days or weeks or months in order to realize a therapeutic benefit, such as weight management.

This invention meets needs in the art by providing compositions and systems that may be administered to a subject and that act in the colon of the subject to increase the oxygen tension and/or redox potential and/or pH of the colon, thus changing the conditions in which the gut microbiome of the colon exists. A hypothesis of this invention is that these endogenous changes to the environment of the colon will in turn change the relative abundance of various bacteria present in the colon in a manner that mimics, at least partially, changes to the gut microbiome previously observed in RYGB. Based in part on this discovery, the inventor provides herein methods comprising administering to a subject at least one agent that increases oxygen tension and/or redox potential and/or pH in the colon of a subject. In some embodiments the at least one agent is administered by administering an effective amount of the at least one agent to the small intestine and/or large intestine of the subject. Also provided are methods of treating a subject. In some embodiments the methods comprise providing a subject having or at risk of developing at least one condition selected from a metabolic disease or disorder, metabolic syndrome, and cardiovascular disease; and administering an effective amount to the small intestine and/or large intestine of the subject of at least one agent that increases oxygen tension and/or redox potential and/or pH in the colon of the subject, to thereby treat the at least one condition selected from a metabolic disease or disorder, metabolic syndrome, and cardiovascular disease in the subject. Also provided are compositions. In some embodiments the compositions comprise at least one agent that increases oxygen tension and/or redox potential and/or pH and are formulated for delivery of an effective amount of the at least one agent to the small intestine and/or large intestine of a subject following oral administration of the composition to the subject in order to increase oxygen tension and/or redox potential and/or pH in the colon of the subject. These and other features and aspects of the invention are disclosed more fully herein.

B. Definitions

As used herein, "subject" means any mammal. In some embodiments the subject is a human. In some embodiments the subject is a primate. In some embodiments the subject is a non-human mammal, such as a non-human primate. In some embodiments the subject is a farm animal or livestock. In some embodiments the subject is a pet or companion animal.

As used herein, "administering" means to provide an active agent. For example, a health care practitioner can directly provide an active agent to a subject in the form of a sample, or can indirectly provide an active agent to a subject by providing an oral or written prescription for the active agent. Also, for example, a subject can obtain an active agent by themselves without the involvement of a health care practitioner. When an active agent is administered to a subject it is internalized by the subject and the body of the subject is transformed by the active agent in some way.

As used herein, an "active agent" is a chemical entity that acts to increase the oxygen tension and/or redox potential and/or pH of an aqueous solution that approximates the conditions of a mammalian small intestine or large intestine. Such an agent is variously referred to herein as an "active agent" and/or as an "agent that increases oxygen tension and/or redox potential and/or pH in the colon of the subject to thereby manage the weight of the subject."

As used herein, an "agent that increases oxygen tension and/or redox potential and/or pH in the colon of the subject to thereby manage the weight of the subject" is an agent that has at least one property selected from (1) increases the oxygen tension of a solution of phosphate buffered saline (PBS), (2) increases redox potential of PBS, and (3) increases pH of PBS.

Whether an agent increases the oxygen tension of PBS is measured in the following assay. A solution of phosphate buffered saline is provided. The PBS is 0.01 M phosphate buffered saline (NaCl 0.138 M; KCl—0.0027 M); pH 7.4, at 25° C. The test agent is added to the PBS in different concentrations ranging from 1 nano molar to 1 molar. The solution is then incubated at 37 C, and stirred at 20 rpm. Across titration within this concentration range, if the test agent increases oxygen tension by at least a predetermined cutoff, then the test agent is identified as an active agent. Oxygen concentration is then measured using a commercially available dissolved oxygen meter. In some embodiments a test agent is identified as an active agent if the test agent increases the oxygen tension by at least 0.01 mg/L. In some embodiments a test agent is identified as an active agent if the test agent increases the oxygen tension by at least 0.02 mg/L. In some embodiments a test agent is identified as an active agent if the test agent increases the oxygen tension by at least 0.05 mg/L. In some embodiments a test agent is identified as an active agent if the test agent increases the oxygen tension by at least 0.10 mg/L. In some embodiments a test agent is identified as an active agent if the test agent increases the oxygen tension by at least 0.20 mg/L. In a preferred embodiment, the active agent increases the oxygen tension by at least 0.10 mg/L.

Whether an agent increases the redox potential of PBS is measured in the following assay. A solution of phosphate buffered saline is provided. The PBS is 0.01 M phosphate buffered saline (NaCl 0.138 M; KCl—0.0027 M); pH 7.4, at 25° C. The test agent is added to the PBS in different concentrations ranging from 1 nano molar to 1 molar. The solution is then incubated at 37 C, and stirred at 20 rpm. Across titration within this concentration range, if the test agent increases redox potential by at least a predetermined cutoff, then the test agent is identified as an active agent. Redox potential is then measured using a commercially available redox meter. In some embodiments a test agent is identified as an active agent if the test agent increases the redox potential by at least 0.1 mV. In some embodiments a test agent is identified as an active agent if the test agent increases the redox potential by at least 0.5 mV. In some embodiments a test agent is identified as an active agent if the test agent increases the redox potential by at least 1.0 mV. In some embodiments a test agent is identified as an active agent if the test agent increases the redox potential by at least 5.0 mV. In some embodiments a test agent is identified as an active agent if the test agent increases the redox potential by at least 10.0 mV. In some embodiments a test agent is identified as an active agent if the test agent increases the redox potential by at least 20.0 mV. In a preferred embodiment the active agent increases the redox potential by at least 10.0 mV.

Whether an agent increases the pH of PBS is measured in the following assay. A solution of phosphate buffered saline is provided. The PBS is 0.01 M phosphate buffered saline (NaCl 0.138 M; KCl—0.0027 M); pH 7.4, at 25° C. The test agent is added to the PBS in different concentrations ranging from 1 nano molar to 1 molar. The solution is then incubated at 37 C, and stirred at 20 rpm. Across titration within this concentration range, if the test agent increases redox potential by at least a predetermined cutoff, then the test agent is identified as an active agent. The pH of the solution is then measured using a commercially available pH meter. In some embodiments a test agent is identified as an active agent if the test agent increases the pH by at least 0.01 units. In some embodiments a test agent is identified as an active agent if the test agent increases the pH by at least 0.02 units. In some embodiments a test agent is identified as an active agent if the test agent increases the pH by at least 0.05 units. In some embodiments a test agent is identified as an active agent if the test agent increases the pH by at least 0.10 units. In some embodiments a test agent is identified as an active agent if the test agent increases the pH by at least 0.20 units. In a preferred embodiment the active agent increases the pH by at least 0.10 units.

A skilled artisan will appreciate that a single agent may have any two of these three activities or may have all three. That is, that a single agent may increase oxygen tension and also increase redox potential; or that a single agent may increase oxygen tension and also increase pH; or that a single agent may increase redox potential and also increase pH; or that a single agent may increase oxygen tension, and increase redox potential, and increase pH. Thus, in some instances an agent that is identified herein as an agent that increases one of oxygen tension, redox potential, and pH, that agent may also be an agent that increases at least one additional feature selected from oxygen tension, redox potential, and pH. A non-limiting example is sodium percarbonate, which increases all of oxygen tension, redox potential and pH.

While exemplary active agents are disclosed herein the disclosed agents are not intended to be limiting.

As used herein "condition" encompasses a disease, condition, or disorder.

The term "effective amount" refers to the amount of active agent that elicits a biological or medicinal response in a subject, including in a tissue or system of the subject, and that is being sought by a researcher, veterinarian, medical doctor, nutritionist, or other clinician or caregiver or by a subject, which includes one or more of the following:

(1) Preventing the condition, for example, preventing a condition in a subject that may be predisposed to the condition but does not yet experience or display the pathology or symptomatology of the condition;

(2) Inhibiting the condition, for example, inhibiting a condition in an individual that is experiencing or displaying the pathology or symptomatology of the condition (i.e., arresting further development of the pathology and/or symptomatology); and (3) Ameliorating the condition, for example, ameliorating a condition in an individual that is experiencing or displaying the pathology or symptomatology of the condition, (i.e., reversing the pathology and/or symptomatology).

As used herein, an "increase in the relative abundance" of a group of bacteria in the gut microbiota of a subject means an increase in the proportion of bacterial cells belonging to that group among the total bacterial cells measured in an assay that samples the bacteria in the microbiota of the gut of a subject. Relative abundance is defined as the number of bacteria belonging to that group divided by the total number of bacteria measured. For example, if 20% of taxonomic markers in the gut microbiota of a subject obtained by 16S rRNA sequencing belong to a given group of bacteria, the relative abundance of this group of bacteria is scored as 20%. In other words, there would be 20 bacteria belonging to this group in every 100 bacteria measured by sequencing or another equivalent method. Maximum relative abundance is 100% and the minimum is 0%.

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. As used herein, "overweight" is defined as a BMI in the range 25-30 $kg/m^2$, and "obesity" or "obese" as a BMI greater than 30 $kg/m^2$.

As used herein the term "metabolic disorder", refers to disorders, diseases, and conditions that are caused or characterized by abnormal weight gain, energy use or consumption, altered responses to ingested or endogenous nutrients, energy sources, hormones or other signaling molecules within the body or altered metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 or other neurotransmitters or regulatory proteins in the brain) or the like. Some non-limiting examples can be obesity, diabetes, including type II diabetes, insulin-deficiency, insulin-resistance, insulin-resistance related disorders, glucose intolerance, syndrome X, inflammatory and immune disorders, osteoarthritis, dyslipidemia, metabolic syndrome, non-alcoholic fatty liver, abnormal lipid metabolism, cancer, neurodegenerative disorders, sleep apnea, hypertension, high cholesterol, atherogenic dyslipidemia, hyperlipidemic conditions such as atherosclerosis, hypercholesterolemia, and other coronary artery diseases in mammals, and other disorders of metabolism. In some embodiments the metabolic disorder is diagnosed by a physician.

As used herein the term "treat," "treating" or "treatment" refers to the administration of therapy to an individual who already manifests at least one symptom of a condition, or who has previously manifested at least one symptom of a condition, or who is identified as at risk of developing a condition. For example, "treating" can include alleviating, abating or ameliorating a condition's symptoms, preventing additional symptoms, ameliorating or preventing the underlying metabolic causes of symptoms, inhibiting the condition, e.g., arresting the development of the condition, relieving the condition, causing regression of the condition, relieving a second condition caused by the first condition, or stopping the symptoms of the condition either prophylacticly and/or therapeutically. For example, the term "treating" in reference to a condition includes a reduction in severity of one or more symptoms associated with a particular condition. Therefore, treating a condition does not necessarily mean a reduction in severity of all symptoms associated with a condition and does not necessarily mean a complete reduction in the severity of one or more symptoms associated with a condition. For example, a method for treatment of cardiovascular disease can result in a reduction in blood pressure; however, the reduction in blood pressure does not need to be enough such that the individual has a fully normal cardiovascular health. It has been shown that even modest decreases in weight or related parameters such as BMI, waist circumference and percent body fat, can result in improvement of health, for example, lower blood pressure, improved blood lipid profiles, or a reduction in sleep apnea. For example, the term "treating" also includes reducing the rate of increase in severity in a condition already manifested in a subject and/or reducing the rate of occurrence of new related conditions in the subject.

As used herein, "providing a subject having or at risk of developing at least one condition" refers to a judgment made by a researcher, veterinarian, medical doctor, nutritionist, or other clinician or caregiver, or by a subject, that a subject requires or will benefit or may benefit from treatment.

As used herein, "weight management" means at least one of weight loss, maintenance of weight, maintenance of weight loss (also called weight maintenance herein), controlling weight gain, body mass index (BMI) reduction, maintenance of BMI, maintenance of BMI reduction, and controlling BMI gain in a subject. In some embodiments the subject is overweight or obese. In some embodiments the subject has at least one weight-related condition. In some embodiments the at least one weight-related condition is selected from a metabolic disease or disorder, metabolic syndrome, and cardiovascular disease. In some embodiments the at least one weight-related condition is selected from hypertension, dyslipidemia, and type 2 diabetes. In some embodiments at least one symptom of the at least one weight-related condition is ameliorated. For example, weight management for an individual who is overweight or obese can mean losing weight with the goal of keeping weight in a healthier range. Also, for example, weight management for an individual who is overweight or obese can include losing body fat (reduction in BMI) or circumference around the waist with or without the loss of body weight. Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weigh gained after weight loss, controlling weight gain after weight loss or slowing the rate of weight gain after weight loss. As used herein, "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein. In some embodiments weight management comprises decreasing appetite. In some embodiments weight management comprises decreasing hunger.

As used herein, "aerobic bacteria" are bacteria that need oxygen to grow. Included within the aerobic bacteria are microaerophiles, which are bacteria that require oxygen for energy production but are harmed by atmospheric concentrations of oxygen.

As used herein, "facultative anaerobes" are bacteria or other microorganisms such as fungi that make ATP by aerobic respiration if oxygen is present, but are capable of switching to fermentation or anaerobic respiration if oxygen is absent.

As used herein, "sustained release" refers to an oral dosage form containing a composition comprising at least one active agent and at least one release rate modifier. The oral dosage form is formulated so that the at least one release rate modifier reduces the rate of release of the at least one active agent in comparison to a similar formulation that does not contain at least one release rate modifier. The oral dosage form may also be referred to as "formulated for sustained release" or as a "sustained release formulation." The oral dosage form may alternatively be referred to as "formulated for extended release" or as an "extended release formulation," making reference to the reduced rate of release that extends the period of release.

In some embodiments the period of release of active agent from a sustained release formulation is increased in comparison to a comparable formulation that does not comprise the at least one release rate modifier by a period of 0.5 hours, 1 hour, 2 hours, 3 hours, 4 hours, 5 hours, 6 hours, 12 hours, or 24 hours. In some embodiments the period of release of active agent from a sustained release formulation is increased in comparison to a comparable formulation that does not comprise the at least one release rate modifier by a period of at least 0.5 hours, at least 1 hour, at least 2 hours, at least 3 hours, at least 4 hours, at least 5 hours, at least 6 hours, at least 12 hours, or at least 24 hours.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination.

C. Agents that Increase Oxygen Tension and/or Redox Potential and/or pH

A skilled artisan will appreciate that any agent that increases oxygen tension and/or redox potential and/or pH (i.e., any active agent) may be used in the methods, compositions, and systems of this invention.

Agents that increase oxygen tension include agents that carry oxygen to the large intestine and agents that increase production of oxygen from stores in the gut and/or from added oxygen stores. Any oxygen carrier may be used to increase oxygen tension, including a molecule that reacts to release oxygen. For example, in some embodiments the at least one agent comprises a peroxide functional group. A peroxide functional group is a group comprising or consisting of an O—O single bond or the peroxide anion. In contrast to oxide ions, the oxygen atoms in the peroxide ion have an oxidation state of −1. The simplest stable peroxide is hydrogen peroxide. In some embodiments at least one agent is hydrogen peroxide. In some embodiments the at least one peroxide is an organic peroxide. In some embodiments the at least one peroxide is an organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments the at least one agent is an inorganic peroxide. In some embodiments the at least one agent is an inorganic peroxide selected from Ammonium persulfate, Calcium peroxide, Magnesium peroxide, Potassium persulfate, Sodium peroxide, Lithium peroxide, Barium peroxide and Sodium perborate. In some embodiments the at least one agent is carbamide peroxide. In some embodiments the at least one agent is Sodium percarbonate.

In some embodiments, sodium percarbonate is formulated as granules. In some embodiments sodium percarbonate granules are coated with protective coating or is chosen from commercially available caoted particles such as FB 400C, FB 700C, OXYPER (Solvay), Provox-C (OCI corporation), ECOX-C (Kemira). The coating can be based on sodium carbonate, sodium chloride and sodium metasilicate or combinations thereof. Coating may be used to improve the stability of the final product.

In some embodiments, agents that increase oxygen tension are selected from reactive oxygen species (ROS) other than peroxides. Reactive oxygen species in the presence of catalysts or corresponding enzymes of mammalian or bacteria can be converted or decomposed into hydrogen peroxide or oxygen. In some embodiments one such agent is selected from superoxides, dioxygenyls, ozones and ozonides. In some embodiments one such agent is selected from singlet oxygen, hydroxyl radical, superoxide, nitric oxide, ozone, peroxyl, lipid peroxyl, hypochloric acid. In some embodiments, agents that increase oxygen tension are selected from reactive nitrogen species such as nitric oxide which can decompose into nitrogen and oxygen gas. In some embodiments, such agents are selected from nitrous oxide, peroxynitrite, peroxynitrous acid, nitrosoperoxycarbonate, dinitrogen trioxide, nitroxyl anion, nitrogen dioxide, nitrous acid, nitrousyl cation, nitryl chloride, nitrosonium cation, higher oxides of nitrogen, S-nitrosothiols, and dinitrosyl iron complexes.

In some embodiments, the agent that increases oxygen tension is an oxygen carrier. In some embodiments the oxygen carrier is a perfluorocarbon. In some embodiments the perfluorocarbon is selected from perfluorodecalin, bromoperfluoro-n-octane (perfluorobron), dichloroperfluoro-n-octane, triperfluoropropylamine. Oxygen gas may be dissolved in perfluorocarbon fluids and delivered to the colon with enteric coating or timed release technology. In some embodiments, the oxygen carrier is microbubble preparation of oxygen gas created by encapsulation of oxygen gas into polymetric bubbles or lipid based of emulsion of air/oxygen gas. In some embodiments, oxygen gas may be directly delivered to the gut to increase oxygen tension. In some embodiments, oxygen gas is encapsulated into entericly coated capsules and delivered to increase oxygen tension in the colon using pH or timed release formulations.

Agents that increase production of oxygen from stores in the gut and/or from added oxygen stores include any enzyme that catalyzes a chemical reaction that produces oxygen. An example is catalase, a common enzyme found in nearly all living organisms exposed to oxygen. Catalase catalyzes the decomposition of hydrogen peroxide to water and oxygen. Accordingly, in some embodiments the agent that increases oxygen tension is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In some embodiments the catalase is a plant catalase such as potato catalase. In some embodiments the catalase is liver catalase, such as bovine catalase. In some embodiments the catalase is blood catalase. In some embodiments the catalase is bacterial catalase. In some embodiments the catalase is obtained from *Micrococcus* genus. In some embodiments the catalase is fungal catalase. In some embodiments the catalase is obtained from *Aspergillus niger*. In some embodiments the catalase is recombinant. In such embodiments catalase increases oxygen tension by increasing the rate of decomposition of endogenous hydrogen peroxide to water and oxygen. In other embodiments catalase and hydrogen peroxide are used together.

Additional examples of agents that catalyze a chemical reaction that produces oxygen include additional peroxide catalysts. In some embodiments the peroxide catalyst is an inorganic peroxide catalyst. In some embodiments the inorganic peroxide catalyst is selected from manganese(IV) oxide (manganese dioxide, MnO2), lead(IV) oxide (lead dioxide, PbO2), iron(III) oxide (red iron oxide, Fe2O3), silver nitrate and potassium iodide. In some embodiments the peroxide catalyst is an organic peroxide catalyst. In some embodiments the organic peroxide catalyst is selected from blood and bacteria. In some embodiments the organic peroxide catalyst is a peroxidase. Peroxidases are a large family of enzymes that typically catalyze a reaction of the form: ROOR'+electron donor (2 e−)+2H+→ROH+R'OH In some embodiments the at least one agent is an agent that increases pH. Non-limiting examples of agents that increase pH include bicarbonate salts, carbonate salts, bases, and buffers. In some embodiments the agent that increases pH is bicarbonate. Bicarbonate acts physiologically to regulate pH in the small intestine. It is released from the pancreas in response to the hormone secretin to neutralize the acidic chyme entering the duodenum from the stomach. In some embodiments the at least one agent is bicarbonate. In some embodiments the at least one agent comprises a bicarbonate group. Examples include bicarbonate salts, such as sodium bicarbonate, potassium bicarbonate, caesium bicarbonate, magnesium bicarbonate, calcium bicarbonate, ammonium bicarbonate. In some embodiments the at least one agent is a bicarbonate salt. In some embodiments the bicarbonate salt is selected from Sodium Hydrogen Carbonate, Beryllium Hydrogen Carbonate, Magnesium Hydrogen Carbonate, Calcium Hydrogen Carbonate, Potassium Hydrogen Carbonate, Barium Hydrogen Carbonate, Copper(II) Hydrogen Carbonate, Iron(III) Hydrogen Carbonate, Aluminum Hydrogen Carbonate, Lithium Hydrogen Carbonate, Lead (II) Hydrogen Carbonate, Tin(IV) Hydrogen Carbonate, Iron(II) Hydrogen Carbonate, Ammonium Hydrogen Carbonate, Mercury(II) Hydrogen Carbonate, Lead(IV) Hydrogen Carbonate, Manganese(II) Hydrogen Carbonate, Cesium Hydrogen Carbonate, Silver Hydrogen Carbonate, Tin Hydrogen Carbonate, Copper(I) Hydrogen Carbonate, Zinc Hydrogen Carbonate, Rubidium Hydrogen Carbonate, Nickel(II) Hydrogen Carbonate, Cadmium Hydrogen Carbonate, Strontium(II) Hydrogen Carbonate, Mercury(I) Hydrogen Carbonate, Chromium(II) Hydrogen Carbonate, Gold(III) Hydrogen Carbonate, Cobalt(II) Hydrogen Carbonate, and Cobalt(III) Hydrogen Carbonate.

In some embodiments the at least one agent is a carbonate. In some embodiments the carbonate is a carbonate salt. In some embodiments the carbonate salt is selected from Sodium Carbonate, Sodium percarbonate (Sodium Carbonate Peroxide), Calcium Carbonate, Cobalt(III) Carbonate, Copper(I) Carbonate, Potassium Carbonate, Ammonium Carbonate, Chromium(III) Carbonate, Iron(III) Carbonate, Aluminum Carbonate, Tin(IV) Carbonate, Lead(IV) Carbonate, Magnesium Carbonate, Iron(II) Carbonate, Tin(II) Carbonate, Chromium(VI) Carbonate, Silver(I) Carbonate, Titanium(IV) Carbonate, Vanadium(III) Carbonate, Copper (II) Carbonate, Zinc(II) Carbonate, Lithium Carbonate (Lithium Salt), Cobalt(II) Carbonate, Nickel(III) Carbonate, Sodium Carbonate Decahydrate, Mercury(I) Carbonate, Barium Carbonate, Lead Carbonate, Mercury(II) Carbonate, Chromium(II) Carbonate, Strontium Carbonate, and Vanadium(V) Carbonate.

In some embodiments the at least one agent is a base. In some embodiments the base is a strong base, such as a base selected from Sodium Hydroxide, Aluminum Hydroxide, Calcium Hydroxide, Barium Hydroxide, Magnesium Hydroxide, Iron(III) Hydroxide, Ammonium Hydroxide, Potassium Hydroxide, Chromium(III) Hydroxide, Zinc Hydroxide, Lead(II) Hydroxide, Platinum(IV) Hydroxide, Vanadium(V) Hydroxide, Beryllium Hydroxide, Copper(II) Hydroxide, Lead(IV) Hydroxide, Vanadium(III) Hydroxide, Iron(II) Hydroxide, Nickel(II) Hydroxide, Tin(IV) Hydroxide, Silver Hydroxide, Strontium Hydroxide, Tin(II) Hydroxide, Lithium Hydroxide, Manganese(II) Hydroxide, Chromium(II) Hydroxide, Nickel Oxo-hydroxide, Mercury (II) Hydroxide, Cadmium Hydroxide, and Copper(I) Hydroxide, Manganese(IV) Hydroxide. In some embodiments the base is a superbase, such as a base selected from Butyl lithium (n-C4H9Li), Lithium diisopropylamide (LDA) [(CH3)2CH]2Nli, Lithium diethylamide (LDEA) (C2H5)2Nli, Sodium amide (NaNH2), Sodium hydride (NaH), and Lithium bis(trimethylsilyl)amide [(CH3) 3Si2NLi. In some embodiments the base is an organic base, such as a base selected from Amines, Nitrogen-containing heterocyclic compounds, Urea, Ammonia, pyridine, methyl amine, imidazole, benzimidazole, histidine, and andphosphazene. In some embodiments the agent is a weak base.

In some embodiments the agent is a buffer, such as a buffer selected from MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and CABS. In some embodiments the buffer is a Citric Acid—Na2HPO4 Buffer Solution. In some embodiments the buffer is a Na2HPO4—NaH2PO4 Buffer Solution. In some embodiments the buffer is a Sodium Carbonate—Sodium Bicarbonate Buffer Solution. In some embodiments the buffer is a Imidazole (glyoxaline)—HCl buffer solution.

In some embodiments the at least one agent is an agent that increases redox potential. In some embodiments, the agent that increases redox potential is an oxidizing agent. In some embodiments, the oxidizing agent is selected from compounds containing halogens such as Fluorine (F), Chlorine (Cl), Bromine (Br), Iodine (I), and Astatine (At). In some embodiments, the oxidizing agent is selected from Aluminium nitrate, Ammonium chlorate, Ammonium dichromate, Ammonium nitrate, Ammonium nitrite, Ammonium perchlorate, Ammonium permanganate, Ammonium persulfate, Antimony pentachloride, Barium chlorate, Barium chromate, Barium manganate, Barium nitrate, Barium perchlorate, Barium peroxide, Benedict's reagent, Bismuth pentafluoride, Bromic acid, Bromine, Bromine monochloride, Bromine pentafluoride, Bromine trifluoride, Bromous acid, Cadmium nitrate, Caesium chromate, Caesium nitrate, Caesium perchlorate, Calcium bromate, Calcium chlorate, Calcium chromate, Calcium hypochlorite, Calcium iodate, Calcium nitrate, Calcium permanganate, Calcium peroxide, Ceric ammonium nitrate, Cerium(III) methanesulfonate, Chloric acid, Chlorine, Chlorine monofluoride, Chlorine nitrate, Chlorine pentafluoride, Chlorine trifluoride, Meta-Chloroperoxybenzoic acid, N-Chlorosuccinimide, Chlorous acid, Chromate and dichromate, Chromic acid, Chromium nitrate, Chromyl chloride, Chromyl fluoride, Cobalt(II) chlorate, Cobalt(II) nitrate, Collins reagent, Copper(II) acetate, Copper(II) hydroxide, Copper (II) nitrate, Copper(II) perchlorate, Dess-Martin periodinane, Dichlorine heptoxide, Dinitrogen tetroxide, Dioxygen difluoride, Fehling's solution, Fenton's reagent, Fluorine, Fluorine perchlorate, Gadolinium(III) nitrate, Hill reagent, Hydrazine nitrate, Hydrogen peroxide, Hydrogen peroxide-urea, Hypobromous acid, Hypochlorous acid, Hypoiodous acid, Iodic acid, Iodine, Iodine heptafluoride, Iodine monochloride, Iodine pentafluoride, Iodine pentoxide, Iodine trichloride-Iodobenzene dichloride Iodous acid, Iron(III)

chromate, Iron(III) nitrate, Jones reagent, Lead(II) chromate, Lead(II) nitrate, Lead(IV) acetate-Lithium chlorate, Lithium hypochlorite, Lithium nitrate, Lithium nitrite, Lithium perchlorate, Lithium peroxide, Magnesium monoperoxyphthalate, Magnesium nitrate, Magnesium perchlorate, Manganese(III) acetate, Mercury(II) nitrate, Nickel chromate, Nickel(II) nitrate, Nitronium perchlorate, Nitrosyl-O-hydroxide, Nitrous acid, Osmium tetroxide, Oxygen, Oxygen difluoride, Ozone, Palladium(II) nitrate, Perbromic acid, Perchlorate, Perchloric acid, Performic acid, Periodic acid, Permanganic acid, Peroxy acid, Peroxymonosulfuric acid, Potassium bromate, Potassium chromate, Potassium dichromate, Potassium hypochlorite, Potassium iodate, Potassium nitrate, Potassium nitrite, Potassium perchlorate, Potassium periodate, Potassium permanganate, Potassium peroxide, Potassium peroxymonosulfate, Potassium persulfate, Potassium superoxide, Potassium tetraperoxochromate(V), Potassium trioxochlorochromate, Pyridinium chlorochromate, Rubidium nitrate, Rubidium perchlorate, Scandium nitrate, Selenic acid Selenium hexasulfide, Selenium trioxide, Selenous acid, Silver bromate, Silver chlorate, Silver chromate, Silver dichromate, Silver iodate, Silver nitrate, Silver perchlorate, Singlet oxygen, Sodium bromate, Sodium chlorate, Sodium chlorite, Sodium chromate, Sodium dichromate, Sodium hypochlorite, Sodium fluoride, Sodium iodate, Sodium nitrate, Sodium nitrite, Sodium perborate, Sodium percarbonate, Sodium perchlorate, Sodium periodate, Sodium permanganate, Sodium peroxide, Sodium persulfate, Sodium superoxide, Stannous fluoride, Strontium bromate, Strontium chlorate, Strontium nitrate, Strontium peroxide, Sulfuric acid, Superoxidant, Telluric acid, Tetrapropylammonium perruthenate, Thallium(III) nitrate, Tollens' reagent, Trinitroethylorthocarbonate, Trinitroethylorthoformate, Uranyl nitrate, Uranyl peroxide, Zinc chlorate, Zinc nitrate, and Zinc peroxide. In some embodiments, the agent that increases redox potential is a fluoride containing compound. In some embodiments, the agent that increases redox potential is selected from Sodium fluoride, Sodium monofluorophosphate and Stennous fluoride.

D. Oral Dosage Forms

Compositions comprising the at least one active agent are also provided herein and may be administered to a subject in the methods of the invention. In some embodiments the active agent is delivered using a dosage form that protects the active agent until it reaches the distal ileum so that the active agent is then released in the distal ileum or the distal ileum and the large intestine, resulting in addition of oxygen to the large intestine in an amount sufficient to modify the microbiome of the large intestine. In some embodiments the active agent is delivered using a dosage form that protects the active agent until it reaches the large intestine so that the active agent is then released in the large intestine, resulting in addition of oxygen to the large intestine in an amount sufficient to modify the microbiome of the large intestine. In some embodiments the active agent is delivered using a dosage form that protects the active agent until it reaches the distal ileum and/or large intestine and so that it is then released over a period of at lease three hours, at least six hours, or at least twelve hours to thereby modify the microbiome of the large intestine for a period of time.

The compositions may be provided in the form of tablets, troches, pills, capsules, powders, liquids, and the like, may contain a solid carrier binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, or saccharin, for example. When provided as a capsule, it may contain, in addition to materials of the above type, a liquid carrier such as a fatty oil. Various other materials may be present as coatings or to modify the physical form of the dosage unit. For instance, tablets may be coated with shellac, sugar or both.

Liquid carriers may be used in preparing liquid dosage forms such as solutions, suspensions, dispersions, emulsions, syrups, elixirs and pressurized compositions. The active agent can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g., cellulose derivatives, such as, sodium carboxymethyl cellulose solution); alcohols, including monohydric alcohols such as ethanol and polyhydric alcohols such as glycols and their derivatives; lethicins, and oils such as fractionated coconut oil and arachis oil.

Compositions comprising the at least one active agent may be administered to the small intestine and/or large intestine of the subject by administering an oral dosage form comprising the at least one agent to the subject. In several embodiments the active agent is administered to the small intestine and/or large intestine of the subject. In order to efficiently achieve this result it is often preferred that the active agent pass through the stomach without interacting with the acidic aqueous environment of the stomach. This may be achieved using any suitable method. Typically it is achieved by administering an oral dosage form comprising the at least one active agent protected by an enteric coating. For example, the composition may be formulated such that the composition is coated with an enteric coating that protects the composition from the acidic environment of the stomach and delays release of the active agent until the composition has passed through the stomach and into the duodenum, jejunum, ileum, and/or colon. Any conventional enteric coating may be used.

The oral dosage forms of the invention typically comprise a core comprising the at least one active agent (e.g., containing a composition comprising the at least one active agent), an enteric coating, and optionally a release rate modifier. In some embodiments that include a release rate modifier one or more cores is dispersed in the release rate modifier. The release rate modifier and core(s) are encased in the enteric coating layer. In some embodiments, release rate modifier is a polymer that is degraded by the gut microbiota selected from azopolymers, starches, dextrans, mucopolysaccharides (e.g. inulin, guar gum, pectin, chondroitin sulfate, alginic acid). In some embodiments colonic delivery is achieved with the use of other coatings than enteric coating. In some embodiments, colonic delivery coating is an erosion based, pH independent coating whose erosion time is long enough to release actives in the distal ileum or colon. In some embodiments, colonic delivery coating is a gut microbiota activated coating such as azopolymer or starch based coatings. In some embodiments additional coating layers are used together with the enteric coating, such as pH independent erosion based coatings to increase release time or gut microbiota activated coatings such as azopolymer or starch based coatings for colonic delivery. In some embodiments, no enteric coating is used but a release rate modifier such as a polymer matrix system is used to delay the release of actives until distal ileum or colon. In some embodiments, the core of the formulation includes solid powder of an anionic copolymer matrix such as Eudagrit S 100 for pH dependent sustained release of actives in distal ileum and colon.

Enteric film coatings are applied to oral dosage forms to delay the release of active ingredients until the dosage form has passed through the acidic environment of the stomach and has reached the near-neutral environment of the proximal small intestine. The physical chemical environment of the stomach and gastric physiology are highly variable, subject to multiple factors such as disease state, medication, age, and eating. For example in the fasted state stomach, the pH is less than 2 in healthy individuals, and gastric emptying occurs approximately every 30 minutes. However in the fed state (immediately after a meal), gastric emptying is delayed for 2 to 4 hours and gastric pH can be as high as pH 4.

For these reasons, in some embodiments the enteric coating system is flexible. In some embodiments the enterically coated dosage form is recommended to be taken on an empty stomach. In that case the enteric coating will have to be resistant to the acidic stomach environment for a relatively short time and would not be expected to be subjected to strong mechanical attrition in the stomach. On the other hand, to allow for possible ingestion in the fed state, or where subsequent release from the intestine is not intended to be immediate, the coating will typically be sufficiently robust to withstand prolonged attrition in the stomach or to generally release more slowly in the alkaline environment.

There is a long history of use of enteric coatings on tablets and smaller multi-particulate dosage forms in the pharmaceutical industry. Generally polymers with acidic functional groups are chosen for enteric coatings. In the acid environment of the stomach these acid groups of the polymers are un-ionized, thus rendering the polymer water insoluble. However in the more neutral and alkaline pH of the intestine (pH 6.8-7.2), the functional groups ionize and the polymer film coating becomes water soluble.

Examples of enteric film coatings that may be used in embodiments of the invention include methacrylic acid copolymers, polyvinyl acetate phthalate, cellulose acetate phthalate, hydroxypropyl methylcellulose phthalate and hydroxypropyl methylcellulose acetylsuccinate. In some embodiments these water soluble coatings are applied from organic solvent based coating solutions. In some embodiments an aqueous based dispersion and/or pseudo-latex system of comprising at least one of the above polymers is used. In some embodiments the polymers used for enteric coating are found in the Food Chemicals Codex (FCC), have direct food additive status, and/or have generally regarded as safe (GRAS) status. In some embodiments, commercially available enteric coatings such as EUDAGRIT™ coatings (Evonik Industries) are used. In some embodiments, EUDAGRIT™ enteric coatings for dissolution at specific pH levels such as pH above 5.5, pH above 5.6, pH above 6.0, pH above 6.8 (Eudragit®FS 30D) and pH above 7.0 (Eudragit®S100) are used. In some embodiments, the core of the formulation includes solid powder of an anionic copolymer matrix based on methacrylic acid and methyl methacrylate such as Eudagrit S 100 in order to achieve pH dependent sustained release of actives in distal ileum and colon.

Several strategies may be used to provide a food grade enteric coating for the oral dosage form of the invention. For example, an aqueous ethylcellulose (EC) based pseudo-latex may be used in conjunction with sodium alginate. For example, in some embodiments the Nutrateric™ nutritional enteric coating system marketed by Colorcon Inc. of Westpoint, Pa. is used. This coating is supplied as a two component system in the form of an aqueous ammoniated EC dispersion with 25% solids and a separate container of sodium alginate in powder form. To prepare the final coating solution, the sodium alginate is first dispersed and dissolved in water for 60 minutes and EC dispersion is then added to the alginate solution, ensuring that the amount of water used is appropriate to achieve a final recommended dispersed solids concentration of 10% by weight.

An alternative approach is the use of shellac on its own or in combination with other additives. Shellac is a natural, food approved, resinous material obtained from the exudate of the insect *Karria lacca*. It is a complex mixture of materials. The two main components with enteric properties being shelloic and aleuritic acid. Shellac may be used in the form of organic solvent based solutions. To obviate the use of solvents, neutralized aqueous shellac solutions are commercially available. EP 1 579 771 A1 describes a water based shellac dispersion which comprises shellac, a basic amino acid, a basic phosphate and water. The basic amino acid being selected from the group consisting of arginine, lysine and ornithine. Several forms of aqueous ammoniated shellac dispersions are also commercially available, for example Certiseal® FC 300A film coat product, manufactured by Mantrose Haeuser, a subsidiary of RPM Corporation. Esterification of the shellac is also limited in these systems as shellac forms a salt with the ammonia or protonated amino acid.

In another approach an enteric coating formulation in the form of a spray solution or suspension is used. This system may comprise shellac in aqueous salt form and sodium alginate, preferably in equal concentrations. An aqueous solution of an alkali salt of shellac is prepared by first dissolving the shellac in 55° C. hot water, then adding 10% ammonium hydrogen carbonate and heating to 60° C. and stirring for 30 minutes. Separately, a sodium alginate solution is prepared and the two solutions are then blended together. The system, when coated onto a dosage form rapidly disintegrates in simulated intestinal fluid (pH 6.8).

The above approaches describe enteric coatings composed of food approved ingredients, which are either pH sensitive or more time dependant in terms of their delayed release mechanism. However, all these systems require multiple, time consuming preparation steps, often requiring two separate solutions to be made with additional dilution requirements and which increases the potential for error. Alternately, the systems require the use of pre-made dispersions of EC or shellac, which then require further dilution and blending steps thereby adding cost, complexity and/or time to the manufacturing process.

In the case of pre-made aqueous dispersions, a further cost is incurred due to the need to store and ship dispersions which contain the added bulk of water. Additionally, these pre-made aqueous dispersions require additional precautions to be taken to control microbial contamination and to minimize any physical and/or chemical instability of the dispersion.

The present invention relates to a formulation in powder form useful for producing a sprayable dispersion for enteric coating. The powder formulation comprising a food grade shellac, a non-ammonium alkali salt, and optionally a water-miscible polymer. The powder formulation when dispersed in water is capable of producing a sprayable dispersion for enteric coating. This coating at 15% solids in water has a viscosity of below 500 cps at about 25° C. when measured with a Brookfield LTV viscometer with a #2 spindle at 100 rpm.

In some embodiments the enteric coating comprises food grade shellac, optionally blended with other food grade ingredients. The coating is produced starting from a powder form dispersed in water. In addition to shellac, the coating may comprise a non-ammonium alkali salt, which may be selected from sodium bicarbonate, sodium carbonate, potassium carbonate, potassium bicarbonate, calcium hydroxide, calcium bicarbonate and calcium carbonate, and optionally a water-miscible polymer. The water-miscible polymer may be a polymer which is "food grade", dissolvable or dispersible in water, with no discernable phase separation from the aqueous phase. The water-miscible polymers that may be used include alginate salt, alginic acid, proteins (e.g. wheat, soybean or corn), methylcellulose (MC), hydroxypropylcellulose (HPC), hydroxypropylmethylcellulose (HPMC), carboxymethyl cellulose (CMC), pectin, carrageenan, guar gum, locust bean gum, xanthan gum, gellan gum, arabic gum, etc. In some embodiments the water-miscible polymer is selected from anionic polymers such as sodium carboxymethyl cellulose (CMC), sodium alginate or pectin. The coating may optionally comprise one or more plasticizers chosen from glycerine, mineral oil, triacetin, polyethylene glycol, glyceryl monostearate, acetylated monoglyceride, glyceryl tricaprylate/caprate and polysorbate. Optionally, the coating may further comprise pigments, and/or detackifiers such as titanium dioxide, talc, iron oxide glyceryl monostearate. Additional components such as natural colors, various carbohydrate derivatives such as hypromellose, hydroxypropyl cellulose, carboxymethyl starch, carageenan and xanthan may also be present.

The non-ammonium alkali salt used in the composition may be any food grade, nonvolatile, water soluble inorganic or organic salt species. The non-ammonium alkali salt may be selected from sodium, potassium, calcium, magnesium, aluminum salts. In some embodiments the non-ammonium alkali salt comprises sodium bicarbonate. The amount of non-ammonium alkali salt of use in the enteric coating of is typically in the range of from 1.5% to 15% by weight of the coating, such as from 1.5% to 8% by weight of the coating.

If the coating comprises a plasticizer, the plasticizer may be selected from glycerine, propylene glycol, mineral oil, triacetin, polyethylene glycol, acetylated monoglyceride, glyceryl monostearate, glyceryl tricaprylate/caprate, polysorbate andoleic acid. Various edible oils may also serve as the plasticizers. The plasticizer may also be a medium-chain triglyceride which is a medium-chain (6 to 12 carbons) fatty acid ester of glycerol. If glycerine is the plasticizer, then it may be used in an amount in the range of from about 1% to about 10% by weight, such as from 2% to 6% by weight. If mineral oil is the plasticizer, then it may be used in an amount in the range of from 3% to 9%, such as from 5% to 7% by weight. If glyceryl monostearate is the plasticizer, then it may be used in an amount in the range of from 3% to 25%, such as about 5% to about 20% by weight. If polysorbate 80 is the plasticizer, then it may be used in an amount in the range of from 0.5% to 12%, such as from 2% to 10% by weight. If acetylated monoglyceride is the plasticizer, then it may be used in an amount in the range of from 2% to 12%, such as from 4% to 10% by weight.

The release rate modifier controls the rate of release of the at least one active agent when the oral dosage form enters the small intestine. In some embodiments the release rate modifier comprises a hydrophobic material, such as a waxy solid. Exemplary waxes suitable to use as the hydrophobic material include hydrocarbon waxes, such as paraffin wax and the like, which are substantially or entirely free of unsaturation. Exemplary paraffin waxes are higher alkanes and mixtures of higher alkanes of the general formula $C_nH2_{2n+2}$, where typically, $20<n<50$, and thus have no unsaturation. They are solid at ambient temperatures and melt-processable.

In some embodiments the release rate modifier comprises a hydrophilic material. In some embodiments the hydrophilic material is a hydrophilic organic polymer which is capable of hydrogen bonding and solid at ambient temperatures (25° C.), hydrophilic and/or water soluble powders, and combinations thereof. In some embodiments the release rate modifier comprises a hydrophilic material and a hydrophobic material. That is, it comprises a plurality of materials and least one of the materials is more hydrophilic than at least a second material (that is in turn more hydrophobic than the first material).

In some embodiments the hydrophilic material is dispersed in the hydrophobic material. In the case of organic polymers, the hydrophilic material may be a material which is insoluble or substantially insoluble in the hydrophobic material such that it forms discrete regions where it is of high concentration in the hydrophobic material (or forms a separate). The regions may be spaced from each other by the hydrophobic material. In the case of hydrophilic and/or water soluble powders, the powder may be dispersed throughout the hydrophobic material, or in one embodiment, more highly concentrated near an outer surface thereof.

In the case of hydrophilic and/or water soluble powders as release rate modifiers, these may be present in a total concentration of from 0.001 wt. % to 30 wt. %, such as 0.1-20 wt. %, or 1.0 to 10 wt. %. Examples of hydrophilic powders include anhydrous inorganic particles, such as silicon dioxide, e.g., hydrophilic silica and silica nanopowders. Exemplary water-soluble powders include water-soluble acids and salts thereof, such as anhydrous phosphate salts, e.g., sodium polyphosphate, sodium tripolyphosphate, sodium pyrophosphate; anhydrous citric acid and salts thereof, such as alkali metals salts, e.g., sodium citrate; anhydrous sodium sulfate, anhydrous magnesium salts, such as magnesium sulfate and magnesium chloride. Combinations of such release agents may be employed. The hydrophilic and/or water soluble powders, such as silica, may have an average particle size of, for example, 1-100 nanometers (nm), e.g., 5-20 nm, and a surface area of, for example 50-400 m$^2$/g. Hydrophilic fumed silica, for example, may be obtained under the tradename AEROSIL™ from Evonik Industries with a specific surface area (measured by the BET method) in the range of 90-300 m$^2$/g. As an example, AEROSIL™ 200 has a specific surface area of 200 m$^2$/g.

When hydrophilic organic polymers are used as release rate modifiers, these may be present at a total concentration of from 0.5 wt. % to 40 wt. %, e.g., 1-35 wt. %, or 10-30 wt. %. In one embodiment, the hydrophilic polymer has a melting point of at least 30° C. or at least 40° C., such as up to 80° C. The hydrophilic polymer can have a weight average molecular weight of at least 300. Examples of suitable hydrophilic organic polymers include polyalkylene glycols, such as polyethylene glycol and polypropylene glycol, and esters thereof, polyamide compounds (e.g., polyvinylpyrrolidone), poly(vinyl acetate), poly(vinyl alcohol), poly(acrylic acid), polyacrylamide, polyoxylglycerides, such as lauroyl, oleoyl, and stearoyl polyoxylglycerides, which are mixtures of monoesters, diesters, and triesiers of glycerol and monoesters and diesters of polyethylene glycols (e.g., lauroyl macrogolglycerides, such as GELUCIRE™ 44/14, available from Gattefosse, which has a melting point of 44° C. and an HLB of 14), and ethylene oxide derivatives thereof, poloxamers, which are triblock copolymers having a central hydrophobic block of poly (propylene oxide) and two side blocks of poly(ethylene oxide) (e.g., poloxamer 188, which has a melting point 52° C.), and derivatives thereof, and mixtures thereof.

Exemplary polyethylene glycols (PEG) suitable for the release rate modifier may have a weight average molecular weight of from 300 daltons to 50,000 daltons, such as about 600-35000, or 1000 to 5,000 daltons. Such materials are commercially available as PEG 1000 (melting point 37-40° C.), PEG 1500 (melting point 44-48° C.), PEG 2000 (melting point 49-52° C.), and the like. A combination of polyethylene glycols having different molecular weights may be employed to tailor the release rate. For example a mixture may be formed by combining, e.g., in a ratio of from 1:10 to 10:1, a polyethylene glycol having a molecular weight of about 500-1200 (on average), such as PEG 1000, with a polyethylene glycol having a molecular weight of at least 1500 or at least 1800 (on average), such as PEG 1500 or PEG 2000. In one embodiment, a combination of PEGs with average molecular weight ranging from 300 daltons to 50,000 daltons may be mixed on appropriate amounts to provide a mixture which is liquid at a temperature of 35-70° C., such as 45-60° C. For example, PEG with an average molecular weight of 20,000 and PEG 1500 have melting points of 60-65° C. and 44-48° C., respectively, and a mixture of PEG 1500 and PEG 20,000 may be liquid at about 55° C., depending on the ratio.

In the case of hydrophilic organic polymers, such as PEG, discrete regions in which the polymer is localized may have an average size of, for example, at least 0.1 or at least 0.5 nm, and can be up to 100 nm, or up to 20 nm, e.g., 0.5-5 nm. For example, the hydrodynamic radius of glycerol is 0.3 nm and that of PEG 1000, PEG 2000 and PEG 4000 is approximately 0.9, 1.4 and 1.9 nm, respectively.

A ratio of hydrophobic material to the hydrophilic material in the release rate modifier may be from 1:99 to 99:1, expressed by weight, such as from 2:98 to 98:2, or from 10:90 to 90:10, or from 15:85 to 85:15. The ratio can be at least 30:70, or at least 40:60, or at least 60:40. For example, in the case of polymers, such as PEG, the ratio of hydrophobic material to release rate modifier may be about 60:40 or about 50:50. For hydrophilic and/or water soluble powders, the ratio of hydrophobic material to the release rate modifier may be higher, such as at least 85:15, or at least 90:10.

In some embodiments, the hydrophilic material increases the rate of release of the active ingredient, as compared with the hydrophobic material alone. For example, the amount of active ingredient released (e.g., expressed as weight of hydrogen peroxide), may be at least 10% greater or at least 50% greater, over an initial period of two hours, than for the equivalent dosage form formed without the hydrophilic material, when exposed to the same aqueous conditions (e.g., a buffered release medium, at a temperature of 30-40° C.).

In some embodiments, the release rate modifier may provide a more uniform rate of release of the active agent than equivalent dosage forms formed without the release rate modifier, when exposed to the same aqueous conditions (e.g., buffered release medium at a temperature of 30-40° C.). For example, the initial release rate (expressed as wt. of active agent/hr), over about two hours, may be, on average, less than that of an equivalent dosage form without the release rate modifier and may be, on average, higher than that of equivalent dosage form in the subsequent two hour period.

In some embodiments, the exemplary dosage form formed with the release rate modifier release at least 10%, or at least 20%, or at least 30%, or at least 40%, or at least 50%, or at least 60%, or at least 70%, or at least 80%, or at least 90% by weight of the total amount of active agent that they contain over a period of 4 hours, 6 hours, or 8 hours after contact with the small intestine or aqueous medium at 30°-40° C. In some embodiments, the exemplary dosage form formed with the release rate modifier release less than 25% or less than 50% by weight of the total amount of active agent that they contain over a period of 2 hours after contact with the small intestine or aqueous medium at 30°-40° C.

As will be appreciated from the foregoing, the amount and type of release rate modifier can be selected to tailor the release rate according to the desired application.

In one embodiment, the release rate modifier further includes an emulsifier, dispersed in the hydrophobic material. Exemplary nonionic surfactants suitable as emulsifiers include fatty acids, polyol fatty acid esters, such as polyglycerol esters, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), sugar esters, sorbitan esters, polysorbates, amine oxides and combinations thereof. As examples of suitable emulsifiers, nonionic surfactants with a low hydrophile-lipophile balance (HLB) may be used. The HLB may be from 2-5. Surfactants that are able to form micelles are able to improve the stability of hydrogen peroxide. Examples of these emulsifiers include C12-C24 fatty acids, such as lauric acid (CI 2), myristic acid (C14), palmitic acid (C16), stearic acid (C18), oleic acid (C18), linoleic acid (CI 8), and mixtures thereof. Such fatty acid emulsifiers can be obtained from Sigma-Aldrich under the tradename SPAN™, such as SPAN™ 60, which has an HLB of 4.7, SPAN™ 65, with an HLB of 2.1, SPAN™ 80, with an HLB of 4.3. Exemplary polyglycerol esters include polyglycerol polyricinoleate (PGPR), which has an HLB of 3, and is available from Evronik Industries, Essen Germany, or Danisco. A blend of surfactants having a high HLB and low HLB value may be used.

In some embodiments the oral dosage form comprises no more than one active agent. In some embodiments the oral dosage form comprises at least two active agents. In some embodiments the oral dosage form comprises at least three active agents In some embodiments the oral dosage form comprises an active agent that increases pH. In some embodiments the oral dosage form comprises an active agent that comprises a bicarbonate group. In some embodiments the oral dosage form comprises an active agent that comprises a bicarbonate salt, such as sodium bicarbonate, potassium bicarbonate, caesium bicarbonate, magnesium bicarbonate, calcium bicarbonate, ammonium bicarbonate, or a mixture thereof.

In some embodiments the oral dosage form comprises an active agent that increases oxygen tension. In some embodiments oral dosage form comprises an active agent that comprises a peroxide functional group. In some embodiments oral dosage form comprises an active agent that comprises hydrogen peroxide. In some embodiments oral dosage form comprises an active agent that is hydrogen peroxide. In some embodiments oral dosage form comprises an active agent that is an organic peroxide. In some embodiments oral dosage form comprises an active agent that is organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments oral dosage form comprises an active agent that is an inorganic peroxide. In some embodiments oral dosage form comprises an active agent that is carbamide peroxide. In some embodiments oral dosage form comprises an active agent that is sodium percarbonate.

In some embodiments the oral dosage form comprises an active agent that increases production of oxygen from stores in the gut. An example is catalase, a common enzyme found in nearly all living organisms exposed to oxygen. Accordingly, In some embodiments oral dosage form comprises an active agent that is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In such embodiments catalase increases oxygen tension by increasing the rate of decomposition of endogenous hydrogen peroxide to water and oxygen. In other embodiments catalase and an active agent that comprises hydrogen peroxide are used together. In such embodiments the catalase increases the rate of production of oxygen from the hydrogen peroxide active agent. In such embodiments the catalase may also act at least in part by increasing production of oxygen from endogenous sources.

In some embodiments the oral dosage form comprises a first active agent that increases pH and a second active agent that increases oxygen tension. In some embodiments the oral dosage form comprises a first active agent that increases pH, a second active agent that increases oxygen tension, and a third active agent that increases production of oxygen from endogenous sources. In some embodiments the oral dosage form comprises a first active agent that increases pH, a second active agent that increases oxygen tension and is a molecule comprising a peroxide functional group, and a third active agent that increases the rate of decomposition of the peroxide functional group to water and oxygen.

In some embodiments the oral dosage form comprises an active agent that comprises a peroxide functional group. In some embodiments the active agent that comprises a peroxide functional group is hydrogen peroxide. In some embodiments the active agent that comprises a peroxide functional group is carbamide peroxide. In some embodiments the active agent that comprises a peroxide functional group is sodium percarbonate. In some embodiments the oral dosage form further comprises a peroxide catalyst.

In some embodiments the oral dosage form comprises an active agent that comprises a bicarbonate group. In some embodiments the active agent that comprises a bicarbonate group is a bicarbonater salt. In some embodiments the active agent that comprises a bicarbonate group is sodium bicarbonate.

In some embodiments the oral dosage form comprises a first active agent that comprises a peroxide functional group and a second active agent that comprises a bicarbonate group. In some embodiments the first active agent that comprises a peroxide functional group is hydrogen peroxide. In some embodiments the first active agent that comprises a peroxide functional group is carbamide peroxide. In some embodiments the first active agent that comprises a peroxide functional group is sodium percarbonate. In some embodiments the second active agent that comprises a bicarbonate group is a bicarbonater salt. In some embodiments the second active agent that comprises a bicarbonate group is sodium bicarbonate. In some embodiments the oral dosage form further comprises a peroxide catalyst.

In some embodiments the oral dosage form is designed to target release of the at least one active agent to the small intestine. In some embodiments the oral dosage form is designed to target release of the at least one active agent to the proximal small intestine. In some embodiments the oral dosage form is designed to target release of the at least one active agent to the distal small intestine. In some embodiments the oral dosage form is designed to target release of the at least one active agent to the ileum. In some embodiments the oral dosage form is designed to target release of the at least one active agent to the distal ileum. Any suitable formulation known in the art for this purpose may be used.

In some embodiments the oral dosage form is designed to target release of the at least one active agent to the colon. Any suitable formulation known in the art for this purpose may be used. In some embodiments the at least one active agent is covalently linked with a carrier that targets release to the colon. In some embodiments the at least one active agent is coated with a pH-sensitive polymer that targets release to the colon. In some embodiments the at least one active agent is associated with a carrier that is degraded specifically by colonic bacteria such as a coating system utilizing one or combinations of polymers selected form azopolymers, starches, dextrans, mucopolysaccharides (e.g. inulin, guar gum, pectin, chondroitin sulfate, alginic acid). In some embodiments, the at least one active agent is formulated with a release rate modifier that is degraded by the gut microbiota selected from azopolymers, starches, dextrans, mucopolysaccharides (e.g. inulin, guar gum, pectin, chondroitin sulfate, alginic acid), dietary fibers. In some embodiments, the at least one active agent is formulated with solid powder of an anionic copolymer matrix based on methacrylic acid and methyl methacrylate such as Eudagrit S 100 in order to achieve pH dependent sustained release of actives in distal ileum and colon. In some embodiments the at least one active agent is formulated with a bioadhesive systems. In some embodiments the at least one active agent is formulated with an osmotic controlled drug delivery systems. In some embodiments the at least one active agent is formulated with a pressure controlled drug delivery system. In some embodiments the at least one active agent is formulated such that delivery and active agent release timing is delayed with internal capsule fill and/or use of an erodible coating (i.e. timed release).

In some embodiments the oral dosage form is formulated so that the at least one active agent is released in the distal small intestine. In some embodiments the oral dosage form is formulated so that the at least one active agent is released in the distal small intestine and the colon. In some embodiments the oral dosage form is formulated so that the at least one active agent is released in the ileum. In some embodiments the oral dosage form is formulated so that the at least one active agent is released in the ileum and the colon. In some embodiments the oral dosage form is formulated so that the at least one active agent is released in the distal ileum. In some embodiments the oral dosage form is formulated so that the at least one active agent is released in the distal ileum and the colon. In some embodiments the oral dosage form is formulated so that the at least one active agent is released in the jejunum. In some embodiments the oral dosage form is formulated so that the at least one active agent is released in the colon.

In some embodiments, the active agent(s) is encapsulated in intrinsically acid resistant capsules such as DRcaps™, enTRinsic™ (Capsugel) or ARcaps™ (Capscanada) to achieve enteric properties and to prevent release in the stomach. In some embodiments, the active agent(s) is encapsulated in ready made enteric coated capsules, whose caps and bodies have been enteric coated prior to filling with the active agent(s).

In some embodiments the composition that comprises at least one agent that increases oxygen tension and/or redox potential and/or pH in the colon of a subject does not comprise an enzyme. In some embodiments the composition that comprises at least one agent that increases oxygen tension and/or redox potential and/or pH in the colon of a subject does not comprise an enzyme that oxidizes ethanol to acetate.

E. Methods of Modifying the Microbiota Profile of the Colon of a Subject

As demonstrated in the examples, the inventor has discovered that administering an effective amount to the small intestine and/or large intestine of a subject of at least one agent that increases oxygen tension and/or redox potential and/or pH has a beneficial effect on the colon microbiome of the subject. By increasing the oxygen tension and/or redox potential and/or pH in the colon environment is modified such that (1) the relative abundance of bacterial types that promote at least one condition selected from a metabolic disease or disorder (such as obesity), metabolic syndrome (such as obesity), and cardiovascular disease is reduced; and/or (2) the relative abundance of bacterial types that ameliorate at least one condition selected from a metabolic disease or disorder (such as obesity), metabolic syndrome, and cardiovascular disease is increased. It has also been discovered that increasing the oxygen tension and/or redox potential and/or pH in the colon environment of a subject aides the weight management of the subject.

Accordingly, in a first aspect this invention provides methods of modifying the gut microbiome of a subject. In some embodiments the methods comprise administering at least one agent that increases oxygen tension and/or redox potential and/or pH in the colon of a subject. In some embodiments the at least one agent is administered by administering an effective amount of the at least one agent to the small intestine and/or large intestine of the subject. In some embodiments the at least one agent increases oxygen tension and is a peroxide. In some embodiments the at least one agent increases pH and is selected from bicarbonate salts, carbonate salts, bases, and buffers. In some embodiments the at least one agent is a peroxide catalyst. In some embodiments the at least one agent is selected from carbamide peroxide, sodium percarbonate, sodium bicarbonate, and catalase. In some embodiments the method comprises administering a peroxide and catalase to the subject. In some embodiments the peroxide is selected from carbamide peroxide, sodium percarbonate. In some embodiments the method further comprises administering sodium bicarbonate to the subject.

Administering an effective amount to the small intestine and/or large intestine of the subject of at least one agent that increases oxygen tension and/or redox potential and/or pH may be achieved using any suitable method. Generally, it will be preferable to provide the at least one active agent in the form of an oral dosage form, including for example any of the oral dosage forms disclosed herein. The oral dosage form is provided orally to the subject and then passes through the stomach to provide the at least one active agent to the small intestine and/or large intestine of the subject. However, alternative approaches may also be used. For example, a feeding tube may be placed to provide a composition comprising the at least one active agent directly to the small intestine or the large intestine. If an oral dosage form is used, any oral dosage form of this disclosure may be used, or any other suitable oral dosage form known in the art.

In some embodiments the at least one active agent is released in the distal small intestine. In some embodiments the at least one active agent is released in the distal small intestine and the colon. In some embodiments the at least one active agent is released in the ileum. In some embodiments the at least one active agent is released in the ileum and the colon. In some embodiments the at least one active agent is released in the distal ileum. In some embodiments the at least one active agent is released in the distal ileum and the colon. In some embodiments the at least one active agent is released in the colon.

In some embodiments the methods comprise administering no more than one active agent. In some embodiments the methods comprise administering at least two active agents. In some embodiments the methods comprise administering at least three active agents. In some embodiments of the methods a single oral dosage form is administered, which may comprise a plurality of active agents. In other embodiments a plurality of oral dosage forms is administered, which may each comprise a different active agent or different combination of active agents.

In some embodiments the methods comprise administering an active agent that increases pH. In some embodiments the methods comprise administering an active agent that comprises a bicarbonate group and/or a carbonate group. In some embodiments the methods comprise administering an active agent that comprises a bicarbonate salt, such as without limitation sodium bicarbonate, potassium bicarbonate, caesium bicarbonate, magnesium bicarbonate, calcium bicarbonate, ammonium bicarbonate, or a mixture thereof. In some embodiments the methods comprise administering an active agent that comprises a carbonate salt. In some embodiments the methods comprise administering an active agent that comprises a base. In some embodiments the methods comprise administering an active agent that comprises a buffer.

In some embodiments the methods comprise administering an active agent that increases oxygen tension. In some embodiments the methods comprise administering an active agent that comprises a peroxide functional group. In some embodiments the methods comprise administering an active agent that comprises hydrogen peroxide. In some embodiments the methods comprise administering an active agent that is hydrogen peroxide. In some embodiments at least one agent is hydrogen peroxide. In some embodiments the at least one peroxide is an organic peroxide. In some embodiments the at least one peroxide is an organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments the at least one agent is an inorganic peroxide. In some embodiments the at least one agent is an inorganic peroxide selected from Ammonium persulfate, Calcium peroxide, Magnesium peroxide, Potassium persulfate, Sodium perborate, and Sodium percarbonate. In some embodiments the at least one agent is carbamide peroxide. In some embodiments the at least one agent is Sodium percarbonate. In some embodiments the methods comprise administering an active agent that is carbamide peroxide. In some embodiments the methods comprise administering an active agent that is Sodium percarbonate.

In some embodiments the methods comprise administering an active agent that increases production of oxygen from stores in the gut and/or added stores. In some embodiments the agent that increases production of oxygen from stores in the gut and/or added stores is an organic peroxide catalyst or an inorganic peroxide catalyst. An example is catalase, a common enzyme found in nearly all living organisms exposed to oxygen. Accordingly, In some embodiments the methods comprise administering an active agent that is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In such embodiments catalase increases oxygen tension by increasing the rate of decomposition of endogenous hydrogen peroxide to water and oxygen. In other embodiments of the methods, catalase and an active agent that comprises hydrogen peroxide are used together. In such embodiments the catalase increases the rate of production of oxygen from the hydrogen peroxide active agent. In such embodiments the catalase may also act at least in part by increasing production of oxygen from endogenous sources.

In some embodiments the methods comprise administering a first active agent that increases pH and a second active agent that increases oxygen tension. In some embodiments the methods comprise administering a first active agent that increases pH, a second active agent that increases oxygen tension, and a third active agent that increases production of oxygen from endogenous sources. In some embodiments the methods comprise administering a first active agent that increases pH, a second active agent that increases oxygen tension and is a molecule comprising a peroxide functional group, and a third active agent that increases the rate of decomposition of the peroxide functional group to water and oxygen.

In some embodiments the methods comprise administering an active agent that comprises a peroxide functional group. In some embodiments the active agent that comprises a peroxide functional group is hydrogen peroxide. In some embodiments the active agent that comprises a peroxide functional group is carbamide peroxide. In some embodiments the oral dosage form further comprises a peroxide catalyst.

In some embodiments the methods comprise administering an active agent that comprises a carbonate group or a bicarbonate group. In some embodiments the active agent that comprises a bicarbonate group is a carbonate salt or a bicarbonate salt. In some embodiments the active agent that comprises a bicarbonate group is sodium bicarbonate. In some embodiments the active agent that comprises a carbonate group is sodium carbonate.

In some embodiments the methods comprise administering a first active agent that comprises a peroxide functional group and a second active agent that comprises a bicarbonate group. In some embodiments the first active agent that comprises a peroxide functional group is hydrogen peroxide. In some embodiments the first active agent that comprises a peroxide functional group is carbamide peroxide. In some embodiments the second active agent that comprises a bicarbonate group is a bicarbonater salt. In some embodiments the second active agent that comprises a bicarbonate group is sodium bicarbonate. In some embodiments the oral dosage form further comprises a peroxide catalyst.

The "effective amount" of the active agent(s) that is administered may be determined experimentally using methods that are standard in the art. For example, the methods described in the examples may be employed in mice and/or humans to identify an active agent and/or to perform a dose-ranging study to define the range of amounts of the active agent(s) that provide a desired benefit and/or the lowest dose that provides a desired benefit.

For agents that increase oxygen tension a dose range of 0.1 ng/kg to 1 g/kg may, for example, be tested in the mouse model to identify a therapeutically effective amount. For candidate agents that increase pH a dose range of 0.1 microgram/kg to 10 g/kg may, for example, be tested in the mouse model to identify a therapeutically effective amount.

Carbamide peroxide is used at a dose of from 1 ng/kg to 100 mg/kg per day, such as from 1 ng/kg to 10 ng/kg, from 10 ng/kg to 100 ng/kg, from 1 microgram/kg to 10 micrograms/kg, from 10 microgram/kg to 100 micrograms/kg, from 100 microgram/kg to 1 mg/kg, from 1 mg/kg to 10 mg/kg, or from 10 mg/kg to 100 mg/kg, or at a dose that is bounded by any combination of two of these recited endpoints or at a dose of at least one of these endpoints. The dose is administered 1, 2, 3, 4, 5, 6, 7, 8, 9, or 10 times per day. In a preferred embodiment the dose is administered 3 times per day.

In some embodiments carbamide peroxide is used at a dose of at least 25 mg three times per day. In some embodiments carbamide peroxide is used at a dose of at least 50 mg three times per day. In some embodiments carbamide peroxide is used at a dose of at least 75 mg three times per day. In some embodiments carbamide peroxide is used at a dose of at least 100 mg three times per day.

Sodium percarbonate is used at a dose of from 1 ng/kg to 100 mg/kg, such as from 1 ng/kg to 10 ng/kg, from 10 ng/kg to 100 ng/kg, from 1 microgram/kg to 10 micrograms/kg, from 10 microgram/kg to 100 micrograms/kg, from 100 microgram/kg to 1 mg/kg, from 1 mg/kg to 10 mg/kg, or from 10 mg/kg to 100 mg/kg, or at a dose that is bounded by any combination of two of these recited endpoints or at a dose of at least one of these endpoints. The dose is administered 1, 2, 3, 4, 5, 6, 7, 8, 9, or 10 times per day. In a preferred embodiment the dose is administered 3 times per day.

In some embodiments sodium percarbonate is used at a dose of at least 25 mg three times per day. In some embodiments sodium percarbonate is used at a dose of at least 50 mg three times per day. In some embodiments sodium percarbonate is used at a dose of at least 75 mg three times per day. In some embodiments sodium percarbonate is used at a dose of at least 100 mg three times per day.

In some embodiments the active agent comprises hydrogen peroxide and the agent is administered to a subject at a dose of from 0.01 mg to 100 mg of hydrogen peroxide equivalent. In some embodiments the active agent is administered at a dose of from 0.1 mg to 5 mg of hydrogen peroxide equivalent. In some embodiments the active agent is administered at a dose of from 5 mg to 10 mg of hydrogen peroxide equivalent. In some embodiments the active agent is administered at a dose of from 10 mg to 20 mg of hydrogen peroxide equivalent. In some embodiments the active agent is administered at a dose of from 20 mg to 40 mg of hydrogen peroxide equivalent. In some embodiments the active agent is administered at a dose of from 40 mg to 60 mg of hydrogen peroxide equivalent. In some embodiments the active agent is administered at a dose of from 60 mg to 80 mg of hydrogen peroxide equivalent. In some embodiments the active agent is administered at a dose of from 80 mg to 100 mg of hydrogen peroxide equivalent.

In some embodiments the active agent is administered at a dose of from 100 mg to 1 g of hydrogen peroxide equivalent. In some embodiments the active agent is administered at a dose of from 100 mg to 200 mg of hydrogen peroxide equivalent. In some embodiments the active agent is administered at a dose of from 200 mg to 400 mg of hydrogen peroxide equivalent.

Sodium bicarbonate is used at a dose of from 1 microgram/kg to 1 g/kg, such as at 1 microgram/kg to 10 micrograms, from 10 micrograms/kg to 100 micrograms/kg, from 100 micrograms/kg to 1 mg/kg, from 1 mg/kg to 10 mg/kg, from 10 mg/kg to 100 mg/kg, or from 100 mg/kg to 1 g, or at a dose that is bounded by any combination of two of these recited endpoints or at a dose of at least one of these endpoints.

Catalase is used at a dose of from 0.0001 to 10,000 Baker's units per kg, such as from 0.0001 to 0.001 Baker's units per kg, from 0.001 to 0.01 Baker's units per kg, from 0.01 to 0.1 Baker's units per kg, from 0.1 to 1 Baker's units per kg, from 1 to 10 Baker's units per kg, from 10 to 100 Baker's units per kg, from 100 to 1,000 Baker's units per kg, or from 1,000 to 10,000 Baker's units per kg. The dose is administered 1, 2, 3, 4, 5, 6, 7, 8, 9, or 10 times per day. In a preferred embodiment the dose is administered 3 times per day.

In some embodiments catalase is used at a dose of at least 25 mg three times per day. In some embodiments catalase is used at a dose of at least 50 mg three times per day. In some embodiments catalase is used at a dose of at least 75 mg three times per day. In some embodiments catalase is used at a dose of at least 100 mg three times per day.

In general the active agent is administered over a dosing period. A dosing period is a span of time during which the active agent is administered to a subject at a regular dosing interval, such as every four hours, every eight hours, every twelve hours, or once a day. The dosing period may comprise one week, two weeks, one month, three months, six months, nine months, or one year. In some embodiments the active agent is administered at least once a day for the dosing period. In some embodiments the active agent is administered at least once every other day for the dosing period. In some embodiments the active agent is administered at least two times a week for the dosing period. In some embodiments the active agent is administered at least three times a week for the dosing period. In some embodiments the active agent is administered at least four times a week for the dosing period. In some embodiments the active agent is administered at least five times a week for the dosing period.

In some embodiments the active agent is administered on an empty stomach. In other embodiments the active agent is administered with food. In some embodiments the active agent is administered with meals. In some embodiments the active agent is administered after a meal.

In some embodiments of the methods the microbiota profile of the colon of the subject is modulated as a result of the treatment. In some embodiments administering the effective amount of the at least one agent to the small intestine and/or large intestine of the subject modulates the microbiota profile of the large intestine of the subject.

In some embodiments the relative abundance of at least one of aerobic bacteria and facultatively anaerobic bacteria is increased in the microbiota of the colon of the subject. In some embodiments the relative abundance of bacteria in at least one phylum selected from Proteobacteria, Bacteriodetes, and Verrucomicrobia is increased in the microbiota of the colon of the subject. In some embodiments the relative abundance of bacteria in the Proteobacteria phylum is increased in the microbiota of the colon of the subject. In some embodiments the relative abundance of bacteria in the Firmicutes phylum is decreased in the microbiota of the colon of the subject. In some embodiments the relative abundance of bacteria in at least one phylum selected from Proteobacteria, Bacteriodetes, and Verrucomicrobia is increased in the microbiota of the colon of the subject; and the relative abundance of bacteria in the Firmicutes phylum is decreased in the microbiota of the colon of the subject.

In some embodiments the relative abundance of at least one class of bacteria selected from Gammaproteobacteria, Alphaproteobacteria and Bacteriodetes is increased in the microbiota of the colon of the subject. In some embodiments the relative abundance of at least one class of bacteria selected from Clostridia, Erysipelotrichia, and Bacilli is decreased in the microbiota of the colon of the subject. In some embodiments the relative abundance of at least one class of bacteria selected from Gammaproteobacteria, Alphaproteobacteria and Bacteriodetes is increased in the microbiota of the colon of the subject; and the relative abundance of at least one class of bacteria selected from Clostridia, Erysipelotrichia, and Bacilli is decreased in the microbiota of the colon of the subject.

In some embodiments the relative abundance of at least one order of bacteria selected from Enterobacteriales, Bacteriodales, and Verrucomicrobiales is increased in the microbiota of the colon of the subject. In some embodiments the relative abundance of at least one order of bacteria selected from Clostridiales, Erysiopelotrichales, and Lactobacillales is decreased in the microbiota of the colon of the subject. In some embodiments the relative abundance of at least one order of bacteria selected from Enterobacteriales, Bacteriodales, and Verrucomicrobiales is increased in the microbiota of the colon of the subject; and the relative abundance of at least one order of bacteria selected from Clostridiales, Erysiopelotrichales, and Lactobacillales is decreased in the microbiota of the colon of the subject.

In some embodiments the relative abundance of at least one family of bacteria selected from Enterobacteriaceae and Bacteroidaceae is increased in the microbiota of the colon of the subject. In some embodiments the relative abundance of at least one family of bacteria selected from Erysipelotrichaceae, Prevotellaceae, Coriobacteriaceae, and Alcaligenaceae is decreased in the microbiota of the colon of the subject. In some embodiments the relative abundance of at least one family of bacteria selected from Enterobacteriaceae and Bacteroidaceae is increased in the microbiota of the colon of the subject; and the relative abundance of at least one family of bacteria selected from Erysipelotrichaceae, Prevotellaceae, Coriobacteriaceae, and Alcaligenaceae is decreased in the microbiota of the colon of the subject.

In some embodiments the relative abundance of at least one genus of bacteria selected from *Escherichia, Bacteroides, Alistipes*, and *Akkermansia* is increased in the microbiota of the colon of the subject. In some embodiments the relative abundance of at least one genus of bacteria selected from *Clostridium* and *Lactobacillus* is decreased in the microbiota of the colon of the subject. In some embodiments the relative abundance of at least one genus of bacteria selected from *Escherichia, Bacteroides, Alistipes*, and

*Akkermansia* is increased in the microbiota of the colon of the subject; and the relative abundance of at least one genus of bacteria selected from *Clostridium* and *Lactobacillus* is decreased in the microbiota of the colon of the subject.

In some embodiments the relative abundance of *Akkermansia muciniphila* is increased in the microbiota of the colon of the subject.

In some embodiments the relative abundance of at least one type of bacteria selected from Gammaproteobacteria, Alphaproteobacteria, Enterobacteriaceae (e.g., *Escherichia*), Bacteriodetes, and Verrucomicrobia (e.g., *Akkermansia*) is increased in the microbiota of the colon of the subject. In some embodiments the relative abundance of at least one type of bacteria selected from Firmicutes (Clostridia), Erysiopelotrichaceae is decreased in the microbiota of the colon of the subject.

In some embodiments the relative abundance of at least one type of bacteria selected from Gammaproteobacteria, Alphaproteobacteria, Enterobacteriaceae (e.g., *Escherichia*), Bacteriodetes, and Verrucomicrobia (e.g., *Akkermansia*) is increased in the microbiota of the colon of the subject; and the relative abundance of at least one type of bacteria selected from Firmicutes (Clostridia), Erysiopelotrichaceae is decreased in the microbiota of the colon of the subject.

In some embodiments the methods further comprise collecting a stool sample from the subject and assaying the microbiota profile in the stool sample to determine the relative abundance of at least one phylum of bacteria selected from Proteobacteria, Bacteriodetes, Verrucomicrobia, and Firmicutes; and/or to determine the relative abundance of at least one class of bacteria selected from Gammaproteobacteria, Alphaproteobacteria, Bacteriodetes, Clostridia, Erysipelotrichia, and Bacilli; and/or to determine the relative abundance of at least one order of bacteria selected from Enterobacteriales, Bacteriodales, Verrucomicrobiales, Clostridiales, Erysipelotrichales, and Lactobacillales; and/or to determine the relative abundance of at least one family of bacteria selected from Enterobacteriaceae, Bacteroidaceae, Erysiopelotrichaceae, Prevotellaceae, Coriobacteriaceae, and Alcaligenaceae; and/or to determine the relative abundance of at least one genus of bacteria selected from *Escherichia, Bacteroides, Alistipes, Akkermansia, Clostridium*, and *Lactobacillus*; and/or to determine the relative abundance of *Akkermansia muciniphila*. In some embodiments the stool sample is collected at least one time point selected from before initiation of administering at least one agent that increases oxygen tension and/or redox potential and/or pH, during a course of administering at least one agent that increases oxygen tension and/or redox potential and/or pH, and after completion of administering a course of at least one agent that increases oxygen tension and/or redox potential and/or pH.

In some embodiments in which the relative abundance of a type of bacteria is increased in the colon of the subject the increase in relative abundance is at least 10%, at least 25%, at least 50%, at least 75%, at least 100% (i.e., one fold), at least 200% (i.e., two fold), at least 300%, at least 400%, at least 500%, at least 600%, at least 700%, at least 800%, at least 900%, at least 1,000% (i.e., ten fold), or at least 10,000% (i.e., 100 fold). In some embodiments in which the relative abundance of a type of bacteria is decreased in the colon of the subject the decrease in relative abundance is at least 10%, at least 25%, at least 50%, at least 75%, at least 90% (i.e., ten fold), at least 95% (i.e., 20 fold), at least 99% (i.e., 100 fold), at least 99.9% (i.e., 1000 fold).

In some embodiments of the methods the at least one agent that increases oxygen tension and/or redox potential and/or pH in the colon of a subject is administered to the subject without administering an enzyme to the subject. In some embodiments of the methods the at least one agent that increases oxygen tension and/or redox potential and/or pH in the colon of a subject is administered to the subject without administering an enzyme that oxidizes ethanol to acetate to the subject.

F. Methods of Weight Management

As demonstrated in the examples, the inventor has discovered that administering an effective amount to the small intestine and/or large intestine of a subject of at least one agent that increases oxygen tension and/or redox potential and/or pH has a beneficial effect on the colon microbiome of the subject. By increasing the oxygen tension and/or redox potential and/or pH the colon environment is modified such that (1) the relative abundance of bacterial types that promote at least one condition selected from a metabolic disease or disorder (such as obesity), metabolic syndrome, and cardiovascular disease is reduced; and/or (2) the relative abundance of bacterial types that ameliorate at least one condition selected from a metabolic disease or disorder (such as obesity), metabolic syndrome, and cardiovascular disease is increased. It has also been discovered that increasing the oxygen tension and/or redox potential and/or pH in the colon environment of a subject acts to manage the weight of the subject. Without wishing to be bound by theory, it appears that microbiome modifications caused by increasing the oxygen tension and/or redox potential and/or pH of a subject's colon in turn manage the weight of the subject. This dramatic result is surprising and demonstrates unexpected benefits of the invention.

Accordingly, methods of weight management in a subject are also provided. In some embodiments the methods comprise administering an effective amount to the small intestine and/or large intestine of the subject of at least one agent that increases oxygen tension and/or redox potential and/or pH in the colon of the subject to thereby manage the weight of the subject. In some embodiments the weight management comprises at least one of weight loss, maintenance of weight, controlling weight gain, body mass index (BMI) reduction, maintenance of BMI, and controlling BMI gain. In some embodiments the subject is overweight or obese. In some embodiments the subject has at least one weight-related condition. In some embodiments the at least one weight-related condition is selected from a metabolic disease or disorder, metabolic syndrome, and cardiovascular disease. In some embodiments the at least one weight-related condition is selected from hypertension, dyslipidemia, and type 2 diabetes. In some embodiments at least one symptom of the at least one weight-related condition is ameliorated.

In some embodiments administering the effective amount to the small intestine and/or large intestine of the subject of at least one agent that increases oxygen tension and/or redox potential and/or pH in the colon of the subject increases the relative abundance of at least one of aerobic bacteria and facultatively anaerobic bacteria in the microbiota of the colon of the subject. In some embodiments administering the effective amount to the small intestine and/or large intestine of the subject of at least one agent that increases oxygen tension and/or redox potential and/or pH in the colon of the subject increases the relative abundance of bacteria in at least one phylum selected from Proteobacteria, Bacteriodetes, and Verrucomicrobia is increased in the microbiota of the colon of the subject. In some embodiments the relative abundance of bacteria in the phylum Proteobacteria is increased in the microbiota of the colon of the subject. In some embodiments administering the effective amount to the small intestine and/or large intestine of the subject of at least one agent that increases oxygen tension and/or redox potential and/or pH in the colon of the subject decreases the relative abundance of bacteria in the Firmicutes phylum in the microbiota of the colon of the subject. In some embodiments administering the effective amount to the small intestine and/or large intestine of the subject of at least one agent that increases oxygen tension and/or redox potential and/or pH in the colon of the subject decreases the relative abundance of bacteria in the Firmicutes phylum in the microbiota of the colon of the subject.

In some embodiments the at least one agent increases oxygen tension and is a peroxide. In some embodiments the at least one agent increases pH and is selected from bicarbonate salts, carbonate salts, bases, and buffers. In some embodiments the at least one agent is a peroxide catalyst. In some embodiments the at least one agent is selected from carbamide peroxide, sodium percarbonate, sodium bicarbonate, and catalase. In some embodiments the method comprises administering a peroxide and catalase to the subject. In some embodiments the peroxide is selected from carbamide peroxide, sodium percarbonate. In some embodiments the method further comprises administering sodium bicarbonate to the subject.

In some embodiments the effective amount of at least one of an agent that increases oxygen tension and/or redox potential and/or pH is administered to the small intestine and/or large intestine of the subject by oral administration of the at least one agent to the subject. In some embodiments the at least one agent is administered as an oral dosage form comprising the at least one agent and an enteric coating encasing the at least one agent. In some embodiments the oral dosage form is formulated for sustained release.

In some embodiments of the methods the at least one agent that increases oxygen tension and/or redox potential and/or pH in the colon of a subject is administered to the subject without administering an enzyme to the subject. In some embodiments of the methods the at least one agent that increases oxygen tension and/or redox potential and/or pH in the colon of a subject is administered to the subject without administering an enzyme that oxidizes ethanol to acetate to the subject.

In general the active agent is administered over a dosing period. A dosing period is a span of time during which the active agent is administered to a subject at a regular dosing interval, such as every four hours, every eight hours, every twelve hours, or once a day. The dosing period may comprise one week, two weeks, one month, three months, six months, nine months, or one year. In some embodiments the active agent is administered at least once a day for the dosing period. In some embodiments the active agent is administered at least once every other day for the dosing period. In some embodiments the active agent is administered at least two times a week for the dosing period. In some embodiments the active agent is administered at least three times a week for the dosing period. In some embodiments the active agent is administered at least four times a week for the dosing period. In some embodiments the active agent is administered at least five times a week for the dosing period.

In some embodiments the dosing period is at least 3 days, at least 5 days, at least 1 week, at least 2 weeks, at least 4 weeks, at least 2 months, at least 3 months, at least 6 months, or at least one year. In some embodiments the dosing period is 3 days, 5 days, 1 week, 2 weeks, 4 weeks, 2 months, 3 months, 6 months, or one year. In some embodiments the dosing period is from 3 to 10 days, from 1 to 2 weeks, from 2 to 4 weeks, from 1 to 2 months, from 3 to 6 months, or from 6 to 12 months.

In some embodiments the at least one agent is administered for a dosing period and the weight of the subject does not increase during the dosing period. In some embodiments the at least one agent is administered for a dosing period and the weight of the subject decreases during the dosing period. In some embodiments the weight of the subject decreases by at least 1%, at least 2%, at least 3%, at least 4%, at least 5%, at least 6%, at least 7%, at least 8%, at least 9%, or at least 10% during the dosing period.

In some embodiments the at least one agent is administered for a dosing period and the BMI of the subject does not increase during the dosing period. In some embodiments the at least one agent is administered for a dosing period and the BMI of the subject decreases during the dosing period. In some embodiments the BMI of the subject decreases by at least 1%, at least 2%, at least 3%, at least 4%, at least 5%, at least 6%, at least 7%, at least 8%, at least 9%, or at least 10% during the dosing period.

In some embodiments both the weight of the subject and the BMI of the subject do not increase during the dosing period. In some embodiments both the weight of the subject and the BMI of the subject decrease during the dosing period. In some embodiments the weight of the subject and the BMI of the subject independently each decrease by at least 1%, at least 2%, at least 3%, at least 4%, at least 5%, at least 6%, at least 7%, at least 8%, at least 9%, or at least 10% during the dosing period.

In some embodiments in which the subject has at least one weight-related condition the at least one weight-related condition is selected from a metabolic disease or disorder, metabolic syndrome, and cardiovascular disease.

In some embodiments the at least one weight-related condition is metabolic syndrome. In some embodiments the metabolic syndrome is characterized by at least one feature selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least two features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least three features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least four features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least five features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation.

In some embodiments the subject is pre-obese, obese, or morbidly obese. In some embodiments weight management of the pre-obese, obese, or morbidly obese subject results in at least one of inducing weight loss in a pre-obese, obese, or morbidly obese subject; reducing BMI in a pre-obese, obese, or morbidly obese subject; reducing food intake in a pre-obese, obese, or morbidly obese subject; improving glucose homeostasis in a pre-obese, obese, or morbidly obese subject; preventing weight gain and preventing an increase in BMI in a normal, pre-obese, obese, or morbidly obese subject.

In certain embodiments, the at least one active agent is administered to a subject suffering from obesity (e.g., a pro-obese, obese, or morbidly obese patient), an obesity-related disease or disorder, diabetes, insulin-resistance syndrome, lypodystrpohy, nonalcoholic steatohepatitis, a cardiovascular disease, polycystic ovary syndrome, or a metabolic syndrome.

In some embodiments the at least one condition is cardiovascular disease.

In some embodiments the at least one condition is type-II diabetes.

Administering an effective amount to the small intestine and/or large intestine of the subject of at least one agent that increases oxygen tension and/or redox potential and/or pH may be achieved using any suitable method. Generally, it will be preferable to provide the at least one active agent in the form of an oral dosage form, including for example any of the oral dosage forms disclosed herein. The oral dosage form is provided orally to the subject and then passes through the stomach to provide the at least one active agent to the small intestine and/or large intestine of the subject. However, alternative approaches may also be used. For example, a feeding tube may be placed to provide a composition comprising the at least one active agent directly to the small intestine or the large intestine. If an oral dosage form is used, any oral dosage form of this disclosure may be used, or any other suitable oral dosage form known in the art.

In some embodiments the at least one active agent is released in the distal small intestine. In some embodiments the at least one active agent is released in the distal small intestine and the colon. In some embodiments the at least one active agent is released in the ileum. In some embodiments the at least one active agent is released in the ileum and the colon. In some embodiments the at least one active agent is released in the distal ileum. In some embodiments the at least one active agent is released in the distal ileum and the colon. In some embodiments the at least one active agent is released in the colon.

In some embodiments the methods comprise administering no more than one active agent. In some embodiments the methods comprise administering at least two active agents. In some embodiments the methods comprise administering at least three active agents. In some embodiments of the methods a single oral dosage form is administered, which may comprise a plurality of active agents. In other embodiments a plurality of oral dosage forms is administered, which may each comprise a different active agent or different combination of active agents.

In some embodiments the methods comprise administering an active agent that increases pH. In some embodiments the methods comprise administering an active agent that comprises a bicarbonate group and/or a carbonate group. In some embodiments the methods comprise administering an active agent that comprises a bicarbonate salt, such as without limitation sodium bicarbonate, potassium bicarbonate, caesium bicarbonate, magnesium bicarbonate, calcium bicarbonate, ammonium bicarbonate, or a mixture thereof. In some embodiments the methods comprise administering an active agent that comprises a carbonate salt. In some embodiments the methods comprise administering an active agent that comprises a base. In some embodiments the methods comprise administering an active agent that comprises a buffer.

In some embodiments the methods comprise administering an active agent that increases oxygen tension. In some embodiments the methods comprise administering an active agent that comprises a peroxide functional group. In some embodiments the methods comprise administering an active agent that comprises hydrogen peroxide. In some embodiments the methods comprise administering an active agent that is hydrogen peroxide. In some embodiments at least one agent is hydrogen peroxide. In some embodiments the at least one peroxide is an organic peroxide. In some embodiments the at least one peroxide is an organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments the at least one agent is an inorganic peroxide. In some embodiments the at least one agent is an inorganic peroxide selected from Ammonium persulfate, Calcium peroxide, Magnesium peroxide, Potassium persulfate, Sodium perborate, and Sodium percarbonate. In some embodiments the at least one agent is carbamide peroxide. In some embodiments the at least one agent is Sodium percarbonate. In some embodiments the methods comprise administering an active agent that is carbamide peroxide. In some embodiments the methods comprise administering an active agent that is Sodium percarbonate.

In some embodiments the methods comprise administering an active agent that increases production of oxygen from stores in the gut and/or added stores. In some embodiments the agent that increases production of oxygen from stores in the gut and/or added stores is an organic peroxide catalyst or an inorganic peroxide catalyst. An example is catalase, a common enzyme found in nearly all living organisms exposed to oxygen. Accordingly, In some embodiments the methods comprise administering an active agent that is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In such embodiments catalase increases oxygen tension by increasing the rate of decomposition of endogenous hydrogen peroxide to water and oxygen. In other embodiments of the methods, catalase and an active agent that comprises hydrogen peroxide are used together. In such embodiments the catalase increases the rate of production of oxygen from the hydrogen peroxide active agent. In such embodiments the catalase may also act at least in part by increasing production of oxygen from endogenous sources.

In some embodiments the methods comprise administering a first active agent that increases pH and a second active agent that increases oxygen tension. In some embodiments the methods comprise administering a first active agent that increases pH, a second active agent that increases oxygen tension, and a third active agent that increases production of oxygen from endogenous sources. In some embodiments the methods comprise administering a first active agent that increases pH, a second active agent that increases oxygen tension and is a molecule comprising a peroxide functional group, and a third active agent that increases the rate of decomposition of the peroxide functional group to water and oxygen.

In some embodiments the methods comprise administering an active agent that comprises a peroxide functional group. In some embodiments the active agent that comprises a peroxide functional group is hydrogen peroxide. In some embodiments the active agent that comprises a peroxide functional group is carbamide peroxide. In some embodiments the oral dosage form further comprises a peroxide catalyst.

In some embodiments the methods comprise administering an active agent that comprises a carbonate group or a bicarbonate group. In some embodiments the active agent that comprises a bicarbonate group is a carbonate salt or a bicarbonate salt. In some embodiments the active agent that comprises a bicarbonate group is sodium bicarbonate. In some embodiments the active agent that comprises a carbonate group is sodium carbonate.

In some embodiments the methods comprise administering a first active agent that comprises a peroxide functional group and a second active agent that comprises a bicarbonate group. In some embodiments the first active agent that comprises a peroxide functional group is hydrogen peroxide. In some embodiments the first active agent that comprises a peroxide functional group is carbamide peroxide. In some embodiments the second active agent that comprises a bicarbonate group is a bicarbonater salt. In some embodiments the second active agent that comprises a bicarbonate group is sodium bicarbonate. In some embodiments the oral dosage form further comprises a peroxide catalyst.

The "effective amount" of the active agent(s) that is adminstered may be determined experimentally using methods that are standard in the art. For example, the methods described in the examples may be employed in mice and/or humans to identify an active agent and/or to perform a dose-ranging study to define the range of amounts of the active agent(s) that provide a desired benefit and/or the lowest dose that provides a desired benefit.

For agents that increase oxygen tension a dose range of 0.1 ng/kg to 1 g/kg may, for example, be tested in the mouse model to identify a therapeutically effective amount. For candidate agents that increase pH a dose range of 0.1 microgram/kg to 10 g/kg may, for example, be tested in the mouse model to identify a therapeutically effective amount.

Carbamide peroxide is used at a dose of from 1 ng/kg to 100 mg/kg per day, such as from 1 ng/kg to 10 ng/kg, from 10 ng/kg to 100 ng/kg, from 1 microgram/kg to 10 micrograms/kg, from 10 microgram/kg to 100 micrograms/kg, from 100 microgram/kg to 1 mg/kg, from 1 mg/kg to 10 mg/kg, or from 10 mg/kg to 100 mg/kg, or at a dose that is bounded by any combination of two of these recited endpoints or at a dose of at least one of these endpoints. The dose is administered 1, 2, 3, 4, 5, 6, 7, 8, 9, or 10 times per day. In a preferred embodiment the dose is administered 3 times per day.

In some embodiments carbamide peroxide is used at a dose of at least 25 mg three times per day. In some embodiments carbamide peroxide is used at a dose of at least 50 mg three times per day. In some embodiments carbamide peroxide is used at a dose of at least 75 mg three times per day. In some embodiments carbamide peroxide is used at a dose of at least 100 mg three times per day.

Sodium percarbonate is used at a dose of from 1 ng/kg to 100 mg/kg, such as from 1 ng/kg to 10 ng/kg, from 10 ng/kg to 100 ng/kg, from 1 microgram/kg to 10 micrograms/kg, from 10 microgram/kg to 100 micrograms/kg, from 100 microgram/kg to 1 mg/kg, from 1 mg/kg to 10 mg/kg, or from 10 mg/kg to 100 mg/kg, or at a dose that is bounded by any combination of two of these recited endpoints or at a dose of at least one of these endpoints. The dose is administered 1, 2, 3, 4, 5, 6, 7, 8, 9, or 10 times per day. In a preferred embodiment the dose is administered 3 times per day.

In some embodiments sodium percarbonate is used at a dose of at least 25 mg three times per day. In some embodiments sodium percarbonate is used at a dose of at least 50 mg three times per day. In some embodiments sodium percarbonate is used at a dose of at least 75 mg three times per day. In some embodiments sodium percarbonate is used at a dose of at least 100 mg three times per day.

In some embodiments the active agent comprises hydrogen peroxide and the agent is administered to a subject at a dose of from 0.01 mg to 100 mg of hydrogen peroxide equivalent. In some embodiments the active agent is administered at a dose of from 0.1 mg to 5 mg of hydrogen peroxide equivalent. In some embodiments the active agent is administered at a dose of from 5 mg to 10 mg of hydrogen peroxide equivalent. In some embodiments the active agent is administered at a dose of from 10 mg to 20 mg of hydrogen peroxide equivalent. In some embodiments the active agent is administered at a dose of from 20 mg to 40 mg of hydrogen peroxide equivalent. In some embodiments the active agent is administered at a dose of from 40 mg to 60 mg of hydrogen peroxide equivalent. In some embodiments the active agent is administered at a dose of from 60 mg to 80 mg of hydrogen peroxide equivalent. In some embodiments the active agent is administered at a dose of from 80 mg to 100 mg of hydrogen peroxide equivalent.

In some embodiments the active agent is administered at a dose of from 100 mg to 1 g of hydrogen peroxide equivalent. In some embodiments the active agent is administered at a dose of from 100 mg to 200 mg of hydrogen peroxide equivalent. In some embodiments the active agent is administered at a dose of from 200 mg to 400 mg of hydrogen peroxide equivalent.

Sodium bicarbonate is used at a dose of from 1 microgram/kg to 1 g/kg, such as at 1 microgram/kg to 10 micrograms, from 10 micrograms/kg to 100 micrograms/kg, from 100 micrograms/kg to 1 mg/kg, from 1 mg/kg to 10 mg/kg, from 10 mg/kg to 100 mg/kg, or from 100 mg/kg to 1 g, or at a dose that is bounded by any combination of two of these recited endpoints or at a dose of at least one of these endpoints.

Catalase is used at a dose of from 0.0001 to 10,000 Baker's units per kg, such as from 0.0001 to 0.001 Baker's units per kg, from 0.001 to 0.01 Baker's units per kg, from 0.01 to 0.1 Baker's units per kg, from 0.1 to 1 Baker's units per kg, from 1 to 10 Baker's units per kg, from 10 to 100 Baker's units per kg, from 100 to 1,000 Baker's units per kg, or from 1,000 to 10,000 Baker's units per kg. The dose is administered 1, 2, 3, 4, 5, 6, 7, 8, 9, or 10 times per day. In a preferred embodiment the dose is administered 3 times per day.

In some embodiments catalase is used at a dose of at least 25 mg three times per day. In some embodiments catalase is used at a dose of at least 50 mg three times per day. In some embodiments catalase is used at a dose of at least 75 mg three times per day. In some embodiments catalase is used at a dose of at least 100 mg three times per day.

In some embodiments the active agent is administered on an empty stomach. In other embodiments the active agent is administered with food. In some embodiments the active agent is administered with meals.

In some embodiments of the methods the microbiota profile of the colon of the subject is modulated as a result of the treatment. In some embodiments administering the effective amount of the at least one agent to the small intestine and/or large intestine of the subject modulates the microbiota profile of the large intestine of the subject.

In some embodiments the relative abundance of at least one of aerobic bacteria and facultatively anaerobic bacteria is increased in the microbiota of the colon of the subject. In some embodiments the relative abundance of bacteria in at least one phylum selected from Proteobacteria, Bacteriodetes, and Verrucomicrobia is increased in the microbiota of the colon of the subject. In some embodiments the relative abundance of bacteria in the Proteobacteria phylum is increased in the microbiota of the colon of the subject. In some embodiments the relative abundance of bacteria in the Firmicutes phylum is decreased in the microbiota of the colon of the subject. In some embodiments the relative abundance of bacteria in at least one phylum selected from Proteobacteria, Bacteriodetes, and Verrucomicrobia is increased in the microbiota of the colon of the subject; and the relative abundance of bacteria in the Firmicutes phylum is decreased in the microbiota of the colon of the subject.

In some embodiments the relative abundance of at least one class of bacteria selected from Gammaproteobacteria, Alphaproteobacteria and Bacteriodetes is increased in the microbiota of the colon of the subject. In some embodiments the relative abundance of at least one class of bacteria selected from Clostridia, Erysipelotrichia, and Bacilli is decreased in the microbiota of the colon of the subject. In some embodiments the relative abundance of at least one class of bacteria selected from Gammaproteobacteria, Alphaproteobacteria and Bacteriodetes is increased in the microbiota of the colon of the subject; and the relative abundance of at least one class of bacteria selected from Clostridia, Erysipelotrichia, and Bacilli is decreased in the microbiota of the colon of the subject.

In some embodiments the relative abundance of at least one order of bacteria selected from Enterobacteriales, Bacteriodales, and Verrucomicrobiales is increased in the microbiota of the colon of the subject. In some embodiments the relative abundance of at least one order of bacteria selected from Clostridiales, Erysipelotrichales, and Lactobacillales is decreased in the microbiota of the colon of the subject. In some embodiments the relative abundance of at least one order of bacteria selected from Enterobacteriales, Bacteriodales, and Verrucomicrobiales is increased in the microbiota of the colon of the subject; and the relative abundance of at least one order of bacteria selected from Clostridiales, Erysipelotrichales, and Lactobacillales is decreased in the microbiota of the colon of the subject.

In some embodiments the relative abundance of at least one family of bacteria selected from Enterobacteriaceae and Bacteroidaceae is increased in the microbiota of the colon of the subject. In some embodiments the relative abundance of at least one family of bacteria selected from Erysipelotrichaceae, Prevotellaceae, Coriobacteriaceae, and Alcaligenaceae is decreased in the microbiota of the colon of the subject. In some embodiments the relative abundance of at least one family of bacteria selected from Enterobacteriaceae and Bacteroidaceae is increased in the microbiota of the colon of the subject; and the relative abundance of at least one family of bacteria selected from Erysipelotrichaceae, Prevotellaceae, Coriobacteriaceae, and Alcaligenaceae is decreased in the microbiota of the colon of the subject.

In some embodiments the relative abundance of at least one genus of bacteria selected from *Escherichia, Bacteroides, Alistipes,* and *Akkermansia* is increased in the microbiota of the colon of the subject. In some embodiments the relative abundance of at least one genus of bacteria selected from *Clostridium* and *Lactobacillus* is decreased in the microbiota of the colon of the subject. In some embodiments the relative abundance of at least one genus of bacteria selected from *Escherichia, Bacteroides, Alistipes,* and *Akkermansia* is increased in the microbiota of the colon of the subject; and the relative abundance of at least one genus of bacteria selected from *Clostridium* and *Lactobacillus* is decreased in the microbiota of the colon of the subject.

In some embodiments the relative abundance of *Akkermansia muciniphila* is increased in the microbiota of the colon of the subject.

In some embodiments the relative abundance of at least one type of bacteria selected from Gammaproteobacteria, Alphaproteobacteria, Enterobacteriaceae (e.g., *Escherichia*), Bacteriodetes, and Verrucomicrobia (e.g., *Akkermansia*) is increased in the microbiota of the colon of the subject. In some embodiments the relative abundance of at least one type of bacteria selected from Firmicutes (Clostridia), Erysiopelotrichaceae is decreased in the microbiota of the colon of the subject.

In some embodiments the relative abundance of at least one type of bacteria selected from Gammaproteobacteria, Alphaproteobacteria, Enterobacteriaceae (e.g., *Escherichia*), Bacteriodetes, and Verrucomicrobia (e.g., *Akkermansia*) is increased in the microbiota of the colon of the subject; and the relative abundance of at least one type of bacteria selected from Firmicutes (Clostridia), Erysiopelotrichaceae is decreased in the microbiota of the colon of the subject.

In some embodiments the methods further comprise collecting a stool sample from the subject and assaying the microbiota profile in the stool sample to determine the relative abundance of at least one phylum of bacteria selected from Proteobacteria, Bacteriodetes, Verrucomicrobia, and Firmicutes; and/or to determine the relative abundance of at least one class of bacteria selected from Gammaproteobacteria, Alphaproteobacteria, Bacteriodetes, Clostridia, Erysipelotrichia, and Bacilli; and/or to determine the relative abundance of at least one order of bacteria selected from Enterobacteriales, Bacteriodales, Verrucomicrobiales, Clostridiales, Erysipelotrichales, and Lactobacillales; and/or to determine the relative abundance of at least one family of bacteria selected from Enterobacteriaceae, Bacteroidaceae, Erysipelotrichaceae, Prevotellaceae, Coriobacteriaceae, and Alcaligenaceae; and/or to determine the relative abundance of at least one genus of bacteria selected from *Escherichia, Bacteroides, Alistipes, Akkermansia, Clostridium,* and *Lactobacillus*; and/or to determine the relative abundance of *Akkermansia muciniphila*. In some embodiments the stool sample is collected at least one time point selected from before initiation of administering at least one agent that increases oxygen tension and/or redox potential and/or pH, during a course of administering at least one agent that increases oxygen tension and/or redox potential and/or pH, and after completion of administering a course of at least one agent that increases oxygen tension and/or redox potential and/or pH.

In some embodiments in which the relative abundance of a type of bacteria is increased in the colon of the subject the increase in relative abundance is at least 25%, at least 50%, at least 75%, at least 100% (i.e., one fold), at least 200% (i.e., two fold), at least 300%, at least 400%, at least 500%, at least 600%, at least 700%, at least 800%, at least 900%, at least 1,000% (i.e., ten fold), or at least 10,000% (i.e., 100 fold). In some embodiments in which the relative abundance of a type of bacteria is decreased in the colon of the subject the decrease in relative abundance is at least 10%, at least 25%, at least 50%, at least 75%, at least 90% (i.e., ten fold), at least 95% (i.e., 20 fold), at least 99% (i.e., 100 fold), at least 99.9% (i.e., 1000 fold).

In some embodiments of the methods the at least one agent that increases oxygen tension and/or redox potential and/or pH in the colon of a subject is administered to the subject without administering an enzyme to the subject. In some embodiments of the methods the at least one agent that increases oxygen tension and/or redox potential and/or pH in the colon of a subject is administered to the subject without administering an enzyme that oxidizes ethanol to acetate to the subject.

G. Systems

System for weight management of a subject are also provided. The systems comprise a plurality of compositions of the invention. In some embodiments each of the plurality of compositions in the system comprises a different active agent or a different combination of active agents. In some embodiments each of the plurality of compositions in the system is in the form of a different oral dosage form even if at least two of the compositions comprise the same active agent or same combination of active agents.

H. Uses

This invention also encompasses use of at least one agent that increases oxygen tension and/or redox potential and/or pH in the colon of a subject to manage the weight of the subject.

This invention also encompasses use of at least one agent that increases oxygen tension and/or redox potential and/or pH in the colon of a subject for manufacturing a medicament intended to manage the weight of the subject.

EXAMPLES

The examples are provided to further define the disclosure without, however, limiting the disclosure to the specifics of these examples.

Example 1: Administration of Enteric Coated Sustained Release Formulation to Mice Materials C57BL/6 WT adult male mice are used (20-30 weeks of age, weight 15-45 g). Active agents are supplied from Sigma—Catalase (C1345 SIGMA, Catalase from bovine liver), carbamide peroxide (04078 FLUKA, Hydrogen peroxide-Urea adduct powder, 15-17% active oxygen basis), Sodium bicarbonate (S5761 SIGMA). Active agents are micro encapsulated in hydrophobic material (food grade wax or lipids, 20-1000 um diameter particle size) for sustained release over hours to days and the resulting particles are also coated with pH sensitive enteric coatings enabling the particles to be released only when they reached the small intestine and not before they leave the stomach. Ingredients are stored at 4 C before administration.

Methods

Control mice are fed a normal chow diet ad libitum or periodically. Test groups are fed a normal chow diet ad libitum or periodically supplemented with one or more combinations of active agents, suspended in physiological buffer, e.g. phosphate buffered saline. Mice are orally gavaged with the active agent daily or twice a day or 3 times a day. A test group of 3-5 mice is treated with each active agent or combination of active agents. Test groups are treated for from one to four weeks. Weight measurements are performed and fecal samples collected at the beginning of the experiment, once to seven times every week for the duration of the experiment, and at the end of the experiment. Fecal samples are immediately frozen at −20 C and then are submitted to a commercial sequencing center for analysis.

16S rDNA illumina sequencing is performed on fecal mouse samples to quantify the phylogenetic structure of the gut microbiota. OTUs are classified at the phyla, family, genera and species level. Based on this, relative abundance of each species are determined and the community structures are compared using phylogenetic distance analysis tools (e.g. Unifrac) to measure and confirm shifts in the gut microbiome. In addition, specific phyla, genera and/or species relative abundances are compared across each timepoint for the test and control groups to score discrete shifts in the microbiota structure.

The active ingredients are tested at the following dosages:
Carbamide peroxide (oxygen source): 1 ng/kg to 100 mg/kg.
Sodium bicarbonate (pH modifier): 1 microgram/kg to 1 g/kg.
Catalase (peroxide catalyst): 01 ng/kg to 100 mg/kg.

Test Group I is treated with carbamide peroxide at a dose of 10 micrograms/kg four times a day for one week.

Test Group II is treated with sodium bicarbonate at a dose of 20 mg/kg four times a day for one week.

Test Group III is treated with carbamide peroxide at a dose of 10 micrograms/kg and with catalase at a dose of 10 micrograms/kg four times a day for one week.

Test Group IV is treated with carbamide peroxide at a dose of 10 micrograms/kg, with sodium bicarbonate at a dose of 20 mg/kg, and with catalase at a dose of 10 micrograms/kg, all administered four times a day for one week.

A control group of mice is also followed for the full week.

Results

A significant increase in the relative abundance of at least one type of bacteria selected from Gammaproteobacteria, Alphaproteobacteria, Enterobacteriaceae (*Escherichia*), Bacteriodetes, Verrucomicrobia (*Akkermansia*) is observed in each of the test groups relative to the abundance in the control group. A significant decrease in the relative abundance of at least one type of bacteria selected from Firmicutes, Clostridia, Erysiopelotrichaceae is observed in each of the test groups relative to the abundance in the control group.

Discussion

The microbiota of the human gut is gaining broad attention owing to its association with a wide range of diseases, ranging from metabolic disorders (e.g. obesity and type 2 diabetes) to autoimmune diseases (such as inflammatory bowel disease and type 1 diabetes), cancer and even mental disorders (e.g. depression). Murine animals have become the go-to model of choice for studies in this newly emerging field. With their easy maintenance and similarity to humans, mouse models allow perturbations in gut microbiota to be studied in a controlled experimental setup. This allows establishing causality of the complex host-microbiota interactions and in confirming mechanistic hypotheses.

Mouse models provide great power to predict effects of microbiota interventions on humans. For example, it has been shown that gastric bypass surgery induces very similar shifts in the gut microbiota of mice and humans [A. P. Liou, M. et al., "Conserved Shifts in the Gut Microbiota Due to Gastric Bypass Reduce Host Weight and Adiposity," Sci. Transl. Med. 5, 178ra41 (2013); H. Zhang et al., Human gut microbiota in obesity and after gastric bypass," Proc Natl Acad Sci USA. 2009 Feb. 17; 106(7): 2365-2370; J. V. Li et al., "Metabolic Surgery Profoundly Influences Gut Microbial-Host Metabolic Crosstalk," Gut. 2011 September; 60(9): 1214-1223]. Antibiotics have a similar effect on gut metabolome and microbial community structure both in mouse and humans and they can lead to similar *Clostridium Difficile* infection susceptibility [C. M. Theriot, et al., "Antibiotic-induced shifts in the mouse gut microbiome and metabolome increase susceptibility to *Clostridium difficile* infection," Nature Communications 5, Article number: 3114 doi:10.1038/ncomms4114]. More recently, it has been shown that non-caloric artificial sweeteners can cause gut microbiota dysbiosis to induce glucose intolerance in a similar manner in mouse and human experimental subjects [J. Suez, et al., "Artificial sweeteners induce glucose intolerance by altering the gut microbiota," Nature 514, 181-186 (9 Oct. 2014)].

In view of this established similarity between the mouse and human gut microbiotas, the positive outcome of this mouse study will be predictive of the therapeutic potential of the active agents and methods of the invention. Similar modifications to the guts of mice and humans are established as causing similar modifications to the gut microbiotas of mice and humans. And modifications to the mouse gut microbiota have been shown to cause physiological changes to mice that are similar to the physiological changes observed in humans when the human gut microbiota is modified in a similar manner. Accordingly, the positive results that are obtained from this example demonstrate the utility of the invention to skilled artisans.

Example 2: Enteric Coated Capsule Formulation

Carbamide peroxide and catalase react to produce oxygen in aqueous environments. To deliver oxygen in the colon, both carbamide peroxide and catalase are protected from gastric media before they are exposed and react in the distal small intestine and colon. In this example an HPMC based capsule formulation was developed. An enteric coating with dissolution start at pH 7 (Eudragit FS 30D) was used to achieve distal ileum release of the capsule ingredients and colon targeting. This formulation is suitable for oral administration.

Materials

The following materials were used: Carbamide peroxide (Spectrum Chemical), Catalase from *Aspergillus niger* (American Laboratories Incorporated), VCap Plus size 2 capsules (Capsugel), Eudragit FS 30D (Evonik), Polysorbate 80 (Fisher), PEG 400 (Croda) SR40377, Capmul MCM EP (Abitec), Deionized water, 4 L Beaker, 8 oz amber coated glass bottle, Turbula mixer, Magnetic hot plate, Magnetic stir bar, and Fluid bed dryer.

Preparation of Formulation of Carbamide Peroxide-Catalase in Enteric Coated Capsule The carbamide peroxide-catalase blend formulation was prepared at 100 mg carbamide peroxide and 100 mg per catalase (*Aspergillus niger* (750 Baker units)) per capsule for oral administration. The blend was filled into a size 2 HPMC based capsule coated with enteric polymer for protection from acidic media.

The capsules were prepared as follows. First, 50 g of carbamide peroxide and 50 g of catalase were placed into an 8 oz amber coated glass bottle. The blend was prepared by placing the bottle in a Turbula mixer and mixing for approximately 5 minutes. 500 size 2 HPMC capsules were then each filled with 200 mg of the blend.

To prepare the coating material, the following components were measured into a beaker: 8.8 g polysorbate, 9.0 g PEG 400, 7.2 g Capmul CMC EP, and 113.2 g DI water. The water was then heated to 70-80° C. A magnetic stir bar was then added and the mixture was stirred until it was completely homogeneous. 264.1 g of DI water was then slowly added to the hot mixture and 597.7 g of Eudragit FS 30D suspension was then poured into the mixture with stirring. The suspension was then passed through a 0.5 mm sieve.

An aeromatic fluid bed dryer with Wurster column was then used to spray coat the suspension onto the filled HPMC capsules with a product temperature of ~25° C. and nozzle pressure of ~1 bar. The coating level was 30 mg of solid/ capsule. The coated capsules were then dried at room temperature overnight.

Characterization of Capsule Dissolution

Dissolution of the capsules was characterized in a two stage experiment. The first stage was conducted using 0.1N HCl (pH 1.2) where the capsules were soaked for 2 hours. Dissolution media was taken at the end of 2 hours to confirm the level of urea in the media. Urea was not detected at this time, confirming correct functioning of the enteric coating and no release of the carbamide peroxide-catalase blend under the tested acidic conditions.

In the second stage, the capsules were placed in PBS buffer (pH 7.4) for 1 hour. Samples were withdrawn at 0.5 hour and one hour to check the urea concentration of the solution. The oxygen level was measured in dissolution vessels to confirm the production of oxygen. At time 0, no oxygen was detected relative to baseline. In contrast, a sharp increase in the dissolved oxygen concentration was apparent and by 1-hour time point. The average level of oxygen increase in the three dissolution vessels was ~3.5 mg/L concentration. Dissolved oxygen was measured using a Milwaukee MW600 Dissolved Oxygen meter. The data are presented in Table 1. A greater than 90% dissolution was observed. Carbamide peroxide dissociates into urea and hydrogen peroxide when dissolved in water. Urea and hydrogen peroxide are separated by HILIC HPLC on Primesep N column. Both compounds can be monitored at low UV—200 nm. Method was used for determination and quantitation of hydrogen peroxide and urea in dissolution vessels. Data in table 1 show that capsule contents release within an hour as expected after enteric coating is able to dissolve in media with pH greater than 7.0.

TABLE 1

| Time (hour) | Formulation #1-1 | Formulation #1-2 | Formulation #1-3 |
|---|---|---|---|
| 0 | 0 | 0 | 0 |
| 0.5 | 24.5 | 30.3 | 35.7 |
| 1 | 93.1 | 99 | 95 |

Example 3: Enteric Coated Tablet Formulation

Carbamide peroxide and catalase react to produce oxygen in aqueous environments. To deliver oxygen in the colon, both carbamide peroxide and catalase are protected from gastric media before they are exposed and react in the distal ileum and colon. In this example an HPMC (hydroxypropyl methylcellulose) based, sustained release tablet formulation was developed. An enteric coating with dissolution start at pH 7 (Eudragit FS 30D) was used to achieve distal ileum release of the tablet ingredients. This formulation is suitable for oral administration.

Materials

The following materials were used: Carbamide peroxide (Spectrum Chemical), Catalase from *Aspergillus niger* (American Laboratories Incorporated), Eudragit FS 30D (Evonik), HPMC (K4M), Starch, Sodium stearyl fumerate, Polysorbate 80 (Fisher), PEG 400 (Croda) SR40377, Capmul MCM EP (Abitec), Deionized water, 4 L Beaker, 8 oz amber coated glass bottle, Tumble V-blender, Magnetic hot plate, Magnetic stir bar, and Fluid bed dryer.

Preparation of Formulation of Carbamide Peroxide-Catalase in Sustained Release Enteric Coated Tablet The carbamide peroxide-catalase blend formulation was prepared in a sustained release enteric coated tablet as follows. Carbamide peroxide particles were milled in a hammer mill to create particles with size less than 100 um. The tablet blend was then prepared by placing the powder ingredients listed in Table 2 in tumble v-blender and mixing until homogenous.

TABLE 2

| Material (%) | % | Weight/tablet (mg) |
|---|---|---|
| Carbamide peroxide | 20 | 100 |
| Catalase | 20 | 100 |
| HPMC (K4M) | 50.55 | 252.75 |
| Starch | 9 | 45 |
| Sodium stearyl fumerate | 0.45 | 2.25 |

Prepared powder blend was later loaded into a manual tablet press. Tablets were prepared using this manual tablet press at a force range of 30-35N using a press die accommodating 500 mg powder fill to achieve hardness of 250N.

To prepare the coating material, the following components were measured into a beaker: 8.8 g polysorbate, 9.0 g PEG 400, 7.2 g Capmul CMC EP, and 113.2 g DI water. The water was then heated to 70-80° C. A magnetic stir bar was then added and the mixture was stirred until it was completely homogeneous. 264.1 g of DI water was then slowly added to the hot mixture and 597.7 g of Eudragit FS 30D suspension was then poured into the mixture with stirring. The suspension was then passed through a 0.5 mm sieve.

An aeromatic fluid bed dryer with Wurster column was then used to spray coat the suspension onto the filled HPMC capsules with a product temperature of ~25° C. and nozzle pressure of ~1 bar. The coating level was 50 mg of solid/tablet. The coated tablets were then dried at room temperature overnight.

Characterization of Tablet Dissolution

The tablet dissolution studies were conducted in two stages. In the first stage the tablets were soaked for two hours in 0.1N HCl (pH 1.2). After two hours dissolution media was taken and analyzed to confirm the level of urea in the media with HPLC. No urea was detected at this time.

In the second stage, the tablets were placed in PBS buffer (pH 7.4) and incubated for six hours. Samples were withdrawn at 0.5, 1, 2, 3, 4, 5 and 6 hour(s) to check the urea concentration. The oxygen level was measured in one of the dissolution vessels to confirm the production of oxygen. At 0 hour, 0 mg/L of oxygen was detected relative to baseline. Production of oxygen then gradually increased and by the 6-hour time point the level reached a concentration of ~3 mg/L. Dissolved oxygen was measured using a Milwaukee MW600 Dissolved Oxygen meter.

A dissolution assay was performed in a 500 mL dissolution vessel using PBS pH 7.4 with 20 rpm mixing rate to characterize the properties of the tablet formulation. As shown in Table 3, close to 100% dissolution was achieved within 6 hours. Normal intestinal transit time in ascending colon is about 6 hours. Dissolution time of 6 hours was targeted to enable release of all actives slowly in the ascending colon during this transit period.

TABLE 3

Percent dissolution data for tablet formualtion

| Time (h) | Formulation#1-1 | Formulation#1-2 | Formulation#1-3 |
|---|---|---|---|
| 0 | 0 | 0 | 0 |
| 0.5 | 8.6 | 5.3 | 10.1 |
| 1 | 24.3 | 21.5 | 24.8 |
| 2 | 44.4 | 49.2 | 47.8 |
| 3 | 60.1 | 66.3 | 65.5 |
| 4 | 72.2 | 78.5 | 78.2 |
| 5 | 79.9 | 88.8 | 86 |
| 6 | 87.2 | 96 | 92.9 |

Example 4: Acceleration of Molecular Oxygen Formation By Catalase

In vitro oxygen release measurements from tablet and capsule formulations were performed to confirm that using catalase in the formulations of Examples 2 and 3 significantly accelerates the production of molecular oxygen from hydrogen peroxide.

Methods

Capsule formulations with or without catalase were separately placed in 50 mL falcon tubes holding 20 mL of PBS (pH 7.4). Capsules either contained 100 mg of carbamide peroxide plus 100 mg of catalase (+ catalase), or just 100 mg carbamide peroxide (− catalase). Five capsules were placed in each tube. Each tube was fitted with a plastic airtight lid through which a dissolved oxygen sensor probe was fitted (Milwaukee MW600). The probe was submerged in the media. Airtight containers prevented escape of produced oxygen and enabled oxygen accumulation within the tubes, leading to increased oxygen pressure in the headspace. Tubes were incubated at 25 C for 1 hour and dissolved oxygen concentration was recorded every thirty min. Baseline oxygen concentration was calibrated to 7.8 mg/L.

Results

The results are shown in Table 4. The data shows that including catalase along with carbamide peroxide in the formulations had a drastic effect on the speed of increase of dissolved oxygen in the tubes. Using formulations with catalase, oxygen concentrations in the tubes reached up to ~16 mg/L from a baseline of 7.8 mg/L at one hour. In contrast, at one hour for the formulations without catalase the dissolved oxygen reached only up to ~9 mg/L. These data show that including catalase along with the peroxide compound dramatically accelerates the decomposition of the peroxide and leads to rapid accumulation of molecular oxygen.

TABLE 4

| Time (hour) | (+) catalase #1 | (+) catalase #2 | (+) catalase #3 | (−) catalase #1 | (−) catalase #2 | (−) catalase #3 |
|---|---|---|---|---|---|---|
| 0 | 7.8 (mg/L) | 7.8 | 7.8 | 7.8 | 7.8 | 7.8 |
| 0.5 | 10.2 | 9 | 11 | 8.1 | 7.7 | 8.3 |
| 1 | 13.7 | 16.8 | 15.4 | 10.2 | 9.3 | 9 |

Example 5: Modulation of Gut Microbiome to Induce Weight Loss

The ability of the formulations of Examples 2 and 3 to modulate the gut microbiota of a human subject and to bring about weight loss was assessed in this example.

Methods

A healthy human subject (male, age 28, BMI 18.6) was dosed with the capsule and tablet formulations of Examples 2 and 3 in a longitudinal crossover study during a period of 10 weeks. The subject was dosed with tablets for five days (days 0, 1, 2, 3, and 4; the "first dosing period") and later with capsules for six days (days 33, 34, 35, 36, 37, and 38; the "second dosing period"). Additional details of the dosing schedule and the timing of microbiome sampling time points is presented in FIG. 1. Both formulations were dosed at 5 mg/day/kg body weight of carbamide peroxide and 5 mg/day/kg body weight of catalase (7500 Baker units/g). During each dosing period the subject took pills containing 100 mg of carbamide peroxide and 100 mg of catalase 3 times per day after each meal, (corresponding to 5 mg/day/kg body weight for both carbamide peroxide and catalase for this 60 kg subject). Throughout the whole study, the subject consumed the same plant rich diet (2000 kcal) every day except for a calorie restriction period at days 26-28, where the daily calories were reduced to 1500 kcals.

Fecal samples were collected using a commercially available microbiome sampling kit (OMNIgene-Gut, DNA Genotek). 16S rRNA sequencing was performed on the microbiome samples with amplification of V4 region. Throughout the study daily fasting body weight and body fat percentage (total body electrical conductance) measurements were performed in the mornings before the first meal of the day. In addition, baseline microbiome and weight measurements were taken at 30 days and 60 days before any dosing (day 0) to serve as long-term baseline.

Results

A dramatic increase in the relative abundance of Proteobacteria (aerobic genera) in the gut microbiota of the subject was observed when dosing with tablet or capsule formulations. In addition, this substantial change in the gut microbiota coincided with a drastic and significant weight loss (more than 2.5% in one week) each time the subject was dosed. The subject recovered the lost weight approximately 2 weeks after dosing cessation, whereas the gut microbiota returned to baseline almost immediately after dosing stop (FIGS. 1-3), suggesting that the observed changes in the microbiota are a direct result of the dosing with actives.

Figure 3:
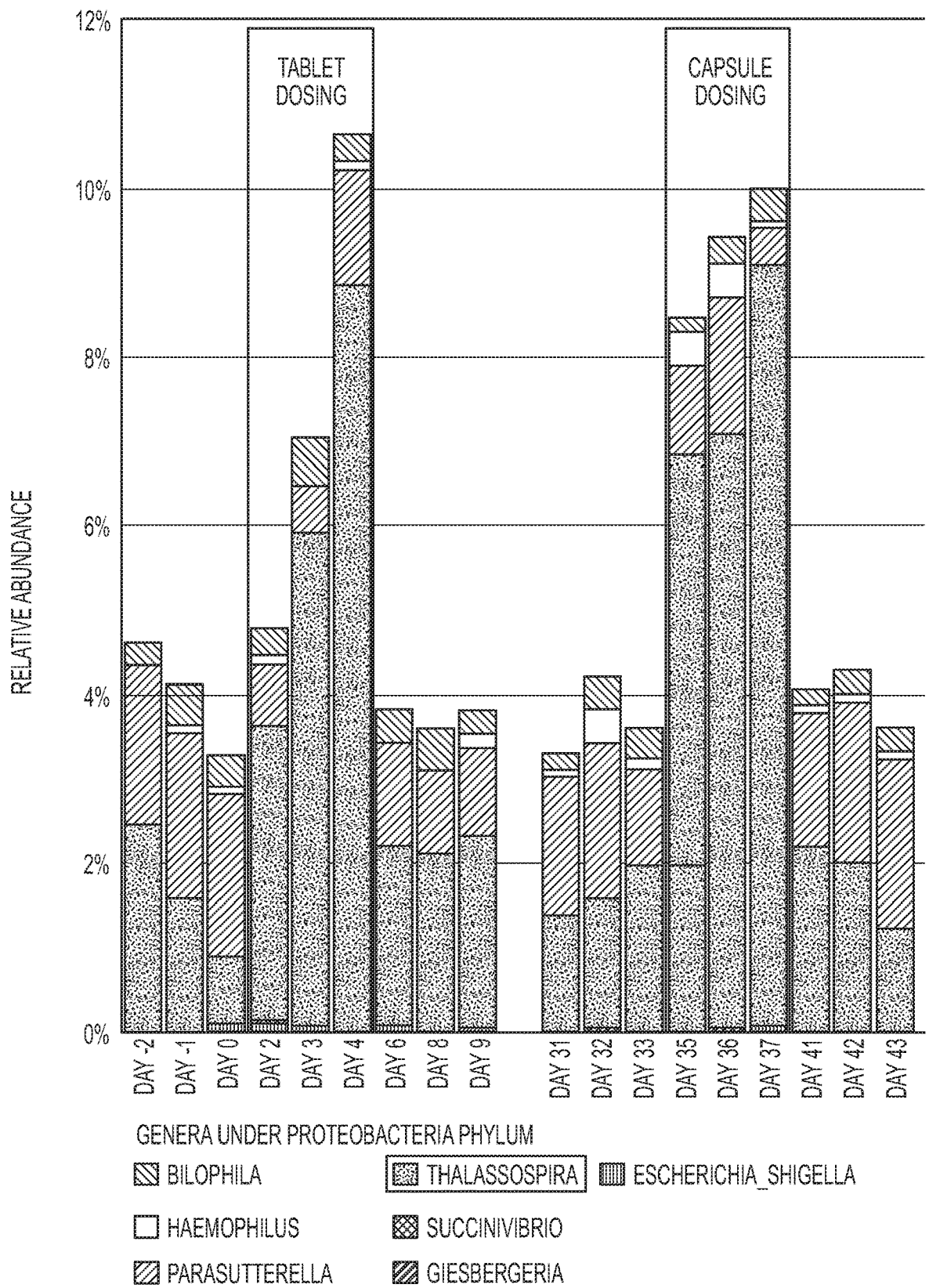
FIG. 3 shows changes in relative abundance of genera within the Proteobacteria phylum throughout the study. *Thalassospira* (aerobic) and *Parasuteralla* (strictly anaerobic) dominated the Proteobacteria at baseline. *Escherichia/Shigella* group was mostly undetectable. During dosing, *Thalassospira* increased significantly in relative abundance.

Baseline microbiota of the subject included several genera generally described as facultative anaerobes or strict aerobes. *Thalassospira*, recognized as a strict aerobic or facultatively anaerobic genus of α-Proteobacteria [Tsubouchi, T., Ohta, Y., Haga, T., Usui, K., Shimane, Y., Mori, K., Tanizaki, A., Adachi, A., Kobayashi, K., Yukawa, K., et al. (2014). *Thalassospira alkalitolerans* sp. nov. and *Thalassospira mesophila* sp. nov., isolated from a decaying bamboo sunken in the marine environment, and emended description of the genus *Thalassospira*. Int. J. Syst. Evol. Microbiol. 64, 107-115] commonly isolated from oligotrophic water environments initially constituted about 1% of the subject's total microbiota, but during first phase of dosing with tablet formulations, increased to almost 9%. Another aerobic bacteria group which was detected, *Escherichia-Shigella*, a genus belonging to Gamma-Proteobacteria, initially constituted 0.001% of the total microbiota (about two orders of magnitude lower than average levels observed in the general population, reference: ubiome) and was undetectable in most samples throughout the study (FIG. 3).

Figure 4:
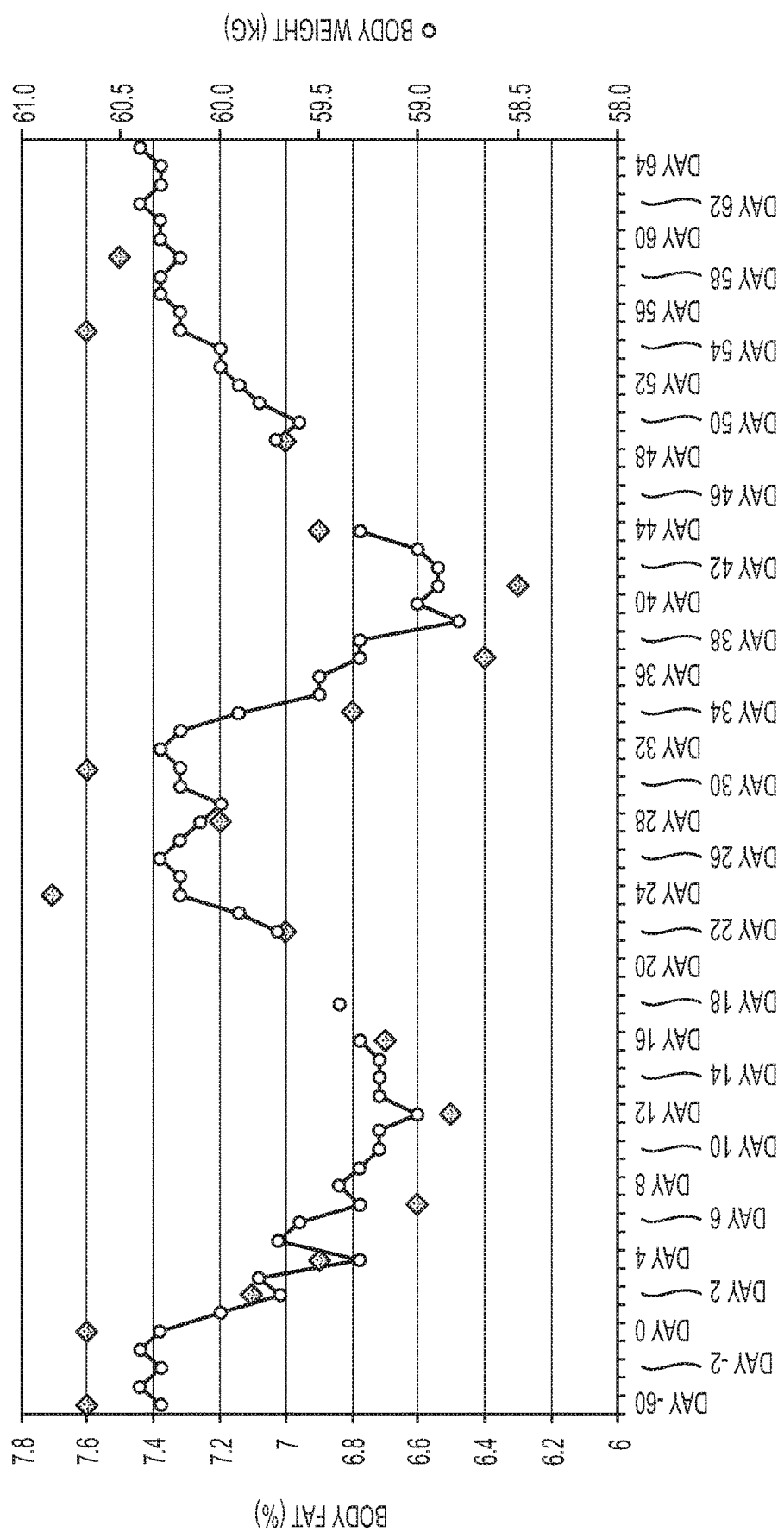
FIG. 4 shows bodyweight and fat percentage changes during the longitudinal clinical study. Circles represent body weight and diamonds represent body fat percentage values. Throughout the study there was a high correlation between measured body fat percentage and body weight values, indicating that the dosing leads to weight loss through fat mass reduction.

Following tablet dosing, the subject recovered his lost weight and his weight re-stabilized around pre-dosing levels (FIG. 1). To compare degree of weight loss observed with regular caloric restriction to that observed when the test composition was adminstered, the subject ate a reduced calorie diet (1500 kcal) for three days. During the three day period the subject lost only a small fraction of weight that had been lost during any three day period of the first dosing period. The subjects weight also recovered rapidly after the restriction was ended (FIGS. 1 and 4). Adverse events such as headache, fatigue and hunger were recorded during this restriction period. None of these symptoms were present during dosing periods. These symptoms resolved after the subject returned to the regular 2000-kcal diet. These results show that dosing with the test formulation had a much more profound effect on energy homeostasis than simple caloric restriction and caused vastly greater and faster weight loss.

Figure 2:
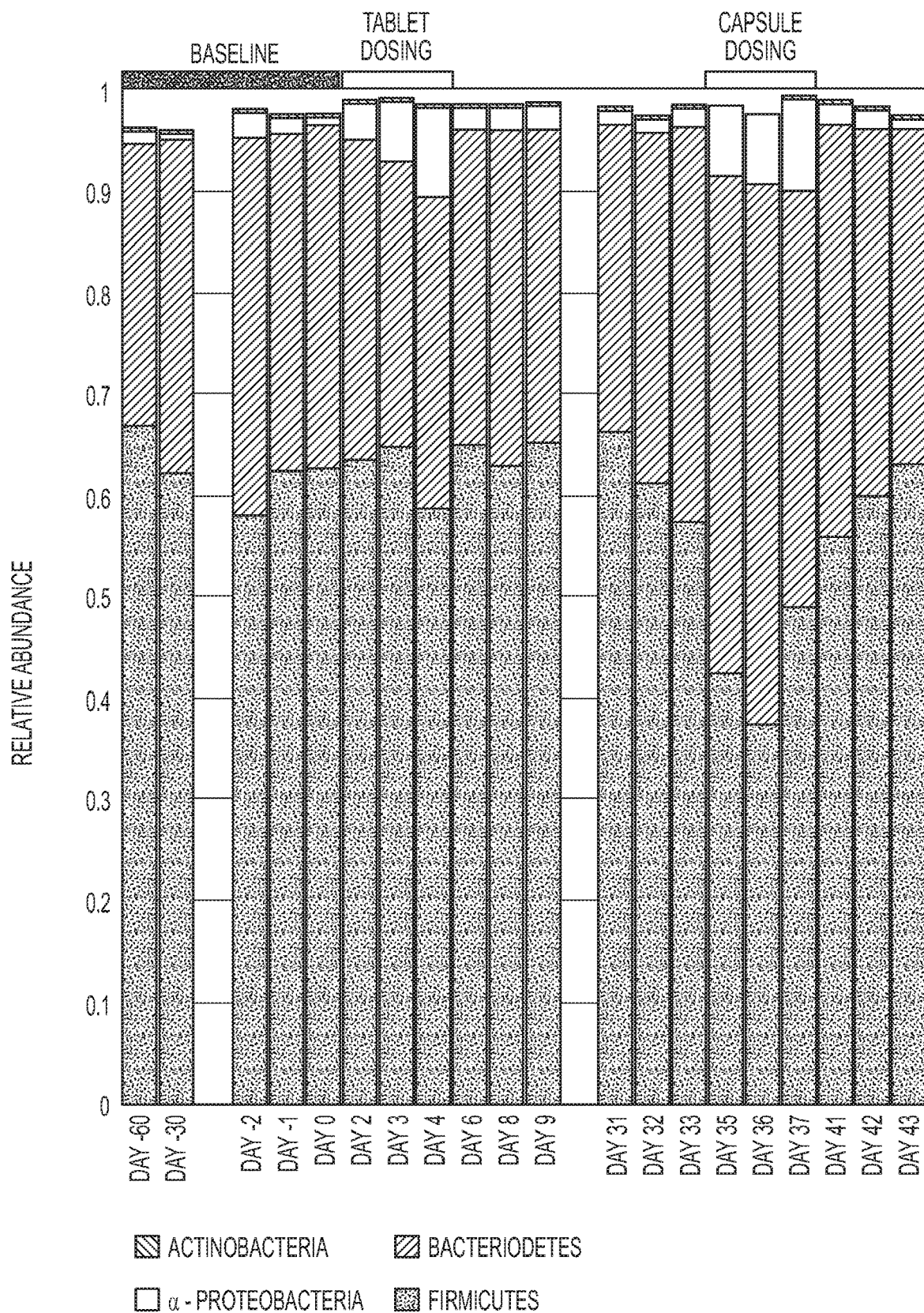
FIG. 2 shows changes in relative abundance of dominant phyla present in the colon microbiota of the subject. Note the expansion of α-Proteobacteria relative abundance and decrease in Firmicutes relative abundance during dosing periods.

After the subject recovered back to the baseline body weight a second phase of dosing was initiated using the capsule formulation of Example 2. Similar to what was observed with tablet dosing, the subject rapidly lost 2.5% of body weight during the 6-day dosing period and had a drastic and rapid gut microbiota shift towards aerobic genera (*Thalassospira*) compared to baseline (1% to 9%). Microbiota composition immediately returned back to baseline state after dosing was stopped (FIGS. 1-3). During the capsule dosing period, in addition to the increase in aerobic genera within Proteobacteria, a corresponding sharp decrease in the relative abundance of Firmicutes was also observed (~65% to ~40%), whereas the relative abundance of Bacteriodetes increased (~30% to ~50%). These results show that tested formulations achieve the desired effects of shifting the gut microbiota to Proteobacteria (i.e more aerobic bacteria) and profound weight loss.

Throughout the study, no adverse events were recorded, except for absence of bowel movements on the first day following dosing initiation both with tablet and capsule dosings. The subject also reported experiencing drastic reduction in appetite and hunger, changes in taste of certain food items and coffee during the dosing periods.

Discussion

The amount of weight loss observed with the tested formulations (greater than 2.5% in less than a week) is quite dramatic and on par with weight loss rates observed after gastric bypass surgery (1-3% per week). [Karamanakos, S. N., Vagenas, K., Kalfarentzos, F., and Alexandrides, T. K. (2008). Weight loss, appetite suppression, and changes in fasting and postprandial ghrelin and peptide-YY levels after Roux-en-Y gastric bypass and sleeve gastrectomy: a prospective, double blind study. Ann. Surg. 247, 401-407.] Considering that the subject was already very low BMI (18.6) to begin with, the observed degree of weight loss is all the more extraordinary. To put this into context, a 5% weight loss over a much longer period of time is regarded as a gold standard in weight management for greatly alleviating co-morbidities associated with weight gain, such as insulin resistance. [Magkos, F., Fraterrigo, G., Yoshino, J., Luecking, C., Kirbach, K., Kelly, S. C., de Las Fuentes, L., He, S., Okunade, A. L., Patterson, B. W., et al. Effects of Moderate and Subsequent Progressive Weight Loss on Metabolic Function and Adipose Tissue Biology in Humans with Obesity. Cell Metab. 2016 Apr. 12; 23(4):591-601] As a comparison, a widely used weight loss drug, Phentermine, achieves 4-5% weight loss over one year. Another commercially available weight loss drug, Xenical, leads to average weight loss of 3-4% over one year). [Daneschvar, H. L., Aronson, M. D., and Smetana, G. W. (2016). FDA Approved Anti-obesity Drugs in the United States. Am. J. Med.]. Throughout the longitudinal study there was a high correlation between measured body fat percentage and body weight values, showing that dosing with the tested compositions leads to changes in body composition towards less fat mass (FIG. 4).

The observed weight loss with dosing could be due to energy homeostasis regulation by the immune system. Given that certain aerobic bacteria in the Proteobacteria phylum cause most enteric infections, it might be the case that artificially increasing aerobic bacteria in the gut (either with the tested formulations or gastric bypass surgery) could lead to an anorexic response orchestrated by the immune system. Infection induced anorexia pathways may be engaged leading to less food intake and lowering of blood glucose levels as part of an evolutionarily conserved adaptive response to phylum level changes in the gut microbiome composition. [Exton, M. S. (1997). Infection-induced anorexia: active host defence strategy. Appetite 29, 369-383.] However, in contrast to a real infection, the types of aerobic bacteria that increase in gastric bypass or with the tested formulations are not pathogens, but commensal, and do not cause systemic inflammatory response. In fact, gastric bypass surgery leads to profound reduction in systemic and adipose tissue inflammation. [Sams, V. G., Blackledge, C., Wijayatunga, N., Barlow, P., Mancini, M., Mancini, G., and Moustaid-Moussa, N. Effect of bariatric surgery on systemic and adipose tissue inflammation. Surg Endosc. (2015). 1-6] These results suggest that the anorexia of infection pathways may be independently stimulated using changes in the gut microbiota without inducing acute phase response or inflammation. [Kanra, G. Y. Y., Ozen, H., and Kara, A. (2006). Infection and anorexia. Turk. J. Pediatr. 48, 279-287.] The results of the present study identify a novel way to bring about gut microbiota changes that can activate the pathway to achieve its beneficial effects in a controlled manner.

Example 6: Modulation of Microbial Growth In Vitro

Batch microbial growth experiments were performed to assess whether the tested formulations can cause an increase in aerobic bacteria/proteobacteria under in vitro conditions that mimics the in vivo results presented in Example 5. Stool samples were incubated in standard thioglycollate media under anaerobic conditions with or without our tablet/capsule formulations.

Methods

Anaerobic thioglycollate media (Hardy Diagnostics) was heated to boiling temperature to remove residual oxygen. 100 mL of media in a glass jar (200 mL) was inoculated with ~1 gram of fresh stool sample from a healthy human volunteer under sterile conditions. Four cultures were prepared: a test culture with capsule formulation added, a test culture with tablet formulation added, and two replicate controls with no formulation added (completely anaerobic controls). Inoculated media were incubated in separate anaerobic chambers maintained by AnaeroPack-Anaero (a commercially available oxygen absorbing and carbon dioxide generating agent, Mitsubishi Gas Chemical Co., Inc.) for 24 hours at 37 C under static conditions. After incubation, the culture media was thoroughly mixed and 2 mL of media was sampled from each culture for subsequent 16S rRNA sequencing. Final microbial density in each culture was measured using a spectrophotometer (CO 8000 Biowave Cell Density Meter) at 600 nm.

Results

Figure 5:
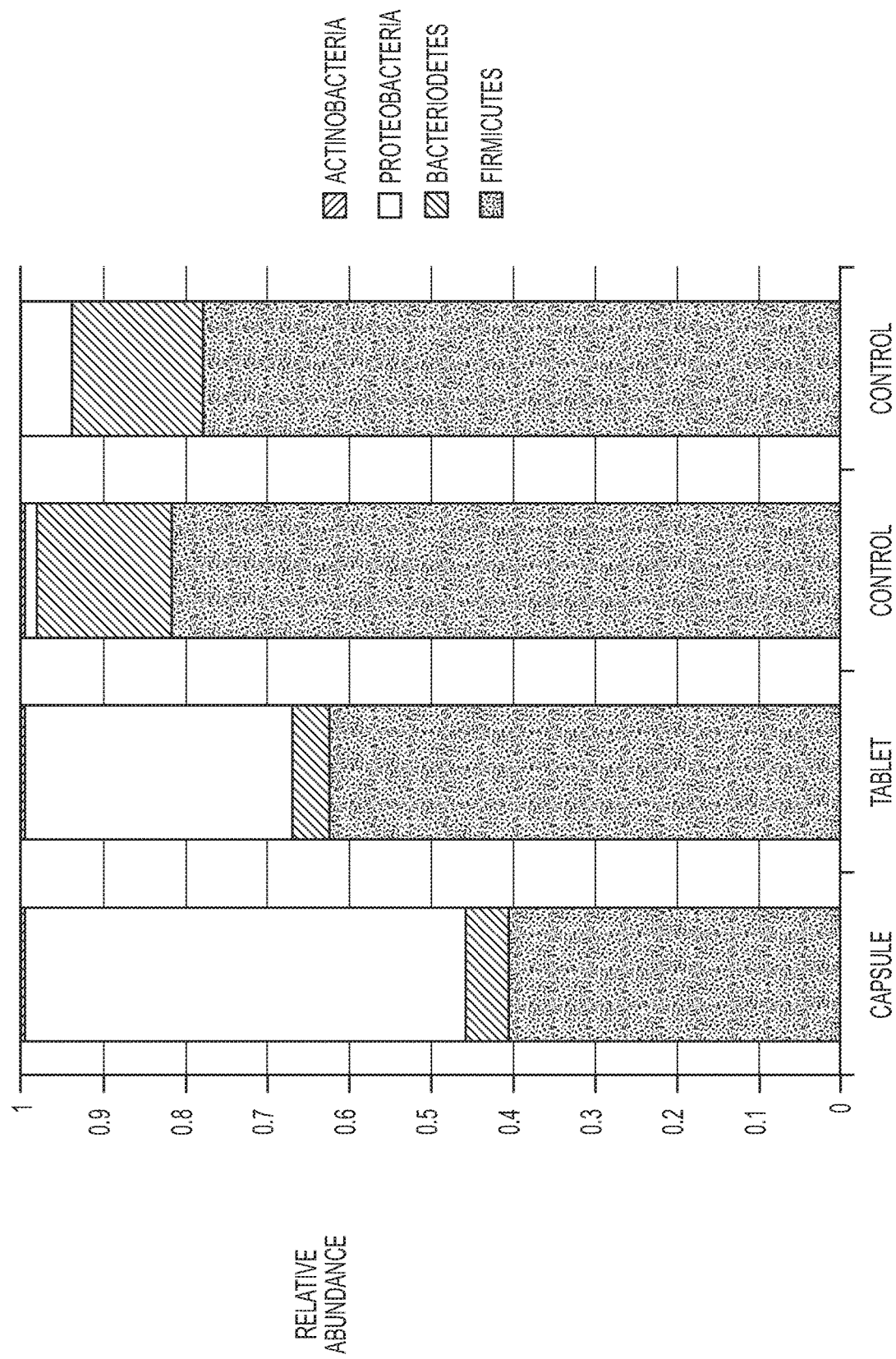
FIG. 5 shows relative abundance of phyla measured under in vitro cultivation. Note the large increase in aerobic bacteria (Proteobacteria) in the cultures having added capsule and tablet formulations of carbamide peroxide and catalase compared to anaerobic control cultures.

The sequencing results presented in FIG. 5 clearly indicate that the tested cause a drastic shift towards Proteobacteria (30-50%) However, in anaerobic control cultures proteobacteria (aerobic bacteria) constituted at most 4% of the total bacteria. Gamma-proteobacteria (*Escherichia/Shigella* group) constituted the majority of the expansion in the cultures with the test formulations added. In contrast, in the control cultures a dominance of anaerobic bacteria in a similar composition to a typical gut microbiome sample was observed. A change of color of the media towards purple/pink at the end of the incubation period was also observed in the cultures with the added test compositions, indicating presence of excess oxygen in the media as thioglycollate broth turns purple due to an increase in dissolved oxygen concentration. Significantly lower cell density (biomass) was also observed in the cultures containing the test composition (Optical density at 600 nm was 3.5 (capsule), 3.3 (tablet), and 4.7 and 5.0 in the two control anaerobic cultures). The limited carrying capacity of the cultures with extra oxygen may be due to less efficient substrate utilization or more waste product accumulation by the altered bacterial composition. Optical density is not a measure of growth rate but rather amount of total biomass.

Example 7: Administration of Non-Formulated Peroxide

This example addressed the requirement for enteric coating to deliver carbamide peroxide to the colon in order to achieve its effects on the gut microbiome.

Methods 6-7 week old Sprague Dawley lean rats were orally gavaged three times daily either with carbamide peroxide dissolved in acidified water as the treatment arm (total dose=600 mg/kg body weight) or with acidified water alone as the control arm (12 mice per arm) for 3 days. Gavage solution was prepared immediately before oral gavaging was performed. Each rat was fed a normal chow diet throughout (Research Diets) and kept under 12 hr-12 hr light-dark cycle in its own metabolic cage. Fresh fecal samples were collected at day 0 (basal measurement, before dosing start) and at the end of day 3 (after the final dose) and immediately stored at −80 C. Later, 16S rRNA sequencing was performed to measure relative abundance of different taxa in the stool samples. Body weight and food intake were measured daily.

Results

No significant change in the gut microbiota composition was observed between Day 0 and Day 3 samples of the treatment arm and the control arm. Likewise, no significant differences were observed in the body weight and food intake between the control and treatment arms.

Discussion

These results are consistent with the hypothesis that administering an oxygen source to the stomach or proximal small intestine does not result in delivery of oxygen to the distal small intestine or colon and that increasing the oxygen level in the distal small intestine or colon is necessary to significantly change the microbiome and to induce weight loss. In contrast, the formulations of Examples 2 and 3 do deliver the oxygen source to the distal small intestine or colon and in turn do significantly change the microbiome. It is noteworthy that the peroxide dose used in this rodent study was more than 100 times higher than the dose used in Example 5. Despite the higher dose, no effect on the microbiota in rodents was observed. This contrasts with the observed substantial shifts towards increased numbers of facultative anaerobic/aerobic bacteria in Example 5 when using a much smaller dose with a colon-specific delivery vehicle. This result suggests that peroxide when delivered without a protective coating or encapsulation rapidly decomposes (or gets absorbed) before gastric emptying occurs or it has the chance to reach the distal gut.

Example 8: Modulation of Gut Microbiome to Induce Weight Loss

The ability of the formulation of Examples 2 to modulate the gut microbiota of a human subject and to bring about weight loss was assessed in this example.

Methods

Two additional healthy human subjects were dosed with the capsule formulation of Example 2 in a longitudinal crossover study during a period of 4 weeks. (Subject #2: Female, Age 57, BMI 23.7, Baseline Body Weight 60.5 kg. Subject #3: Male, Age 56, BMI 28.6, Baseline Body Weight 92.7 kg.) The subjects were not on any medications or dietary supplements prior to the study. Subjects were dosed with capsules for seven days (days 0, 1, 2, 3, 4, 5 and 6; the "first dosing period") and later again with capsules for three days (days 19, 20, and 21; the "second dosing period"). Additional details of the dosing schedule and the timing of microbiome sampling time points is presented in FIGS. 6 and 7. Both subjects were dosed at approximately 5 mg/day/kg body weight of carbamide peroxide and 5 mg/day/kg body weight of catalase (7500 Baker units/g). During each dosing period the subjects took pills containing 100 mg of carbamide peroxide and 100 mg of catalase 3 times per day after each meal, (corresponding to 5 mg/day/kg body weight for both carbamide peroxide and catalase for Subject #2, and 3.2 mg/day/kg body weight for both carbamide peroxide and catalase for Subject #3). Throughout the whole study, the subjects consumed the same ad libitum diet, where the daily calorie intake ranged between 1500-2500 kcals.

Fecal samples were collected using a commercially available microbiome sampling kit (OMNIgene-Gut, DNA Genotek). 16S rRNA sequencing was performed on the microbiome samples with amplification of V4 region. Throughout the study daily fasting body weight measurements were performed in the mornings before the first meal of the day. In addition, baseline weight measurements were taken at 30 days and 60 days before any dosing (day 0) to serve as long-term baseline. For subject #2, fasting glucose measurements were performed in the morning before first meal of the day using an IME-DC blood glucose meter (IME-DC GmbH).

Results

Dramatic increases in the relative abundance of Proteobacteria (aerobic genera) in the gut microbiota of the subjects was observed when dosing (FIGS. 6-9). Relative abundance of Proteobacteria increased from 12% to 42% in Subject #2; and from 3% to 11% in Subject #3. In addition, this substantial change in the gut microbiota coincided with a drastic and significant weight loss (−3.5% for Subject #2; −2.5% for Subject #3 over 7 days). The subjects partially recovered the lost weight approximately 1-2 weeks after dosing cessation.

Figure 6:
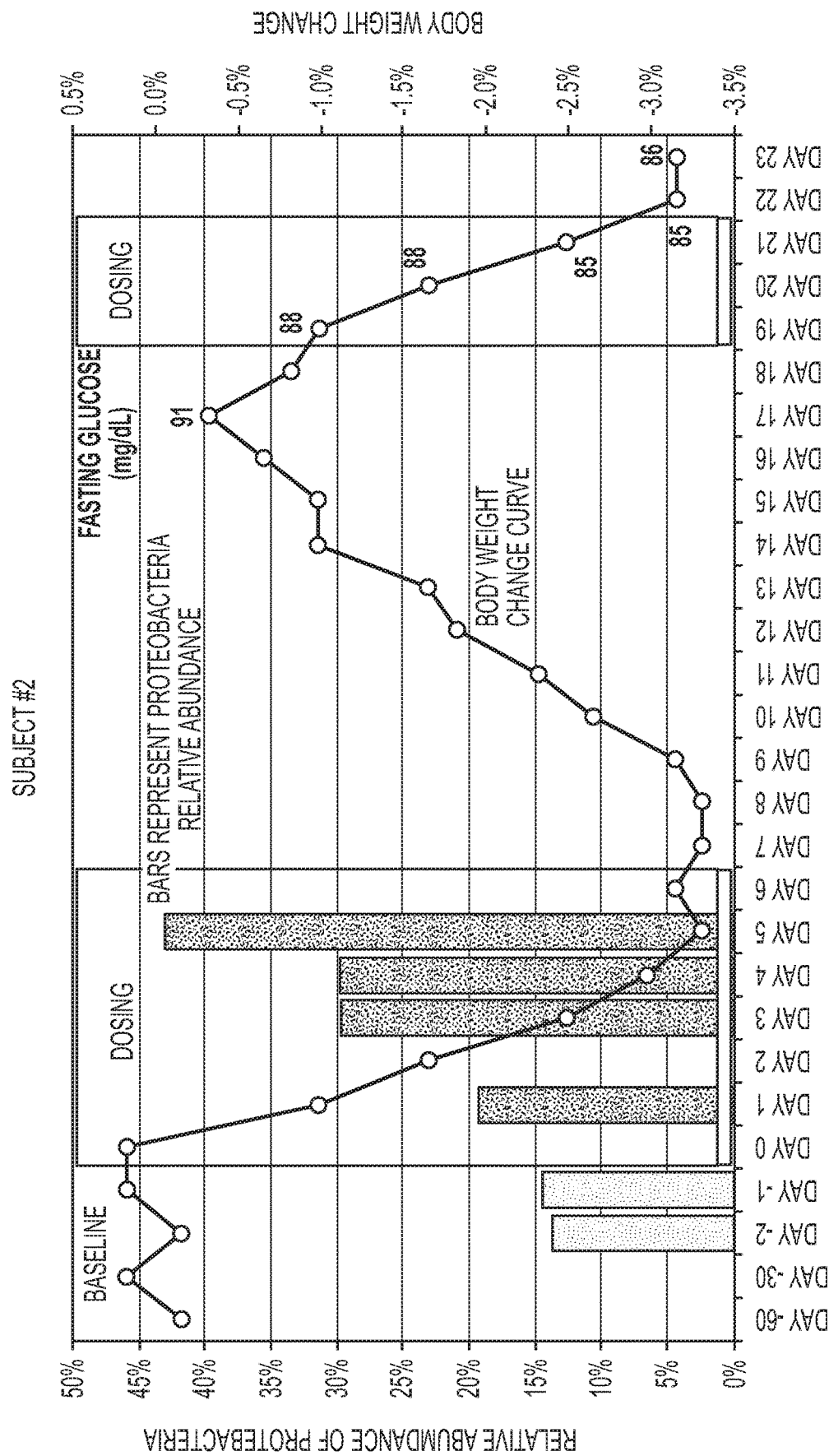
FIG. 6 shows body weight and colonic microbiota changes for Subject #2. Circles correspond to body weight change data (right vertical axis). Bars indicate relative abundance of phylum Proteobacteria (left vertical axis). Darker bars correspond to data from samples taken during dosing, whereas lighter bars are data from samples gathered before dosing. The white horizontal bars along the x-axis highlight the dosing periods. The days where no microbiome measurement was taken were left as blank bars. Microbiome was not sampled during second dosing period. Fasting blood glucose measurements (mg/dL) are indicated next to body weight data points taken the corresponding day.
Figure 7:
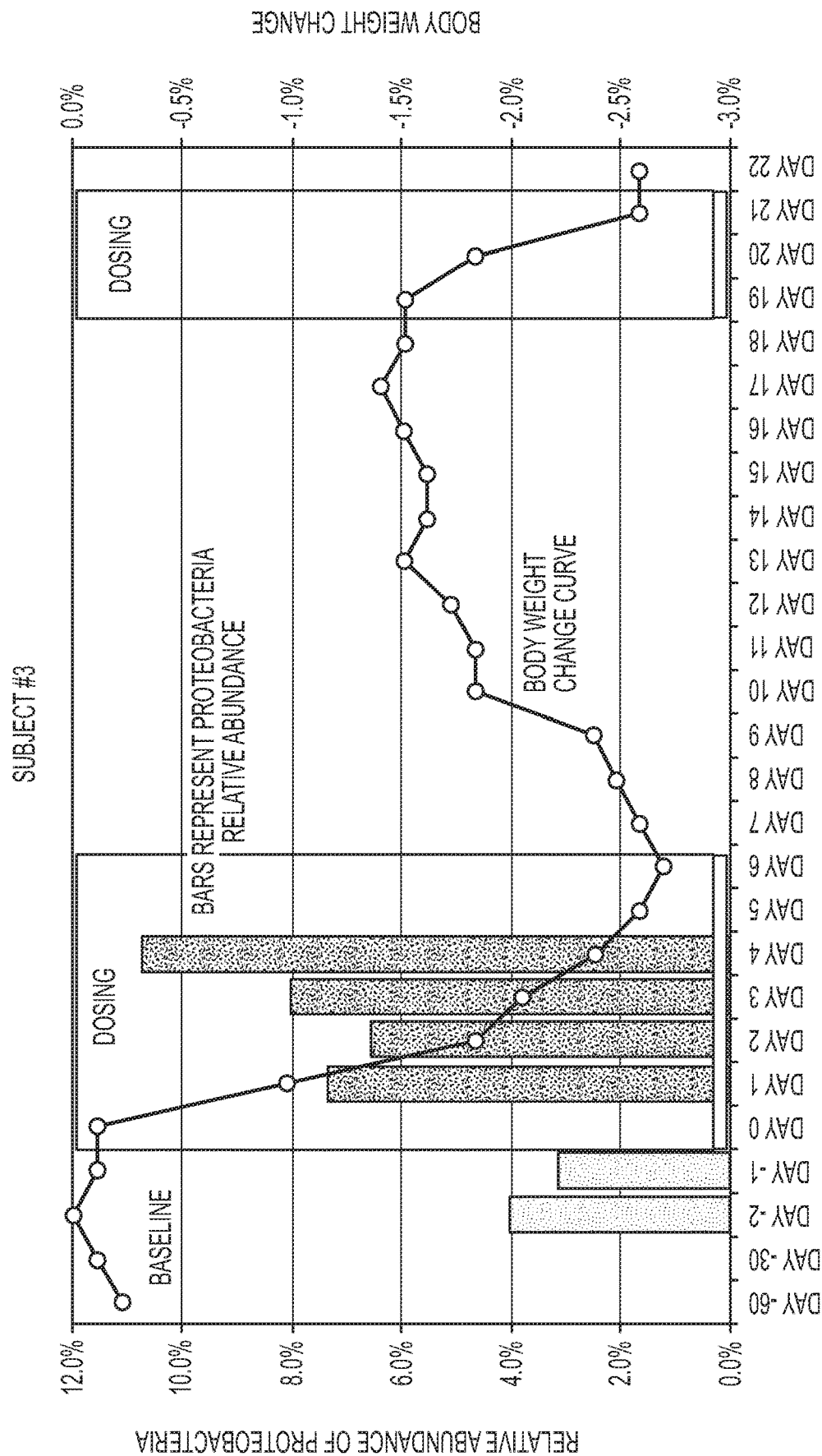
FIG. 7 shows body weight and colonic microbiota changes for Subject #3. Circles correspond to body weight change data (right vertical axis). Bars indicate relative abundance of phylum Proteobacteria (left vertical axis). Darker bars correspond to data from samples taken during dosing, whereas lighter bars are data from samples gathered before dosing. The white horizontal bars along the x-axis highlight the dosing periods. The days where no microbiome measurement was taken were left as blank bars. Microbiome was not sampled during second dosing period.
Figure 8:
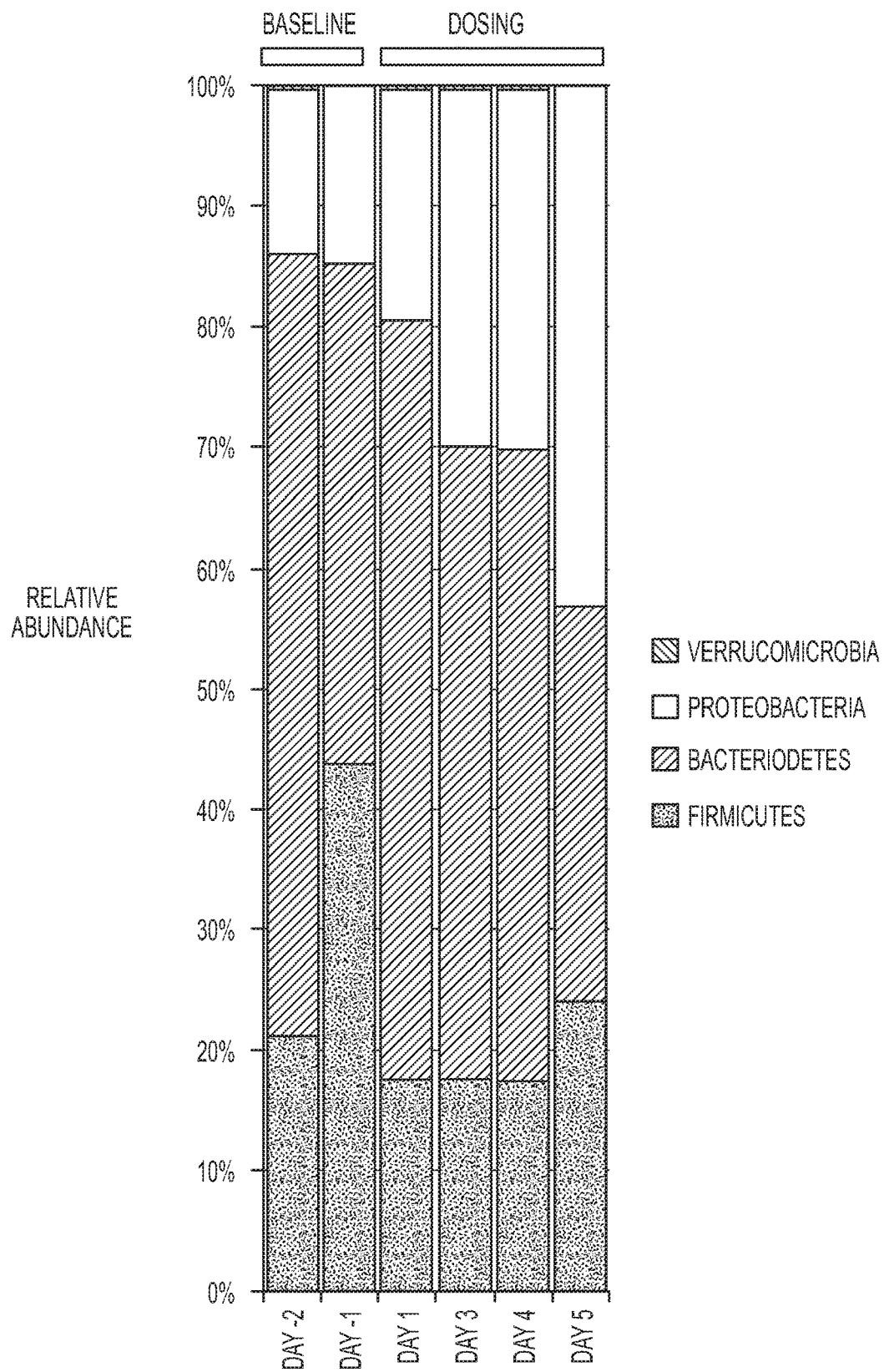
FIG. 8 shows changes in relative abundance of dominant phyla present in the colon microbiota of Subject #2 during first dosing period. Note the significant and sustained increase Proteobacteria relative abundance.
Figure 9:
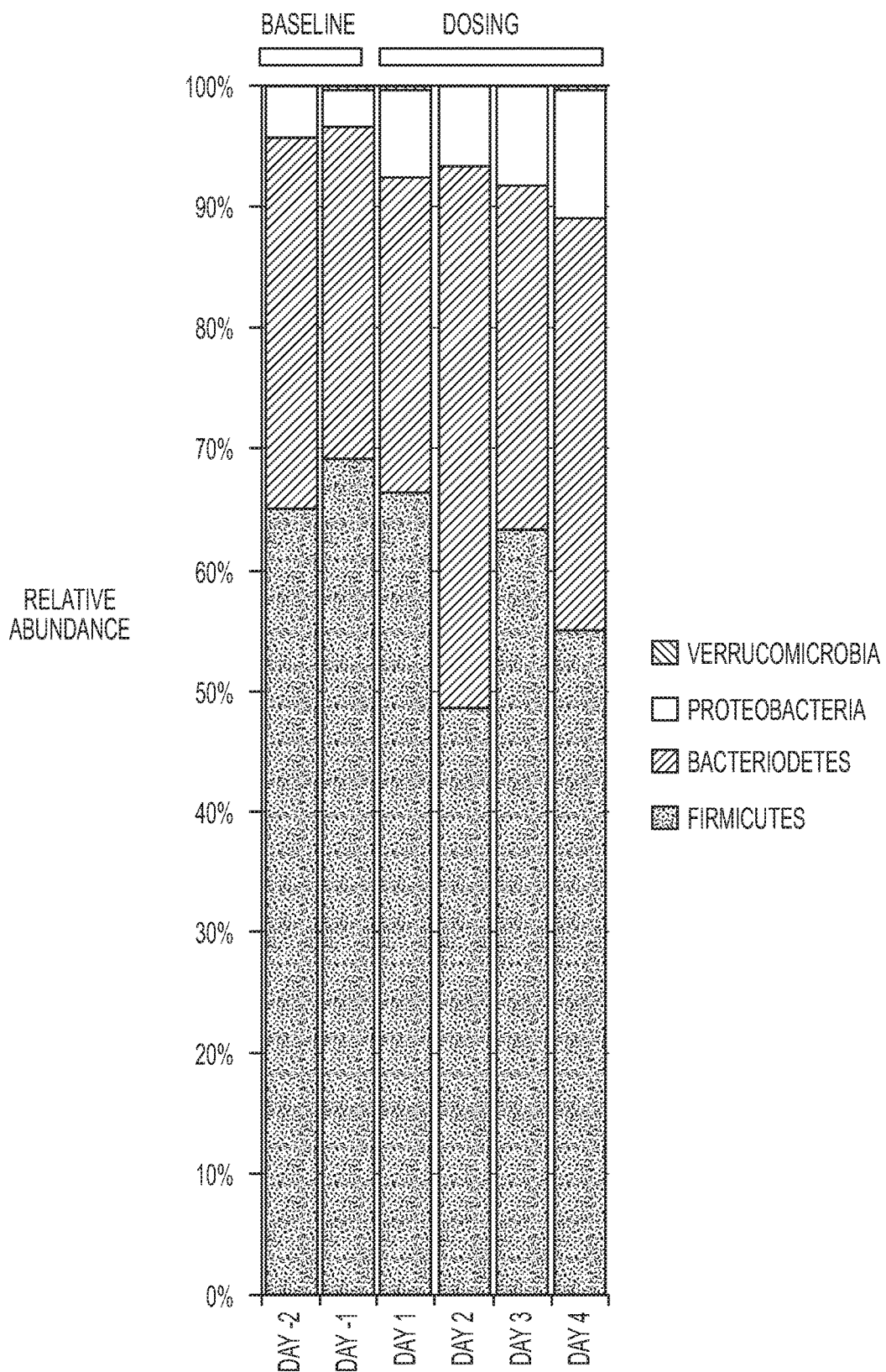
FIG. 9 shows changes in relative abundance of dominant phyla present in the colon microbiota of Subject #3 during first dosing period. Note the significant and sustained increase Proteobacteria relative abundance.

Next, a second phase of dosing was initiated, again using the capsule formulation of Example 2. Similar to what was observed with first dosing, the subjects rapidly lost at least 1% of body weight during the 3-day additional dosing period. No microbiota samples were taken during this period. Subject #2 had fasting blood glucose measurements taken right before and during the second dosing period (FIG. 6). Fasting blood glucose levels went from average baseline of ~90 mg/dL down to 85 mg/dL over the course of 3 days. These results show that the tested formulations achieve the desired effects of shifting the gut microbiota to more Proteobacteria (i.e more aerobic bacteria) and profound weight loss, and lower fasting blood glucose levels.

Throughout the study, no adverse events were recorded, except for mild constipation, soft stools, metallic/bitter taste sensation on tongue, and dehydration. The subjects also reported experiencing drastic reduction in appetite and hunger.

Discussion

The profound weight loss observed with Subjects #2 and #3 (range of 2.5 to 3.5% loss in a week) is again quite dramatic and on par with weight loss rates observed after gastric bypass surgery (1-3% per week). [Karamanakos, S. N., Vagenas, K., Kalfarentzos, F., and Alexandrides, T. K. (2008). Weight loss, appetite suppression, and changes in fasting and postprandial ghrelin and peptide-YY levels after Roux-en-Y gastric bypass and sleeve gastrectomy: a prospective, double blind study. Ann. Surg. 247, 401-407.].

The baseline Proteobacteria relative abundance observed across all 3 subjects varied between ~1-10%. This range is fairly normal as Proteobacteria (aerobic bacteria) generally constitute a small fraction of the gut microbiota in healthy human subjects. The peak proportional increase in the relative abundance of Proteobacteria during dosing varied from ~4× to ~10× compared to baseline. Across all subjects there was a substantial and consistent increase in the relative abundance of Proteobacteria. Subject #2 had a relatively high Proteobacteria abundance as baseline, yet during dosing still showed a substantial increase in Proteobacteria up to ~42% of the total gut microbiota.

The variation observed in the peak relative abundance of Proteobacteria across subjects could be due to many different factors such as intestinal transit time, bioavailability of the enteric dosage form, gastrointestinal pH profile variation affecting the release timing of the actives. The observed gradual increase in the Proteobacteria abundance during dosing period could be a reflection of colonic transit time, which usually varies from 24 hours to 72 hours across the healthy human population. It is possible that a change in the microbiota of the proximal colon of a subject may only be detected in its full effect after several days, depending on the colonic transit time of the subject.

The invention claimed is:
1. A method of weight management for a human subject in need thereof, the method comprising steps of:
orally administering to a subject who is overweight or obese an enterically-coated oxygen-releasing composition comprising sodium percarbonate,
wherein the enterically-coated oxygen-releasing composition is characterized in that it achieves release of oxygen when assayed in PBS buffer at pH 7.4 after immersion at pH 1.2 for 2 hours.

2. The method of claim 1, wherein the weight management comprises at least one of weight loss, maintenance of weight loss, avoiding weight gain, body mass index (BMI) reduction, maintenance of BMI reduction, and avoiding BMI gain.

3. The method of claim 1, wherein the weight management comprises reducing the weight of the subject by at least 5%.

4. The method of claim 3, wherein the weight management comprises reducing the weight of the subject by at least 10%.

5. The method of claim 1, wherein the composition is further characterized in that, when contacted with a sample containing both anaerobic and aerobic bacteria, an increase in the relative abundance of aerobic bacteria is achieved.

6. The method of claim 5, wherein the relative abundance of bacteria in the phylum Proteobacteria is increased.

7. The method of claim 1, wherein the enteric coating dissolves at a pH above 6.0.

8. The method of claim 1, wherein the enteric coating dissolves at a pH above 7.0.

9. The method of claim 1, wherein the composition is formulated for sustained release.

10. The method of claim 1, wherein the release of oxygen is measured by a dissolved oxygen meter.

11. A method of weight management for a human subject in need thereof, the method comprising:
orally administering to a subject who is overweight or obese an oxygen-releasing composition formulated for enteric delivery of its active to the small intestine and/or large intestine of the subject, wherein the active is or comprises sodium percarbonate.

12. The method of claim 11, wherein the weight management comprises at least one of weight loss, maintenance of weight loss, avoiding weight gain, body mass index (BMI) reduction, maintenance of BMI reduction, and avoiding BMI gain.

13. The method of claim 11, wherein the weight management comprises reducing the weight of the subject by at least 5%.

14. The method of claim 13, wherein the weight management comprises reducing the weight of the subject by at least 10%.

15. The method of claim 11, wherein the relative abundance of at least one of aerobic bacteria and facultative anaerobic bacteria in the microbiota of the colon of the subject is increased by at least 100%.

16. The method of claim 15, wherein the relative abundance of bacteria in the phylum Proteobacteria is increased in the microbiota of the colon of the subject by at least 100%.

17. The method of claim 11, wherein the active is administered at a dose of 5 mg to 100 mg of hydrogen peroxide equivalent.

18. The method of claim 11, wherein the active is administered at a dose of 20 mg to 40 mg of hydrogen peroxide equivalent.

19. The method of claim 11, wherein the composition is administered as an oral dosage form comprising the active and an enteric coating encasing the active.

20. The method of claim 19, wherein the enteric coating dissolves at a pH above 6.0.

21. The method of claim 19, wherein the enteric coating dissolves at a pH above 7.0.

22. The method of claim 19, wherein the oral dosage form is formulated for sustained release.

23. In a method of managing weight by inducing weight loss in an overweight or obese subject who is a candidate for bariatric surgery, the improvement that comprises:
instead of performing bariatric surgery on the subject, orally administering to the subject an oxygen-releasing composition formulated for enteric delivery of its active in the small and/or large intestine, wherein the active is or comprises sodium percarbonate.

24. In a method of managing weight by inducing weight loss in an overweight or obese subject who is a candidate for bariatric surgery, the improvement that comprises:
instead of performing bariatric surgery on the subject, orally administering to the subject a composition that is an enteric oxygen delivery composition comprising sodium percarbonate and characterized in that it releases oxygen when assayed in PBS buffer at pH 7.4 after immersion at pH 1.2 for 2 hours.

25. In a method of managing weight by inducing weight loss in an overweight or obese subject who is a candidate for bariatric surgery, the improvement that comprises:
instead of performing bariatric surgery on the subject, orally administering an enterically coated oral dosage form of an oxygen-releasing composition comprising sodium percarbonate.

26. A method comprising a step of:
orally administering to a subject who is overweight or obese an enterically coated oxygen-releasing composition comprising sodium percarbonate.

27. A method comprising a step of:
administering to an overweight or obese subject a composition comprising sodium percarbonate that is an enteric oxygen delivery composition in that it achieves delivery preferentially to the small and/or large intestine.

* * * * *